US012235579B2

United States Patent
Ou et al.

(10) Patent No.: US 12,235,579 B2
(45) Date of Patent: Feb. 25, 2025

(54) METHOD FOR PRODUCING ACTINIC RAY-SENSITIVE OR RADIATION-SENSITIVE RESIN COMPOSITION, PATTERN FORMING METHOD, AND METHOD FOR MANUFACTURING ELECTRONIC DEVICE

(71) Applicant: FUJIFILM Corporation, Tokyo (JP)

(72) Inventors: Keiyu Ou, Shizuoka (JP); Naohiro Tango, Shizuoka (JP); Kei Yamamoto, Shizuoka (JP); Kazuhiro Marumo, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 442 days.

(21) Appl. No.: 17/548,595

(22) Filed: Dec. 13, 2021

(65) Prior Publication Data

US 2022/0107561 A1  Apr. 7, 2022

Related U.S. Application Data

(63) Continuation of application No. PCT/JP2020/018062, filed on Apr. 28, 2020.

(30) Foreign Application Priority Data

Jun. 28, 2019 (JP) ................................. 2019-122288
Feb. 26, 2020 (JP) ................................. 2020-030480

(51) Int. Cl.
*G03F 7/004* (2006.01)
*C07C 309/17* (2006.01)
(Continued)

(52) U.S. Cl.
CPC .......... *G03F 7/0045* (2013.01); *C07C 309/17* (2013.01); *C07C 309/42* (2013.01);
(Continued)

(58) Field of Classification Search
None
See application file for complete search history.

(56) References Cited

U.S. PATENT DOCUMENTS 9,551,928 B2    1/2017   Yamaguchi et al.
2010/0255418 A1  10/2010  Yamaguchi et al.
(Continued)

FOREIGN PATENT DOCUMENTS

EP    3919981     12/2021
JP    2014149409   8/2014
(Continued)

OTHER PUBLICATIONS

"Office Action of Taiwan Counterpart Application", issued on Sep. 6, 2023, with partial English translation thereof, p. 1-p. 10.
(Continued)

*Primary Examiner* — Sean M DeGuire
*Assistant Examiner* — Andrew Preston Traywick
(74) *Attorney, Agent, or Firm* — JCIPRNET

(57) ABSTRACT

A method for producing an actinic ray-sensitive or radiation-sensitive resin composition of an embodiment of the present invention is a method for producing an actinic ray-sensitive or radiation-sensitive resin composition including at least a resin having a polarity that increases due to decomposition by the action of an acid, a compound that generates an acid upon irradiation with actinic rays or radiation, and a solvent, in which the compound that generates an acid upon irradiation with actinic rays or radiation includes one or more compounds selected from the group consisting of a compound (I) to (III) below, and the actinic ray-sensitive or radiation-sensitive resin composition is produced by mixing a first solution including the resin having a polarity that
(Continued)

increases by the action of an acid and a first solvent with the one or more compounds selected from the group consisting of the compound (I) to (III).

10 Claims, 1 Drawing Sheet

(51) Int. Cl.

| | | |
|---|---|---|
| C07C 309/42 | (2006.01) | |
| C07C 311/09 | (2006.01) | |
| C07C 311/48 | (2006.01) | |
| C07C 311/51 | (2006.01) | |
| C07C 381/12 | (2006.01) | |
| C07D 327/06 | (2006.01) | |
| C07D 327/08 | (2006.01) | |
| C07D 333/46 | (2006.01) | |
| C07D 333/76 | (2006.01) | |
| C08F 220/18 | (2006.01) | |
| C08F 220/28 | (2006.01) | |
| G03F 7/038 | (2006.01) | |
| G03F 7/039 | (2006.01) | |

(52) U.S. Cl.
CPC .......... *C07C 311/09* (2013.01); *C07C 311/48* (2013.01); *C07C 311/51* (2013.01); *C07C 381/12* (2013.01); *C07D 327/06* (2013.01); *C07D 327/08* (2013.01); *C07D 333/46* (2013.01); *C07D 333/76* (2013.01); *C08F 220/1806* (2020.02); *C08F 220/1807* (2020.02); *C08F 220/1808* (2020.02); *C08F 220/1809* (2020.02); *C08F 220/1811* (2020.02); *C08F 220/1812* (2020.02); *C08F 220/1818* (2020.02); *C08F 220/281* (2020.02); *C08F 220/283* (2020.02); *G03F 7/038* (2013.01); *G03F 7/039* (2013.01); *C07C 2603/74* (2017.05)

(56) References Cited

U.S. PATENT DOCUMENTS

2015/0331314 A1* 11/2015 Yamaguchi .......... G03F 7/0397
430/311
2018/0292751 A1 10/2018 Asakawa et al.

FOREIGN PATENT DOCUMENTS

| JP | 2015024989 | 2/2015 |
| JP | 5746829 | 7/2015 |
| KR | 20150103195 | 9/2015 |
| TW | 201435505 | 9/2014 |

OTHER PUBLICATIONS

"Office Action of Japan Counterpart Application" with English translation thereof, issued on Aug. 30, 2022, p. 1-p. 5.
"Search Report of Europe Counterpart Application", issued on Oct. 4, 2022, p. 1-p. 8.
"Office Action of China Counterpart Application", issued on Dec. 19, 2022, with English translation thereof, p. 1-p. 16.
"International Search Report (Form PCT/ISA/210) of PCT/JP2020/018062," mailed on Jul. 21, 2020, with English translation thereof, pp. 1-5.
"Written Opinion of the International Searching Authority (Form PCT/ISA/237)" of PCT/JP2020/018062, mailed on Jul. 21, 2020, with English translation thereof, pp. 1-8.
"Office Action of Korea Counterpart Application", issued on Oct. 17, 2023, with English translation thereof, p. 1-p. 12.

* cited by examiner

METHOD FOR PRODUCING ACTINIC RAY-SENSITIVE OR RADIATION-SENSITIVE RESIN COMPOSITION, PATTERN FORMING METHOD, AND METHOD FOR MANUFACTURING ELECTRONIC DEVICE

CROSS-REFERENCE TO RELATED APPLICATIONS

This application is a Continuation of PCT International Application No. PCT/JP2020/018062 filed on Apr. 28, 2020, which claims priority under 35 U.S.C. § 119(a) to Japanese Patent Application No. 2019-122288 filed on Jun. 28, 2019 and Japanese Patent Application No. 2020-030480 filed on Feb. 26, 2020. Each of the above application(s) is hereby expressly incorporated by reference, in its entirety, into the present application.

BACKGROUND OF THE INVENTION

1. Field of the Invention

The present invention relates to a method for producing an actinic ray-sensitive or radiation-sensitive resin composition, a pattern forming method, and a method for manufacturing an electronic device.

2. Description of the Related Art

Since the advent of a resist for KrF excimer laser (248 nm), a pattern forming method utilizing chemical amplification has been used in order to compensate for a decrease in sensitivity due to light absorption. For example, in a positive tone chemical amplification method, first, a photoacid generator included in the exposed area decomposes upon irradiation with light to generate an acid. Then, in a post-exposure baking (PEB) step and the like, a solubility in a developer changes by, for example, changing an alkali-insoluble group contained in a resin included in an actinic ray-sensitive or radiation-sensitive resin composition (hereinafter also referred to as a "resist composition") to an alkali-soluble group by the catalytic action of an acid thus generated. Thereafter, development is performed using a basic aqueous solution, for example. As a result, the exposed area is removed to obtain a desired pattern.

For miniaturization of semiconductor elements, the wavelength of an exposure light source has been shortened and a projection lens with a high numerical aperture (high NA) has been advanced, and currently, an exposure machine using an ArF excimer laser having a wavelength of 193 nm as a light source is under development.

Under these circumstances, various configurations have been proposed as actinic ray-sensitive or radiation-sensitive resin compositions.

For example, JP2015-024989A discloses an acid generator including a salt represented by Formula (I) as a component used in a resist composition.

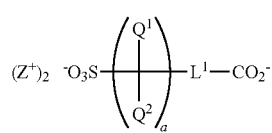

(I)

SUMMARY OF THE INVENTION

The present inventors have conducted studies on the resist composition described in JP2015-024989A, and have thus found that in a case where a pattern is formed using the resist composition, many defects are generated in the pattern. That is, they have clarified that the resist composition needs a further improvement to suppress defects of a pattern formed.

Therefore, an object of the present invention is to provide a method for producing an actinic ray-sensitive or radiation-sensitive resin composition that is capable of forming a pattern having suppressed defects.

In addition, another object of the present invention is to provide a pattern forming method including the method for producing an actinic ray-sensitive or radiation-sensitive resin composition, and a method for manufacturing an electronic device, using the pattern forming method.

The present inventors have conducted intensive studies to accomplish the objects, and as a result, they have completed the present invention. That is, the present inventors have found that the objects can be accomplished by the following configurations.

[1] A method for producing an actinic ray-sensitive or radiation-sensitive resin composition including at least a resin having a polarity that increases due to decomposition by an action of an acid, a compound that generates an acid upon irradiation with actinic rays or radiation, and a solvent,
  in which the compound that generates an acid upon irradiation with actinic rays or radiation includes one or more compounds selected from the group consisting of a compound (I) to a compound (III), each of which will be described later,
  the method comprising mixing a first solution including the resin having a polarity that increases by the action of an acid and a first solvent with the one or more compounds selected from the group consisting of the compound (I) to the compound (III) to produce the actinic ray-sensitive or radiation-sensitive resin composition.

[2] The method for producing an actinic ray-sensitive or radiation-sensitive resin composition as described in [1],
  in which an SP value of the first solvent is less than 18.5 MPa$^{1/2}$.

[3] The method for producing an actinic ray-sensitive or radiation-sensitive resin composition as described in [1] or [2],
  in which the actinic ray-sensitive or radiation-sensitive resin composition is produced by mixing the first solution and a second solution including a second solvent having a higher SP value than the first solvent and the one or more compounds selected from the group consisting of the compound (I) to the compound (III).

[4] The method for producing an actinic ray-sensitive or radiation-sensitive resin composition as described in [3], in which the SP value of the second solvent is 18.5 MPa$^{1/2}$ or more.

[5] The method for producing an actinic ray-sensitive or radiation-sensitive resin composition as described in [3] or [4],
  in which a concentration of solid contents of the first solution is 5.0% to 20.0% by mass, and
  the actinic ray-sensitive or radiation-sensitive resin composition is produced by further mixing a third solution obtained by mixing the first solution and the second solution with the first solvent.

[6] A pattern forming method comprising:
a step of forming a resist film on a support, using an actinic ray-sensitive or radiation-sensitive resin composition obtained by the method for producing an actinic ray-sensitive or radiation-sensitive resin composition as described in any one of [1] to [5];
a step of exposing the resist film; and
a step of developing the exposed resist film, using a developer.

[7] A method for manufacturing an electronic device, comprising the pattern forming method as described in [6].

According to the present invention, it is possible to provide a method for producing an actinic ray-sensitive or radiation-sensitive resin composition that is capable of forming a pattern having suppressed defects.

In addition, according to the present invention, it is also possible to provide a pattern forming method including the method for producing an actinic ray-sensitive or radiation-sensitive resin composition, and a method for manufacturing an electronic device, using the pattern forming method.

DESCRIPTION OF THE PREFERRED EMBODIMENTS

Figure 1:
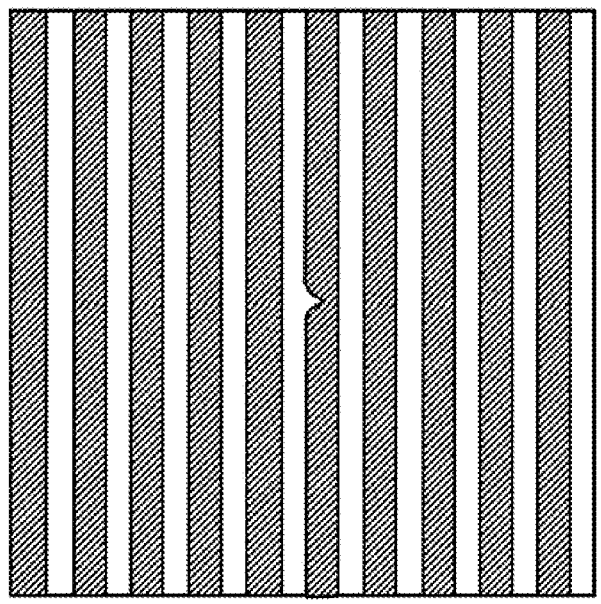
FIG. 1 is a schematic view for illustrating an evaluation method for defect evaluation after pattern formation, and is an example of a defect observed.

Hereinafter, a method for producing an actinic ray-sensitive or radiation-sensitive resin composition, a pattern forming method, and a method for manufacturing an electronic device according to the present invention will be described in detail.

Description of configuration requirements described below may be made on the basis of representative embodiments of the present invention in some cases, but the present invention is not limited to such embodiments.

In notations for a group (atomic group) in the present specification, in a case where the group is cited without specifying whether it is substituted or unsubstituted, the group includes both a group having no substituent and a group having a substituent as long as this does not impair the spirit of the present invention. For example, an "alkyl group" includes not only an alkyl group having no substituent (unsubstituted alkyl group), but also an alkyl group having a substituent (substituted alkyl group). In addition, an "organic group" in the present specification refers to a group including at least one carbon atom.

The substituent is preferably a monovalent substituent unless otherwise specified.

"Actinic rays" or "radiation" in the present specification means, for example, a bright line spectrum of a mercury lamp, far ultraviolet rays typified by an excimer laser, extreme ultraviolet rays (EUV light), X-rays, electron beams (EB), or the like. "Light" in the present specification means actinic rays or radiation.

Unless otherwise specified, "exposure" in the present specification encompasses not only exposure by a bright line spectrum of a mercury lamp, far ultraviolet rays typified by an excimer laser, extreme ultraviolet rays, X-rays (EUV light), or the like, but also lithography by particle beams such as electron beams and ion beams.

In the present specification, a numerical range expressed using "to" is used in a meaning of a range that includes the preceding and succeeding numerical values of "to" as the lower limit value and the upper limit value, respectively.

The bonding direction of divalent groups cited in the present specification is not limited unless otherwise specified. For example, in a case where Y in a compound represented by General Formula "X—Y—Z" is —COO—, Y may be —CO—O— or —O—CO—. In addition, the compound may be "X—CO—O—Z" or "X—O—CO—Z".

In the present specification, (meth)acrylate represents acrylate and methacrylate, and (meth)acryl represents acryl and methacryl.

In the present specification, a weight-average molecular weight (Mw), a number-average molecular weight (Mn), and a dispersity (also referred to as a molecular weight distribution) (Mw/Mn) of a resin are defined as values expressed in terms of polystyrene by means of gel permeation chromatography (GPC) measurement (solvent: tetrahydrofuran, flow amount (amount of a sample injected): 10 L, columns: TSK gel Multipore HXL-M manufactured by Tosoh Corporation, column temperature: 40° C., flow rate: 1.0 mL/min, and detector: differential refractive index detector) using a GPC apparatus (HLC-8120GPC manufactured by Tosoh Corporation).

In the present specification, an acid dissociation constant (pKa) represents an acid dissociation constant (pKa) in an aqueous solution, and is specifically a value determined by computation from a value based on a Hammett's substituent constant and database of publicly known literature values, using the following software package 1. Any of the values of the acid dissociation constants (pKa) described in the present specification indicate values determined by computation using the software package.

Software Package 1: Advanced Chemistry Development (ACD/Labs) Software V 8.14 for Solaris (1994-2007 ACD/Labs).

On the other hand, the acid dissociation constant (pKa) can also be determined by a molecular orbital computation method. Examples of a specific method therefor include a method for performing calculation by computing $H^+$ dissociation free energy, in an aqueous solution based on a thermodynamic cycle. With regard to a computation method for $H^+$ dissociation free energy, the $H^+$ dissociation free energy can be calculated by, for example, density functional theory (DFT), but various other methods have been reported in literature and the like, and are not limited thereto. Furthermore, there are a plurality of software applications capable of performing DFT, and examples thereof include Gaussian 16.

As described above, the acid dissociation constant (pKa) in the present specification refers to a value determined by computation from a value based on a Hammett's substituent constant and database of publicly known literature values, using the software package 1, but in a case where the acid dissociation constant (pKa) cannot be calculated by the method, a value obtained by Gaussian 16 based on density functional theory (DFT) shall be adopted.

In addition, the acid dissociation constant (pKa) in the present specification refers to an "acid dissociation constant (pKa) in an aqueous solution" as described above, but in a case where the acid dissociation constant (pKa) in an aqueous solution cannot be calculated, an "acid dissociation constant (pKa) in a dimethyl sulfoxide (DMSO) solution" shall be adopted.

In the present specification, examples of the halogen atom include a fluorine atom, a chlorine atom, a bromine atom, and an iodine atom.

[Method for Producing Actinic Ray-Sensitive or Radiation-Sensitive Resin Composition]

The method for producing an actinic ray-sensitive or radiation-sensitive resin composition of an embodiment of the present invention (hereinafter also referred to as "the production method of the embodiment of the present invention") relates to a method for producing an actinic ray-sensitive or radiation-sensitive resin composition (hereinafter also referred to as a "resist composition") including at least a resin having a polarity that increases due to decomposition by the action of an acid (hereinafter an "acid-decomposable resin" or a "resin (A)"), a compound that generates an acid upon irradiation with actinic rays or radiation (hereinafter also referred to as a "photoacid generator"), and a solvent.

As a first feature of the production method of the embodiment of the present invention, an aspect in which the photoacid generator includes one or more photoacid generators selected from the group consisting of compounds (I) to (III) which will be described later (hereinafter also referred to as a "specific photoacid generator") may be mentioned. In addition, as a second feature of the production method of the embodiment of the present invention, an aspect in which in a case of producing a resist composition, first, a first solution including an acid-decomposable resin and a first solvent is prepared, and the first solution is mixed with a specific photoacid generator may be mentioned.

Recently, the present inventors have clarified that photoacid generators including polyvalent salt structures (for example, divalent salt structures) in the molecule are easily aggregated with each other due to the salt structures in a resist composition in the same manner as with the photoacid generator represented by General Formula (I) used in JP2015-024989A, and as a result, many defects are generated during pattern formation.

The present inventors have conducted intensive studies on the findings, and have thus found that it is possible to suppress the occurrence of defects of a pattern formed, in a case of using a production method for preparing a resist composition, in which a polymer solution (first solution) including an acid-decomposable resin and a solvent (first solvent) in advance is prepared and this polymer solution (first solution) is mixed with a specific photoacid generator as a photoacid generator including a polyvalent salt structure in the molecule.

Mechanism of action thereof is not clear, but it is presumed that in a case where a polymer solution including an acid-decomposable resin and a solvent is mixed with specific photoacid generators, the specific photoacid generators have a solubility in the solvent that increases by the action of the acid-decomposable resin, and as a result, the formation of aggregates between the specific photoacid generators is suppressed. This is also clear from the section of Examples of the present specification. That is, for example, referring to Table 1 and Table 6, it is also clear that desired results could not be obtained in the suppression of defects in Comparative Example 1 in which a resist composition was prepared by directly mixing an acid-decomposable resin, specific photoacid generators, and a solvent, and Comparative Example 2 in which a resist composition was prepared by directly mixing a solution having a specific photoacid generators dissolved in a solvent in advance with an acid-decomposable resin.

Furthermore, as will be described later, it is confirmed that the performance of suppressing defects of a pattern formed is more excellent in a case of using a production method in which a solution (second solution) having a specific photoacid generator dissolved in a solvent having a higher SP (second solvent) value than the first solvent is prepared in advance, and the second solution is mixed with the first solution to prepare a resist composition.

Moreover, as will be described later, it is confirmed that the performance of suppressing defects of a pattern formed is more excellent in a case of using a production method in which a concentration of solid contents of the first solution is set to 5.0% to 20.0% by mass, and a third solution obtained by mixing the first solution and the second solution is further mixed with the first solvent included in the first solution to prepare a resist composition.

In addition, as will be described later, it is confirmed that the performance of suppressing defects of a pattern formed is more excellent in a case of using a production method in which an SP value of the first solvent included in the first solution is set to less than 18.5 $MPa^{1/2}$, and an SP value of the second solvent included in the second solution is set to 18.5 $MPa^{1/2}$ or more to prepare a resist composition.

Hereinbelow, a resist composition that can be prepared by the production method of the embodiment of the present invention will first be described, and the procedure of the production method of the embodiment of the present invention will then be described.

[Resist Composition]

A resist composition (hereinafter also referred to as a "specific resist composition") that can be prepared by the production method of the embodiment of the present invention includes at least a photoacid generator including a specific photoacid generator, an acid-decomposable resin (resin (A)), and a solvent.

The specific resist composition may be either a positive tone resist composition or a negative tone resist composition. In addition, the resist composition may be either a resist composition for alkaline development or a resist composition for organic solvent development.

The specific resist composition is typically a chemically amplified resist composition.

Hereinbelow, first, various components of the specific resist composition will be described in detail.

<Photoacid Generator>

The specific resist composition includes a compound that generates an acid upon irradiation with actinic rays or radiation (photoacid generator).

A content of the photoacid generator (a total content of the photoacid generators in a case where a plurality of kinds of the photoacid generators are present) in the specific resist composition is preferably 5.0% to 25.0% by mass, and more preferably 8.0% to 20.0% by mass with respect to a total solid content of the composition. The content of the photoacid generator as mentioned herein is intended to be, for example, a total content (% by mass) of a specific photoacid generator which will be described later and a photoacid generator which will be described later in a case where two kinds of photoacid generators, that is, the specific photoacid generator and another photoacid generator other than the specific photoacid generator are included in the specific resist composition.

Furthermore, in the present specification, a "solid content" in the resist composition is intended to be a component forming a resist film, and does not include a solvent. In addition, any of components that form a resist film are regarded as a solid content even in a case where they have a property and a state of a liquid.

The photoacid generator includes a compound selected from the group consisting of compounds (I) to (III) which will be described later (specific photoacid generator).

A content of the specific photoacid generator (a total content of the specific photoacid generators in a case where a plurality of kinds of the specific photoacid generators are included) is preferably 5.0% to 25.0% by mass, and more preferably 8.0% to 20.0% by mass with respect to the total solid content of the composition.

The specific photoacid generators may be used alone or in combination of two or more kinds thereof.

Hereinafter, the specific photoacid generator and other photoacid generators will be described.

(Specific Photoacid Generator)

The specific photoacid generator is a compound selected from the group consisting of compounds (I) to (III) which will be described later. Hereinafter, each of the compounds (I) to (III) will be described.

<<Compound (I)>>

The compound (I) will be described below.

Compound (I): a compound having each one of the following structural moiety X and the following structural moiety Y, the compound generating an acid including the following first acidic moiety derived from the following structural moiety X and the following second acidic moiety derived from the following structural moiety Y upon irradiation with actinic rays or radiation Structural moiety X: a structural moiety which consists of an anionic moiety $A_1^-$ and a cationic moiety $M_1^+$, and forms a first acidic moiety represented by $HA_2$ upon irradiation with actinic rays or radiation Structural moiety Y: a structural moiety which consists of an anionic moiety $A_2^-$ and a cationic moiety $M_2^+$, and forms a second acidic moiety represented by $HA_2$, having a structure different from that of the first acidic moiety formed by the structural moiety X, upon irradiation with actinic rays or radiation It should be noted that the compound (I) satisfies the following condition I.

Condition I: a compound PI formed by substituting the cationic moiety $M_1^+$ in the structural moiety X and the cationic moiety $M_2^+$ in the structural moiety Y with $H^+$ in the compound (I) has an acid dissociation constant a1 derived from an acidic moiety represented by $HA_1$, formed by substituting the cationic moiety $M_1^+$ in the structural moiety X with $H^+$, and an acid dissociation constant a2 derived from an acidic moiety represented by $HA_2$, formed by substituting the cationic moiety $M_2^+$ in the structural moiety Y with $H^+$, and the acid dissociation constant a2 is larger than the acid dissociation constant a1.

Furthermore, the acid dissociation constant a1 and the acid dissociation constant a2 are determined by the above-mentioned method. More specifically, with regard to the acid dissociation constant a1 and the acid dissociation constant a2 of the compound PI, in a case where the acid dissociation constant of the compound PI is determined, the pKa with which the compound PT (in which the compound PT corresponds to a "compound having $HA_1$ and $HA_2$") serves as a "compound having $A_1^-$ and $HA_2$" is the acid dissociation constant a1, and the pKa with which "compound having $A_1^-$ and $HA_2$" serves as a "compound having $A_1^-$ and $A_2^-$" is the acid dissociation constant a2.

In addition, the compound PI corresponds to an acid generated by irradiating the compound (I) with actinic rays or radiation.

From the viewpoint that the LWR performance of a pattern formed is more excellent, the difference between the acid dissociation constant a1 and the acid dissociation constant a2 in the compound PI is preferably 2.0 or more, and more preferably 3.0 or more. Furthermore, the upper limit value of the difference between the acid dissociation constant a1 and the acid dissociation constant a2 is not particularly limited, but is, for example, 15.0 or less.

In addition, for the compound PI, the acid dissociation constant a2 is, for example, 6.5 or less, and from the viewpoint that the stability of the cationic moiety of the compound (I) in the resist composition is more excellent, the acid dissociation constant a2 is preferably 2.0 or less, and more preferably 1.0 or less. Furthermore, a lower limit value of the acid dissociation constant a2 is, for example, −3.5 or more, and preferably −2.0 or more.

In addition, from the viewpoint that the LWR performance of a pattern formed is more excellent, the acid dissociation constant a1 is preferably 2.0 or less, more preferably 0.5 or less, and still more preferably −0.1 or less in the compound PI. Furthermore, a lower limit value of the acid dissociation constant a1 is preferably −15.0 or more.

The compound (I) is not particularly limited, and examples thereof include a compound represented by General Formula (Ia).

$$M_{11}^+A_{11}^--L_1-A_{12}-M_{12}^+ \tag{Ia}$$

In General Formula (Ia), "$M_{11}^+A_{11}^-$" and "$A_{12}^-M_{12}^+$" correspond to the structural moiety X and the structural moiety Y, respectively. The compound (Ia) generates an acid represented by $HA_{11}-L_1-A_{21}H$ upon irradiation with actinic rays or radiation. That is, "$M_{11}^+A_{11}^-$" forms a first acidic moiety represented by $HA_{11}$, and "$A_{12}^-M_{12}^+$" forms a second acidic moiety represented by $HA_{12}$, which has a structure different from that of the first acidic moiety.

In General Formula (Ia), $M_{11}^+$ and $M_{12}^+$ each independently represent an organic cation.

$A_{11}^-$ and $A_{12}^-$ each independently represent an anionic functional group. It should be noted that $A_{12}^-$ represents a structure different from that of the anionic functional group represented by $A_{11}^-$.

$L_1$ represents a divalent linking group.

It should be noted that in the compound PIa ($HA_{11}-L_1-A_{12}H$) formed by substituting organic cations represented by $M_{11}^+$ and $M_{12}^+$ with $H^+$ in General Formula (Ia), the acid dissociation constant a2 derived from the acidic moiety represented by $A_{12}H$ is larger than the acid dissociation constant a1 derived from the acidic moiety represented by $HA_{11}$. Furthermore, suitable values of the acid dissociation constant a1 and the acid dissociation constant a2 are as described above.

The organic cations represented by $M_{11}^+$ and $M_{12}^+$ in General Formula (Ia) are as described later.

Examples of the anionic functional group represented by $A_{11}^-$ and $A_{12}^-$ include groups represented by General Formulae (B-1) to (B-13).

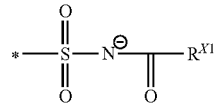

B-1

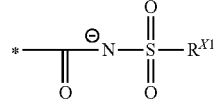

B-2

-continued

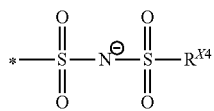
B-3

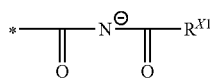
B-4

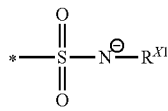
B-5

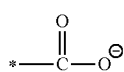
B-6

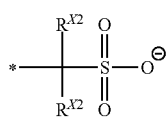
B-7

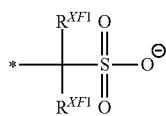
B-8

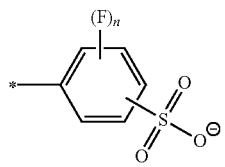
B-9

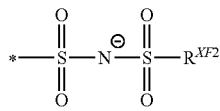
B-10

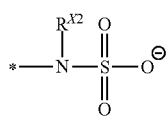
B-11

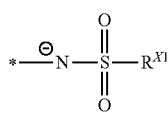
B-12

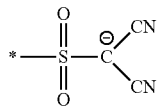
B-13

In General Formulae (B-1), (B-2), (B-4), (B-5), and (B-12), $R^{X1}$ represents a substituent.

As $R^{X1}$, a linear, branched, or cyclic alkyl group is preferable.

The alkyl group preferably has 1 to 15 carbon atoms, and more preferably has 1 to 10 carbon atoms.

The alkyl group may have a substituent. As the substituent, a fluorine atom or a cyano group is preferable. In a case where the alkyl group has a fluorine atom as the substituent, it may be a perfluoroalkyl group.

In addition, the alkyl group may have a carbon atom substituted with a carbonyl group.

In General Formula (B-3), $R^{X4}$ represents a substituent.

As $R^{X4}$, a linear, branched, or cyclic alkyl group is preferable.

The alkyl group preferably has 1 to 15 carbon atoms, and more preferably has 1 to 10 carbon atoms.

The alkyl group may have a substituent. As the substituent, a fluorine atom or a cyano group is preferable. Furthermore, in a case where $R^{X4}$ is an alkyl group having a fluorine atom as the substituent, it is preferable that $R^{X4}$ is not a perfluoroalkyl group.

In addition, the alkyl group may have a carbon atom substituted with a carbonyl group.

In General Formulae (B-7) and (B-11), $R^{X2}$ represents a hydrogen atom, or a substituent other than a fluorine atom and a perfluoroalkyl group.

As the substituent other than a fluorine atom and a perfluoroalkyl group, represented by $R^{X2}$, a linear, branched, or cyclic alkyl group is preferable.

The alkyl group preferably has 1 to 15 carbon atoms, and more preferably has 1 to 10 carbon atoms.

The alkyl group may have a substituent other than a fluorine atom.

In General Formula (B-8), $R^{XF2}$ represents a hydrogen atom, a fluorine atom, or a perfluoroalkyl group. It should be noted that at least one of the plurality of $R^{XF1}$'s represents a fluorine atom or a perfluoroalkyl group.

The perfluoroalkyl group represented by $R^{XF1}$ preferably has 1 to 15 carbon atoms, more preferably has 1 to 10 carbon atoms, and still more preferably has 1 to 6 carbon atoms.

In General Formula (B-10), $R^{XF2}$ represents a fluorine atom or a perfluoroalkyl group. The perfluoroalkyl group represented by $R^{XF2}$ preferably has 1 to 15 carbon atoms, more preferably has 1 to 10 carbon atoms, and still more preferably has 1 to 6 carbon atoms.

In General Formula (B-9), n represents an integer of 0 to 4.

A combination of the anionic functional groups represented by $A_{11}^-$ and $A_{12}^-$ is not particularly limited, but for example, in a case where $A_{11}^-$ is a group represented by General Formula (B-8) or (B-10), examples of the anionic functional group represented by $A_{12}^-$ include a group represented by General Formula (B-1) to (B-7), (B-9), or (B-11) to (B-13); and in a case where $A_{11}^-$ is a group represented by General Formula (B-7), examples of the anionic functional group represented by $A_{12}^-$ includes a group represented by General Formula (B-6).

In General Formula (Ta), the divalent linking group represented by $L_1$ is not particularly limited, and examples thereof include —CO—, —NR—, —CO—, —O—, an alkylene group (which preferably has 1 to 6 carbon atoms, and may be linear or branched), a cycloalkylene group (preferably having 3 to 15 carbon atoms), an alkenylene group (preferably having 2 to 6 carbon atoms), a divalent aliphatic heterocyclic group (preferably a 5- to 10-membered ring, more preferably a 5- to 7-membered ring, and still more preferably a 5- or 6-membered ring, each having at least one of an N atom, an O atom, an S atom, or an Se atom in the ring structure), and a divalent linking group formed by combination of a plurality of these groups. Examples of R include a hydrogen atom or a monovalent substituent. The monovalent substituent is not particularly limited, but is preferably for example, an alkyl group (preferably having 1 to 6 carbon atoms).

The divalent linking group may further include a group selected from the group consisting of —S—, —SO—, and —SO$_2$—.

In addition, the alkylene group, the cycloalkylene group, the alkenylene group, and the divalent aliphatic heterocyclic group may be substituted with a substituent. Examples of the substituent include a halogen atom (preferably a fluorine atom).

In General Formula (Ia), preferred forms of the organic cations represented by $M_{11}^+$ and $M_{12}^+$ will be described in detail.

The organic cations represented by $M_{11}^+$ and $M_{12}^+$ are each independently preferably an organic cation represented by General Formula (ZaI) (cation (ZaI)) or an organic cation represented by General Formula (ZaII) (cation (ZaII)).

In General Formula (ZaI), $R^{201}$, $R^{202}$, and $R^{203}$ each independently represent an organic group.

The organic group as each of $R^{201}$, $R^{202}$, and $R^{203}$ usually has 1 to 30 carbon atoms, and preferably has 1 to 20 carbon atoms. In addition, two of $R^{201}$ to $R^{203}$ may be bonded to each other to form a ring structure, and the ring may include an oxygen atom, a sulfur atom, an ester group, an amide group, or a carbonyl group. Examples of the group formed by the bonding of two of $R^{201}$ to $R^{203}$ include an alkylene group (for example, a butylene group and a pentylene group), and —CH$_2$—CH$_2$—O—CH$_2$—CH$_2$—.

Suitable aspects of the organic cation as General Formula (ZaI) include a cation (ZaI-1), a cation (ZaI-2), an organic cation represented by General Formula (ZaI-3b) (cation (ZaI-3b)), and an organic cation represented by General Formula (ZaI-4b) (cation (ZaI-4b)), each of which will be described later.

First, the cation (ZaI-1) will be described.

The cation (ZaI-1) is an arylsulfonium cation in which at least one of $R^{201}$, $R^{202}$, or $R^{203}$ of General Formula (ZaI) is an aryl group.

In the arylsulfonium cation, all of $R^{201}$ to $R^{203}$ may be aryl groups, or some of $R^{201}$ to $R^{203}$ may be an aryl group, and the rest may be an alkyl group or a cycloalkyl group.

In addition, one of $R^{201}$ to $R^{203}$ may be an aryl group, two of $R^{201}$ to $R^{203}$ may be bonded to each other to form a ring structure, and an oxygen atom, a sulfur atom, an ester group, an amide group, or a carbonyl group may be included in the ring. Examples of the group formed by the bonding of two of $R^{201}$ to $R^{203}$ include an alkylene group (for example, a butylene group, a pentylene group, or —CH$_2$—CH$_2$—O—CH$_2$—CH$_2$—) in which one or more methylene groups may be substituted with an oxygen atom, a sulfur atom, an ester group, an amide group, and/or a carbonyl group.

Examples of the arylsulfonium cation include a triarylsulfonium cation, a diarylalkylsulfonium cation, an aryldialkylsulfonium cation, a diarylcycloalkylsulfonium cation, and an aryldicycloalkylsulfonium cation.

As the aryl group included in the arylsulfonium cation, a phenyl group or a naphthyl group is preferable, and the phenyl group is more preferable. The aryl group may be an aryl group which has a heterocyclic structure having an oxygen atom, a nitrogen atom, a sulfur atom, or the like. Examples of the heterocyclic structure include a pyrrole residue, a furan residue, a thiophene residue, an indole residue, a benzofuran residue, and a benzothiophene residue. In a case where the arylsulfonium cation has two or more aryl groups, the two or more aryl groups may be the same as or different from each other.

The alkyl group or the cycloalkyl group contained in the arylsulfonium cation, as necessary, is preferably a linear alkyl group having 1 to 15 carbon atoms, a branched alkyl group having 3 to 15 carbon atoms, or a cycloalkyl group having 3 to 15 carbon atoms, and examples thereof include a methyl group, an ethyl group, a propyl group, an n-butyl group, a sec-butyl group, a t-butyl group, a cyclopropyl group, a cyclobutyl group, and a cyclohexyl group.

Examples of the substituent which may be contained in each of the aryl group, the alkyl group, and the cycloalkyl group of each of $R^{201}$ to $R^{203}$ each independently include an alkyl group (for example, having 1 to 15 carbon atoms), a cycloalkyl group (for example, having 3 to 15 carbon atoms), an aryl group (for example, having 6 to 14 carbon atoms), an alkoxy group (for example, having 1 to 15 carbon atoms), a cycloalkylalkoxy group (for example, having 1 to 15 carbon atoms), a halogen atom, a hydroxyl group, and a phenylthio group.

The substituent may further have a substituent as possible, and may be in the form of an alkyl halide group such as a trifluoromethyl group, for example, in which the alkyl group has a halogen atom as a substituent.

Next, the cation (ZaI-2) will be described.

The cation (ZaI-2) is a cation in which $R^{201}$ to $R^{203}$ in Formula (ZaI) are each independently a cation representing an organic group having no aromatic ring. Here, the aromatic ring also encompasses an aromatic ring including a heteroatom.

The organic group having no aromatic ring as each of $R^{201}$ to $R^{203}$ generally has 1 to 30 carbon atoms, and preferably 1 to 20 carbon atoms.

$R^{201}$ to $R^{203}$ are each independently preferably an alkyl group, a cycloalkyl group, an allyl group, or a vinyl group, more preferably a linear or branched 2-oxoalkyl group, a 2-oxocycloalkyl group, or an alkoxycarbonylmethyl group, and still more preferably the linear or branched 2-oxoalkyl group.

Examples of the alkyl group and the cycloalkyl group of each of $R^{201}$ to $R^{203}$ include a linear alkyl group having 1 to 10 carbon atoms or branched alkyl group having 3 to 10 carbon atoms (for example, a methyl group, an ethyl group, a propyl group, a butyl group, and a pentyl group), and a cycloalkyl group having 3 to 10 carbon atoms (for example, a cyclopentyl group, a cyclohexyl group, and a norbornyl group).

$R^{201}$ to $R^{203}$ may further be substituted with a halogen atom, an alkoxy group (for example, having 1 to 5 carbon atoms), a hydroxyl group, a cyano group, or a nitro group.

Next, the cation (ZaI-3b) will be described.

The cation (ZaI-3b) is a cation represented by General Formula (ZaI-3b).

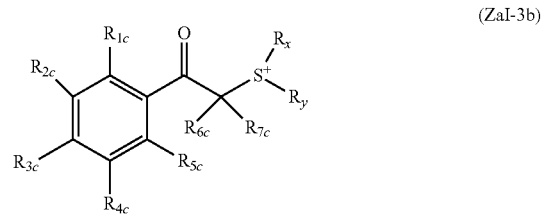

In General Formula (ZaI-3b), $R_{1c}$ to $R_{5c}$ each independently represent a hydrogen atom, an alkyl group, a cycloalkyl group, an aryl group, an alkoxy group, an aryloxy group, an alkoxycarbonyl group, an alkylcarbonyloxy group, a cycloalkylcarbonyloxy group, a halogen atom, a hydroxyl group, a nitro group, an alkylthio group, or an arylthio group.

$R_{6c}$ and $R_{7c}$ each independently represent a hydrogen atom, an alkyl group (a t-butyl group or the like), a cycloalkyl group, a halogen atom, a cyano group, or an aryl group.

$R_x$ and $R_y$ each independently represent an alkyl group, a cycloalkyl group, a 2-oxoalkyl group, a 2-oxocycloalkyl group, an alkoxycarbonylalkyl group, an allyl group, or a vinyl group.

Any two or more of $R_{1c}$ to $R_{5c}$, $R_{5c}$ and $R_{6c}$, $R_{6c}$ and $R_{7c}$, $R_{5c}$ and $R_x$, and $R_x$ and $R_y$ may each be bonded to each other to form a ring, and the ring may each independently include an oxygen atom, a sulfur atom, a ketone group, an ester bond, or an amide bond.

Examples of the ring include an aromatic or non-aromatic hydrocarbon ring, an aromatic or non-aromatic heterocyclic ring, and a polycyclic fused ring formed by combination of two or more of these rings. Examples of the ring include a 3- to 10-membered ring, and the ring is preferably a 4- to 8-membered ring, and more preferably a 5- or 6-membered ring.

Examples of the group formed by the bonding of any two or more of $R_{1c}, \ldots,$ or $R_{5c}$, $R_{6c}$ and $R_{7c}$, and $R_x$ and $R_y$ include an alkylene group such as a butylene group and a pentylene group. The methylene group in this alkylene group may be substituted with a heteroatom such as an oxygen atom.

As the group formed by the bonding of $R_{5c}$ and $R_{6c}$, and $R_{5c}$ and $R_x$, a single bond or an alkylene group is preferable. Examples of the alkylene group include a methylene group and an ethylene group.

Next, the cation (ZaI-4b) will be described.

The cation (ZaI-4b) is a cation represented by General Formula (ZaI-4b).

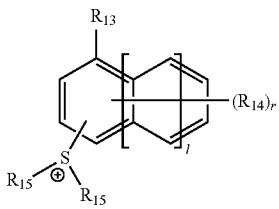

(ZaI-4b)

In General Formula (ZaI-4b), l represents an integer of 0 to 2.

r represents an integer of 0 to 8.

$R_{13}$ represents a hydrogen atom, a fluorine atom, a hydroxyl group, an alkyl group, an alkoxy group, an alkoxycarbonyl group, or a group having a cycloalkyl group (which may be the cycloalkyl group itself or a group including the cycloalkyl group in a part thereof). These groups may have a substituent.

$R_{14}$ represents a hydroxyl group, an alkyl group, an alkoxy group, an alkoxycarbonyl group, an alkylcarbonyl group, an alkylsulfonyl group, a cycloalkylsulfonyl group, or a group having a cycloalkyl group (which may be the cycloalkyl group itself or a group including the cycloalkyl group in a part thereof). These groups may have a substitu-ent. In a case where $R_{14}$'s are present in a plural number, $R_{14}$'s each independently represent the group such as a hydroxyl group.

$R_{15}$'s each independently represent an alkyl group, a cycloalkyl group, or a naphthyl group. These groups may have a substituent. Two $R_{15}$'s may be bonded to each other to form a ring. In a case where two $R_{15}$'s are bonded to each other to form a ring, the ring skeleton may include a heteroatom such as an oxygen atom and a nitrogen atom. In one aspect, it is preferable that two $R_{15}$'s are alkylene groups and are bonded to each other to form a ring structure.

In General Formula (ZaI-4b), the alkyl groups of each of $R_{13}$, $R_{14}$, and $R_{15}$ are linear or branched. The alkyl group preferably has 1 to 10 carbon atoms. As the alkyl group, a methyl group, an ethyl group, an n-butyl group, a t-butyl group, or the like is more preferable.

Next, General Formula (ZaII) will be described.

In General Formula (ZaII), $R^{204}$ and $R^{205}$ each independently represent an aryl group, an alkyl group, or a cycloalkyl group.

As the aryl group of each of $R^{204}$ and $R^{205}$, a phenyl group or a naphthyl group is preferable, and the phenyl group is more preferable. The aryl group of each of $R^{204}$ and $R^{205}$ may be an aryl group which has a heterocyclic ring having an oxygen atom, a nitrogen atom, a sulfur atom, or the like. Examples of the skeleton of the aryl group having a heterocyclic ring include pyrrole, furan, thiophene, indole, benzofuran, and benzothiophene.

As the alkyl group and the cycloalkyl group of each of $R^{204}$ and $R^{205}$, a linear alkyl group having 1 to 10 carbon atoms or a branched alkyl group having 3 to 10 carbon atoms (for example, a methyl group, an ethyl group, a propyl group, a butyl group, and a pentyl group), or a cycloalkyl group having 3 to 10 carbon atoms (for example, a cyclopentyl group, a cyclohexyl group, and a norbornyl group) is preferable.

The aryl group, the alkyl group, and the cycloalkyl group of each of $R^{204}$ and $R^{205}$ may each independently have a substituent. Examples of the substituent which may be contained in each of the aryl group, the alkyl group, and the cycloalkyl group of each of $R^{204}$ and $R^{205}$ include an alkyl group (for example, having 1 to 15 carbon atoms), a cycloalkyl group (for example, having 3 to 15 carbon atoms), an aryl group (for example, having 6 to 15 carbon atoms), an alkoxy group (for example, having 1 to 15 carbon atoms), a halogen atom, a hydroxyl group, and a phenylthio group.

<<Compound (II)>>

Next, the compound (II) will be described.

Compound (II): a compound having the two or more structural moieties X and the structural moiety Y, the compound generating an acid including the two or more first acidic moieties derived from the structural moieties X and the second acidic moiety derived from the structural moiety Y upon irradiation with actinic rays or radiation It should be noted that the compound (II) satisfies the following condition II.

Condition II: a compound PII formed by substituting the cationic moiety $M_1^+$ in the structural moiety X and the cationic moiety $M_2^+$ in the structural moiety Y with $H^+$ in the compound (II) has an acid dissociation constant a1 derived from an acidic moiety represented by $HA_1$, formed by substituting the cationic moiety $M_1^+$ in the structural moiety X with $H^+$ and an acid dissociation constant a2 derived from an acidic moiety represented by $HA_2$, formed by substituting the cationic moiety $M_2^+$ in the structural moiety Y with $H^+$, and the acid dissociation constant a2 is larger than the acid dissociation constant a1.

The acid dissociation constant a1 and the acid dissociation constant a2 are determined by the above-mentioned method.

Here, the acid dissociation constant a1 and the acid dissociation constant a2 of the compound PII will be more specifically described. In a case where the compound (II) is, for example, a compound that generates an acid having two of the first acidic moieties derived from the structural moiety X and one of the second acidic moieties derived from the structural moiety Y, the compound PII corresponds to a "compound having two $HA_1$'s and $HA_2$". In a case where the acid dissociation constant of the compound PII was determined, the pKa in a case where the compound PII serves as a "compound having one $A_1^-$, one $HA_1$, and $HA_2$" is the acid dissociation constant a1, and the pKa in a case where the compound having two $A_1^-$'s and $HA_2$ serves as a "compound having two $A_1^-$'s and $A_2^-$" is the acid dissociation constant a2. That is, in a case where the compound PII has a plurality of acid dissociation constants derived from the acidic moiety represented by $HA_1$, formed by substituting the cationic moiety $M_1^+$ in the structural moiety X with $H^+$, the smallest value is considered as the acid dissociation constant a1.

In addition, the compound PII corresponds to an acid generated by irradiating the compound (II) with actinic rays or radiation.

Furthermore, the compound (II) may have a plurality of the structural moieties Y.

From the viewpoint that the LWR performance of a pattern formed is more excellent, in the compound PII, the difference between the acid dissociation constant a1 and the acid dissociation constant a2 is preferably 2.0 or more, and more preferably 3.0 or more. Furthermore, the upper limit value of the difference between the acid dissociation constant a1 and the acid dissociation constant a2 is not particularly limited, but is, for example, 15.0 or less.

In addition, in the compound PII, the acid dissociation constant a2 is, for example, 6.5 or less, and from the viewpoint that the stability of the cationic moiety of the compound (I) in the resist composition is more excellent, the acid dissociation constant a2 is preferably 2.0 or less, and more preferably 1.0 or less. Furthermore, a lower limit value of the acid dissociation constant a2 is, for example, −3.5 or more, and preferably −2.0 or more.

In addition, from the viewpoint that the LWR performance of a pattern formed is more excellent, in the compound PII, the acid dissociation constant a1 is preferably 2.0 or less, more preferably 0.5 or less, and still more preferably −0.1 or less. Furthermore, a lower limit value of the acid dissociation constant a1 is preferably −15.0 or more.

The compound (II) is not particularly limited, and examples thereof include a compound represented by General Formula (IIa).

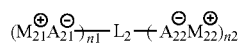
(IIa)

In General Formula (Ia), "$M_{21}^+A_{21}^-$" and "$A_{22}^-M_{22}^+$" correspond to the structural moiety X and the structural moiety Y, respectively. The compound (IIa) generates an acid represented by General Formula (IIa-1) upon irradiation with actinic rays or radiation. That is, "$M_{21}^+A_{21}^-$" forms a first acidic moiety represented by $HA_{21}$, and "$A_{22}^-M_{22}^+$" forms a second acidic moiety represented by $HA_{22}$ having a structure different from that of the first acidic moiety.

(IIa-1)

In General Formula (IIa), $M_{21}^+$ and $M_{22}^+$ each independently represent an organic cation.

$A_{21}^-$ and $A_{22}^-$ each independently represent an anionic functional group. It should be noted that $A_{22}^-$ represents a structure different from the anionic functional group represented by $A_{21}^-$.

$L_2$ represents a (n1+n2) valent organic group.

n1 represents an integer of 2 or more.

n2 represents an integer of 1 or more.

It should be noted that in the compound PIIa (corresponding to a compound represented by General Formula (IIA-1)), formed by substituting organic cations represented by $M_{21}^+$ and $M_{22}^+$ with $H^+$ in General Formula (IIa), the acid dissociation constant a2 derived from the acidic moiety represented by $A_{22}II$ is larger than the acid dissociation constant a1 derived from the acidic moiety represented by $HA_{21}$. Furthermore, suitable values of the acid dissociation constant a1 and the acid dissociation constant a2 are as described above.

In General Formula (IIa), $M_{21}^+$, $M_{22}^+$, $A_{21}^-$, and $A_{22}^-$ have the same definitions as $M_{11}^+$, $M_{12}^+$, $A_{11}^-$, and $A_{12}^-$ in General Formula (Ia), respectively, and suitable aspects thereof are also the same.

In General Formula (IIa), n1 pieces of $M_{21}^+$ and n1 pieces of $A_{21}^+$ represent the same group as each other.

In General Formula (IIa), the (n1+n2)-valent organic group represented by $L_2$ is not particularly limited, and examples thereof include groups represented by (A1) and (A2) below. Furthermore, in (A1) and (A2) below, at least two of *'s represent bonding positions to A21, and at least one of *'s represents a bonding position to $A_{22}^-$.

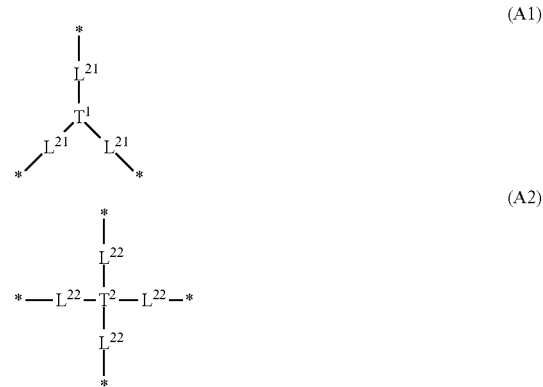

In (A1) and (A2) above, $T^1$ represents a trivalent hydrocarbon ring group or a trivalent heterocyclic group, and $T^2$ represents a carbon atom, a tetravalent hydrocarbon ring group, or a tetravalent heterocyclic group.

The hydrocarbon ring group may be an aromatic hydrocarbon ring group or an aliphatic hydrocarbon ring group. The number of carbon atoms included in the hydrocarbon ring group is preferably 6 to 18, and more preferably 6 to 14.

The heterocyclic group may be either an aromatic heterocyclic group or an aliphatic heterocyclic group. The heterocyclic ring is preferably a 5- to 10-membered ring, more preferably a 5- to 7-membered ring, and still more preferably a 5- or 6-membered ring, each of which has at least one N atom, O atom, S atom, or Se atom in the ring structure.

In addition, in (A1) and (A2), $L^{21}$ and $L^{22}$ each independently represent a single bond or a divalent linking group.

The divalent linking group represented by each of $L^{21}$ and $L^{22}$ has the same definition as the divalent linking group represented by $L_1$ in General Formula (Ia), and a suitable aspect thereof is also the same.

n1 represents an integer of 2 or more. An upper limit thereof is not particularly limited, but is, for example, 6 or less, preferably 4 or less, and more preferably 3 or less.

n2 represents an integer of 1 or more. An upper limit thereof is not particularly limited, but is, for example, 3 or less, and preferably 2 or less.

<<Compound (III)>>

Next, the compound (III) will be described.

Compound (III): a compound having the two or more structural moieties X and the following structural moiety Z, the compound generating an acid including the two or more first acidic moieties derived from the structural moieties X and the structural moiety Z upon irradiation with actinic rays or radiation Structural Moiety Z: A Nonionic Moiety Capable of Neutralizing an Acid The nonionic moiety capable of neutralizing an acid in the structural moiety Z is not particularly limited, examples thereof include organic moieties, with, for example, an organic moiety including a functional group having a group or electron capable of electrostatically interacting with a proton being preferable.

Examples of the functional group having a group or electron capable of electrostatically interacting with a proton include a functional group with a macrocyclic structure, such as a cyclic polyether, or a functional group having a nitrogen atom having an unshared electron pair not contributing to π-conjugation. The nitrogen atom having an unshared electron pair not contributing to π-conjugation is, for example, a nitrogen atom having a partial structure represented by the following formula.

Unshared electron pair

Examples of the partial structure of the functional group having a group or electron capable of electrostatically interacting with a proton include a crown ether structure, an azacrown ether structure, primary to tertiary amine structures, a pyridine structure, an imidazole structure, and a pyrazine structure, and among these, the primary to tertiary amine structures are preferable.

In the compound PIII formed by substituting the cationic moiety $M_1^+$ in the structural moiety X with $H^+$ in the compound (III), the acid dissociation constant a1 derived from the acidic moiety represented by $HA_1$, formed by substituting the cationic moiety $M_1^+$ in the structural moiety X with $H^+$, is preferably 2.0 or less, more preferably 0.5 or less, and still more preferably −0.1 or less, from the viewpoint that the LWR performance of a pattern formed is more excellent. Furthermore, a lower limit value of the acid dissociation constant a1 is preferably −15.0 or more.

Furthermore, in a case where the compound PIII has a plurality of acid dissociation constants derived from the acidic moiety represented by $HA_1$, formed by substituting the cationic moiety $M_1^+$ in the structural moiety X with $H^+$, the smallest value is considered as the acid dissociation constant a1.

That is, in a case where the compound (III) is, for example, a compound that generates an acid having two of the first acidic moieties derived from the structural moiety X and the structural moiety Z, the compound PIII corresponds to a "compound having two of $HA_1$". In a case where the acid dissociation constant of this compound PIII is determined, the pKa in a case where the compound PIII serves as a "compound having one of $A_1^-$ and one of $HA_1$" is the acid dissociation constant a1. That is, in a case where the compound PIII has a plurality of acid dissociation constants derived from the acidic moiety represented by $HA_1$, formed by substituting the cationic moiety $M_1^+$ in the structural moiety X with $H^+$, the smallest value is considered as the acid dissociation constant a1.

Furthermore, for example, in a case where the compound (III) is a compound represented by the compound (IIIa) which will be described later, the compound PIII formed by substituting the cationic moiety $M_1^+$ in the structural moiety X with $H^+$ in the compound (I11) corresponds to $HA_{31}$-$L_3$-$N(R^{2X})$-$L_4$-$A_{31}H$.

The compound (III) is not particularly limited, and examples thereof include a compound represented by General Formula (IIIa).

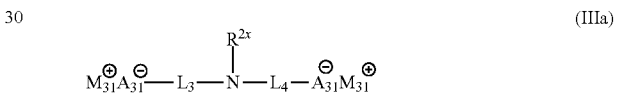

(IIIa)

In General Formula (IIIa), "$M_{31}^+A_{31}^-$" corresponds to the structural moiety X. The compound (IIIa) generates an acid represented by $HA_{31}$-$L_3$-$N(R^{2X})$-$L_4$-$A_{31}H$ upon irradiation with actinic rays or radiation. That is, "$M_{31}^+A_{31}^-$" forms the first acidic moiety represented by $HA_{31}$.

In General Formula (IIIa), $M_{31}^+$ represents an organic cation.

$A_{31}^-$ represents an anionic functional group.

$L_3$ and $L_4$ each independently represent a divalent linking group.

$R^{2X}$ represents a monovalent substituent.

In General Formula (IIIa), $M_{31}+$ and $A_{31}^-$ have the same definitions as $M_{11}^+$ and $A_{11}^-$ in General Formula (Ia), respectively, and suitable aspects thereof are also the same.

In General Formula (IIIa), $L_3$ and $L_4$ have the same definition as $L_1$ in General Formula (Ia), and suitable aspects thereof are also the same.

In General Formula (IIIa), two $M_{31}^+$'s and two $A_{31}^-$'s represent the same group as each other.

In General Formula (IIIa), the monovalent substituent represented by $R^{2X}$ is not particularly limited, and examples thereof include an alkyl group (which preferably has 1 to 10 carbon atoms, and may be linear or branched), a cycloalkyl group (preferably having 3 to 15 carbon atoms), and an alkenyl group (preferably having 2 to 6 carbon atoms), in which —$CH_2$— may be substituted with one or a combination of two or more selected from the group consisting of —CO—, —NH—, —O—, —S—, —SO—, and —$SO_2$—.

In addition, the alkylene group, the cycloalkylene group, and the alkenylene group may be substituted with a substituent.

The molecular weight of the compound represented by each of the compounds (I) to (III) are preferably 300 or more and less than 3,000, more preferably 500 to 2,000, and still more preferably 700 to 1,500.
Preferred examples of the compounds represented by the compounds (I) to (III) are shown below.
B-1
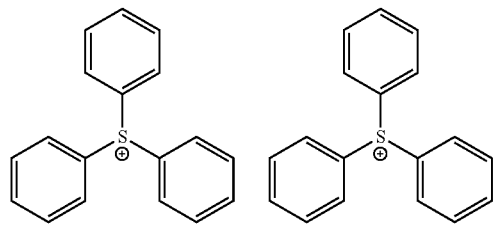
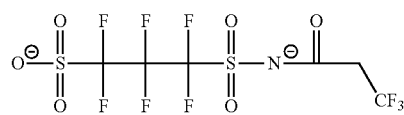
B-2
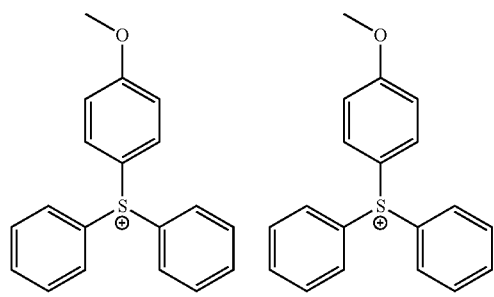
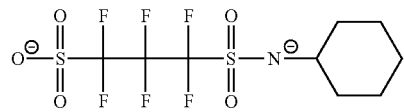
B-3
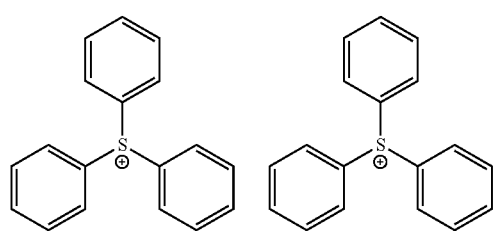
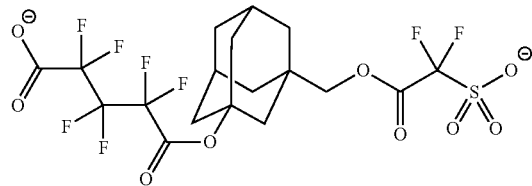
B-4
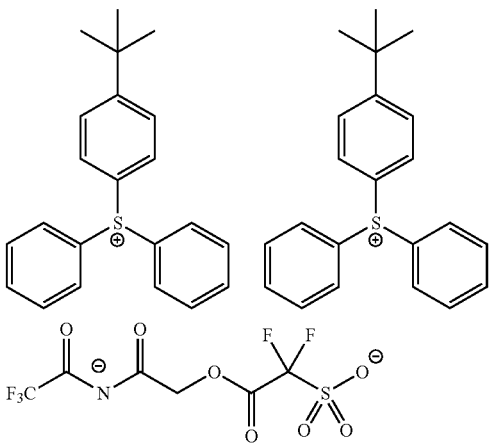
B-5
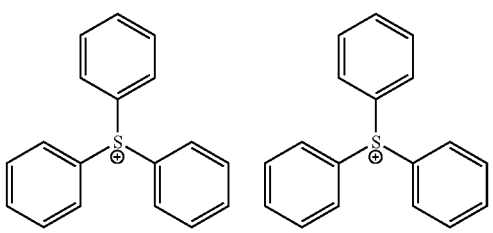
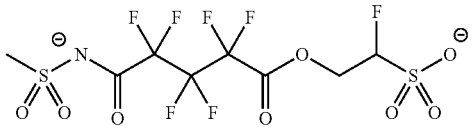
B-6
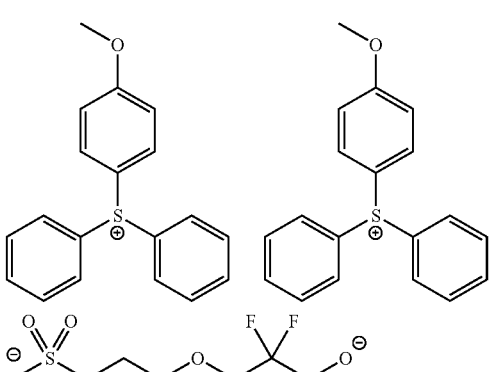
B-7
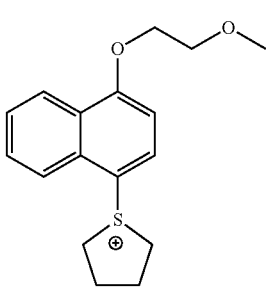

-continued
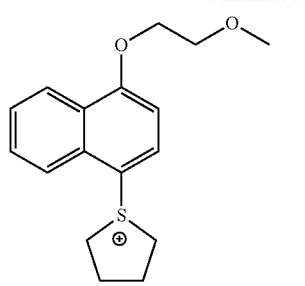
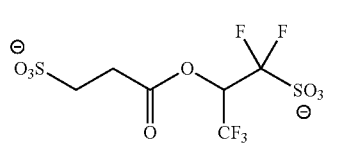
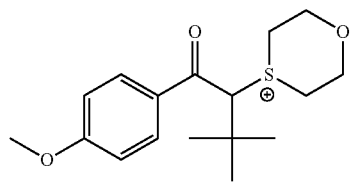
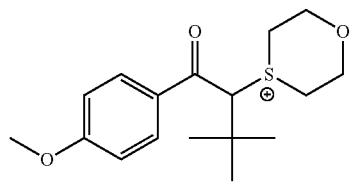
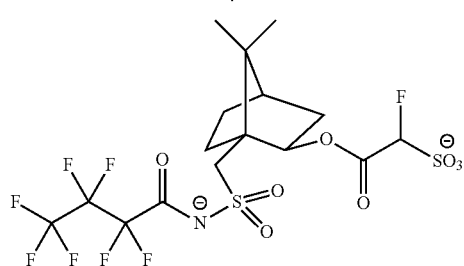
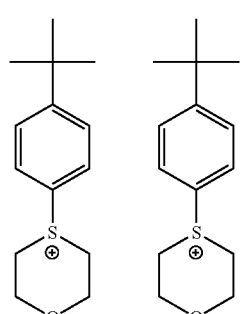
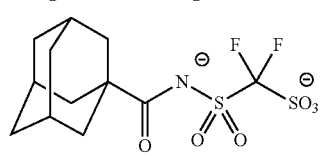
-continued
B-10
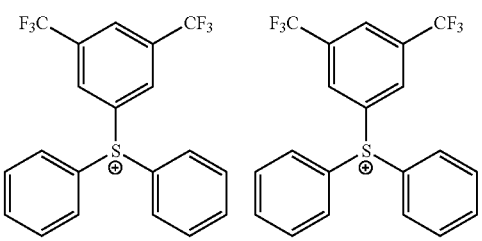
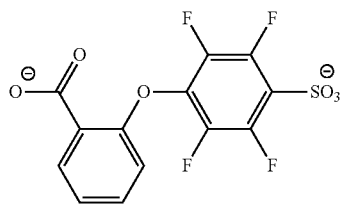
B-11
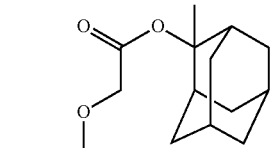
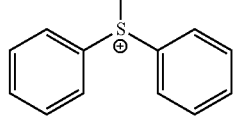
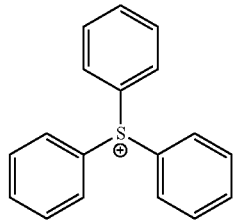
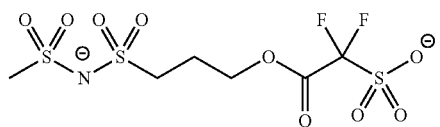
B-12
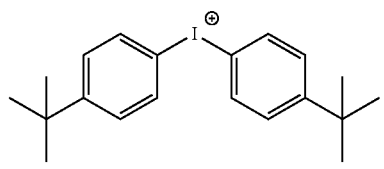
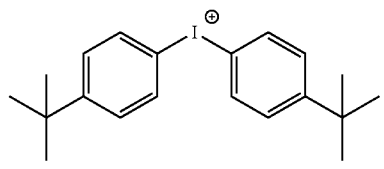
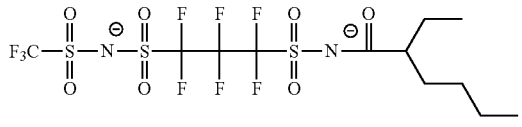

B-13
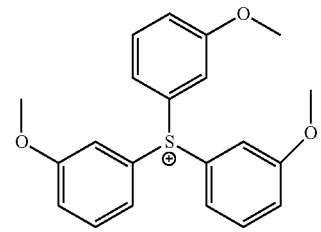
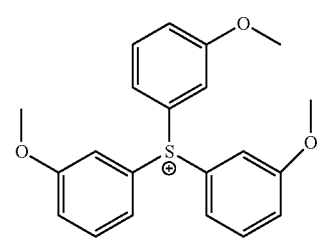
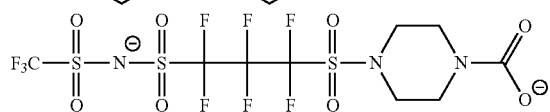
B-14
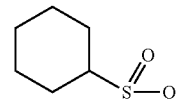 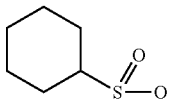
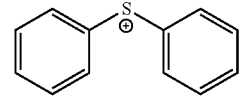 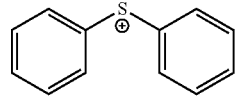
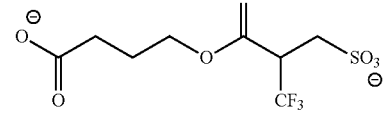
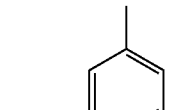 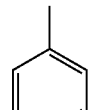
B-15
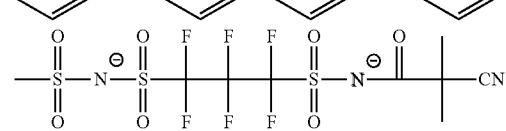
B-16
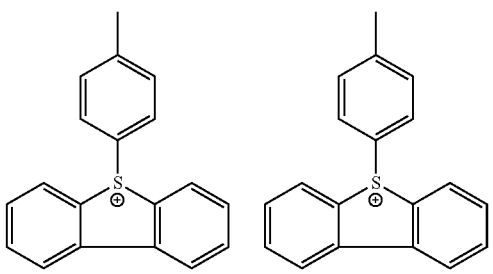
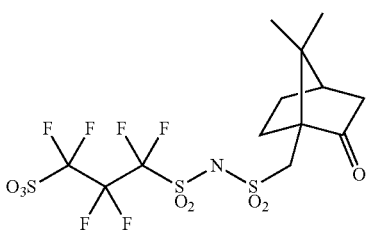
B-17
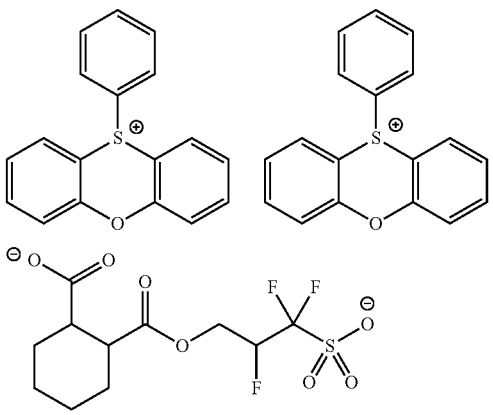
B-18
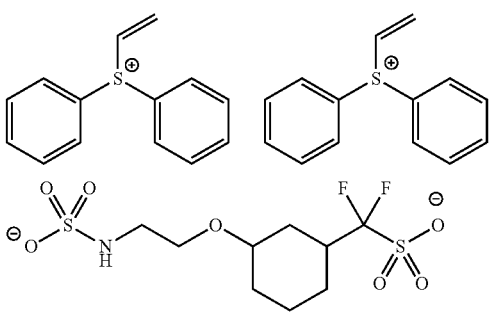
B-19
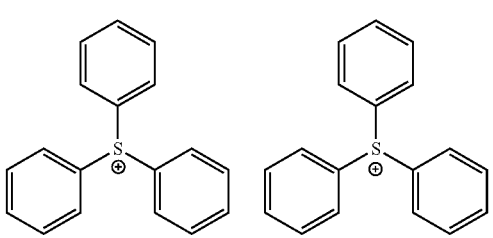

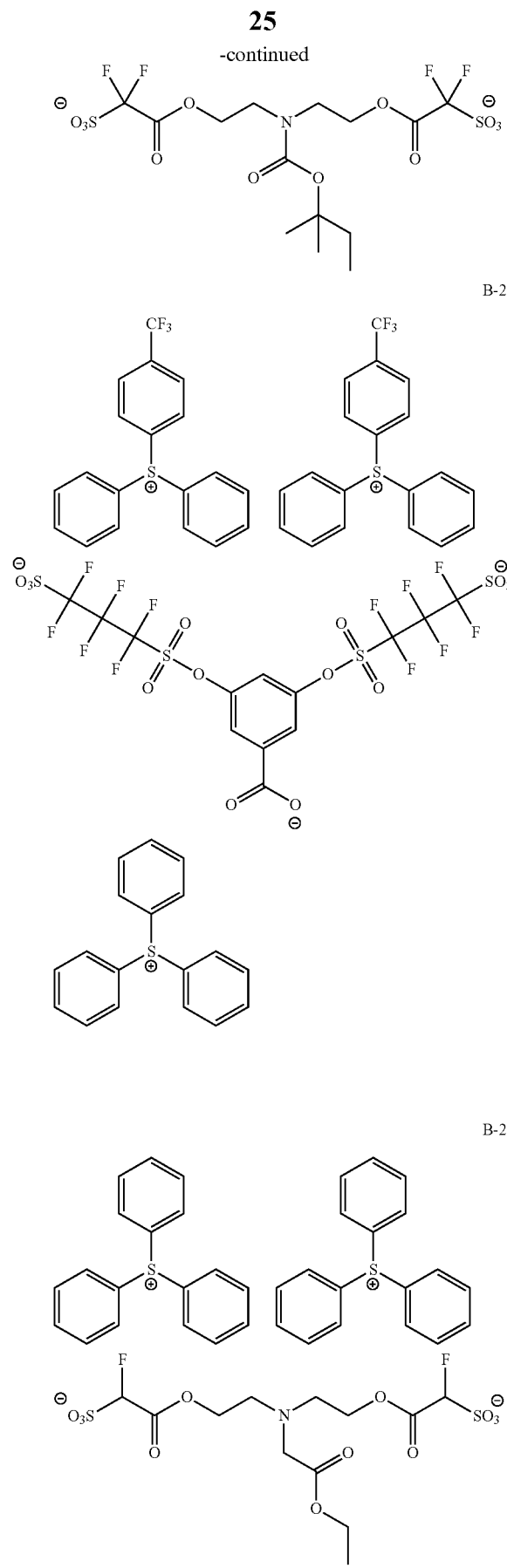
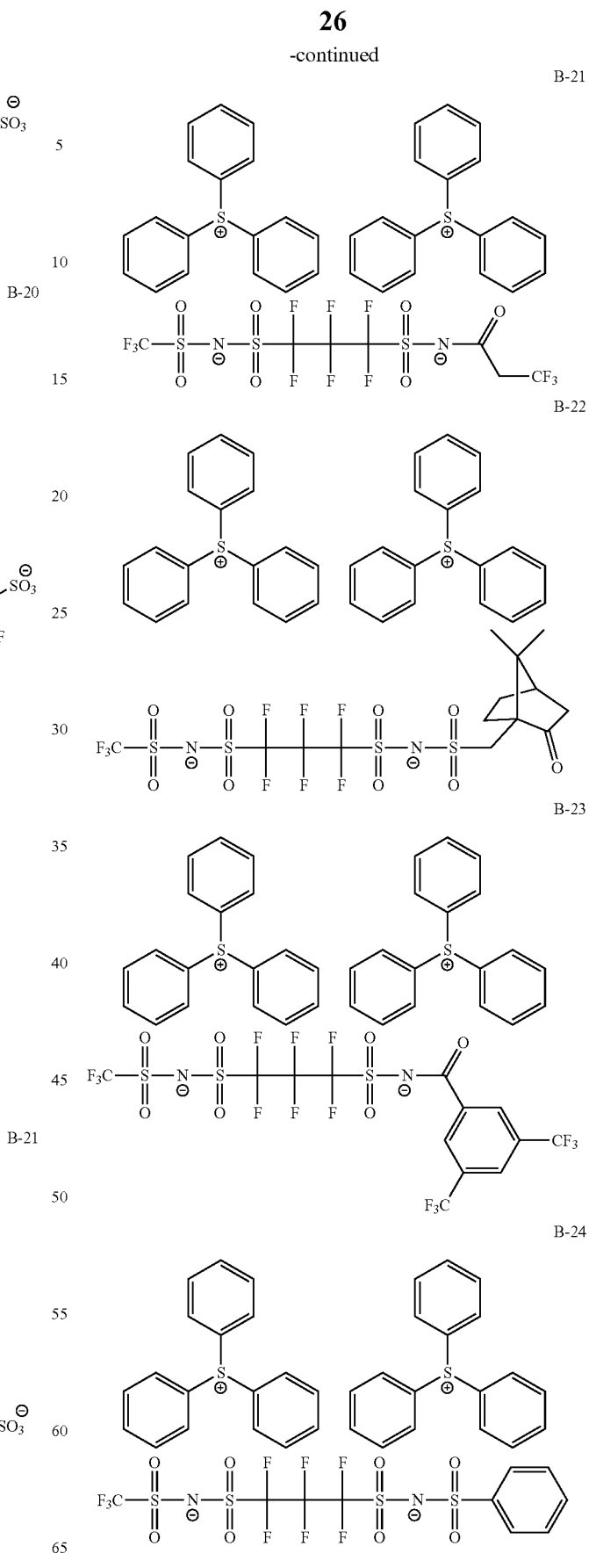

(Other Photoacid Generators)

Other photoacid generators other than the specific photoacid generator that can be included in the specific resist composition are not particularly limited. As such other photoacid generators, for example, the known compounds disclosed in paragraphs [0125] to [0319] of the specification of US2016/0070167A1, paragraphs [0086] to [0094] of the specification of US2015/0004544A1, paragraphs [0323] to [0402] of the specification of US2016/0237190A1, and paragraphs [0074] to [0122] and [0137] to [0146] of JP2018-155788A can be suitably used as the acid diffusion control agent.

In a case where the specific resist composition includes other photoacid generators, a content of such other photoacid generators is preferably 0.1% to 10.0% by mass with respect to the total solid content of the composition.

Such other photoacid generators may be used alone or in combination of two or more kinds thereof. In a case where two or more kinds of such other photoacid generators are used, a total content thereof is preferably within the suitable content range.

<Acid-Decomposable Resin (Resin (A))>

The specific resist composition includes a resin (hereinafter also referred to as an "acid-decomposable resin" or a "resin (A)") having a polarity that increases due to decomposition by the action of an acid.

That is, in the pattern forming method of an embodiment of the present invention which will be described later, typically, in a case where an alkali developer is adopted as the developer, a positive tone pattern is suitably formed, and in a case where an organic developer is adopted as the developer, a negative tone pattern is suitably formed.

The resin (A) usually includes a repeating unit having a group having a polarity that increases due to decomposition by the action of an acid (hereinafter also referred to as an "acid-decomposable group"), and preferably includes a repeating unit having an acid-decomposable group.

<<Repeating Unit Having Acid-Decomposable Group>>

The acid-decomposable group is a group that decomposes by the action of an acid to produce a polar group. The acid-decomposable group preferably has a structure in which the polar group is protected by an eliminable group that is eliminated by the action of an acid. That is, the resin (A) has a repeating unit having a group that decomposes by the action of an acid to produce a polar group. A resin having this repeating unit has an increased polarity by the action of an acid, and thus has an increased solubility in an alkali developer, and a decreased solubility in an organic solvent.

As the polar group, an alkali-soluble group is preferable, and examples thereof include an acidic group such as a carboxyl group, a phenolic hydroxyl group, a fluorinated alcohol group, a sulfonic acid group, a phosphoric acid group, a sulfonamide group, a sulfonylimide group, an (alkylsulfonyl)(alkylcarbonyl)methylene group, an (alkylsulfonyl)(alkylcarbonyl)imide group, a bis(alkylcarbonyl)methylene group, a bis(alkylcarbonyl)imide group, a bis(alkylsulfonyl)methylene group, a bis(alkylsulfonyl)imide group, a tris(alkylcarbonyl)methylene group, and a tris(alkylsulfonyl)methylene group, and an alcoholic hydroxyl group.

Among those, as the polar group, the carboxyl group, the phenolic hydroxyl group, the fluorinated alcohol group (preferably a hexafluoroisopropanol group), or the sulfonic acid group is preferable.

Examples of the eliminable group that is eliminated by the action of an acid include groups represented by Formulae (Y1) to (Y4).

$-C(Rx_1)(Rx_2)(Rx_3)$ Formula (Y1):

$-C(=O)OC(Rx_1)(Rx_2)(Rx_3)$ Formula (Y2):

$-C(R_{36})(R_{37})(OR_{38})$ Formula (Y3):

$-C(Rn)(H)(Ar)$ Formula (Y4):

In Formula (Y1) and Formula (Y2), $Rx_1$ to $Rx_3$ each independently represent an (linear or branched) alkyl group or (monocyclic or polycyclic) cycloalkyl group, an (linear or branched) alkenyl group, or an (monocyclic or polycyclic) aryl group. Furthermore, in a case where all of $Rx_1$ to $Rx_3$ are (linear or branched) alkyl groups, it is preferable that at least two of $Rx_1$, $Rx_2$, or $Rx_3$ are methyl groups.

Above all, it is preferable that $Rx_1$ to $Rx_3$ each independently represent a linear or branched alkyl group, and it is more preferable that $Rx_1$ to $Rx_3$ each independently represent the linear alkyl group.

Two of $Rx_1$ to $Rx_3$ may be bonded to each other to form a monocycle or a polycycle.

As the alkyl group of each of $Rx_1$ to $Rx_3$, an alkyl group having 1 to 5 carbon atoms, such as a methyl group, an ethyl group, an n-propyl group, an isopropyl group, an n-butyl group, an isobutyl group, and a t-butyl group, is preferable.

As the cycloalkyl group of each of $Rx_1$ to $Rx_3$, a monocyclic cycloalkyl group such as a cyclopentyl group and a cyclohexyl group, or a polycyclic cycloalkyl group such as a norbornyl group, a tetracyclodecanyl group, a tetracyclododecanyl group, and an adamantyl group is preferable.

As the aryl group as each of $Rx_1$ to $Rx_3$, an aryl group having 6 to 10 carbon atoms is preferable, and examples thereof include a phenyl group, a naphthyl group, and an anthryl group.

As the alkenyl group of each of $Rx_1$ to $Rx_3$, a vinyl group is preferable.

As a ring formed by the bonding of two of $Rx_1$ to $Rx_3$, a cycloalkyl group is preferable. As the cycloalkyl group formed by the bonding of two of $Rx_1$ to $Rx_3$, a monocyclic cycloalkyl group such as a cyclopentyl group or a cyclohexyl group, or a polycyclic cycloalkyl group such as a norbornyl group, a tetracyclodecanyl group, a tetracyclododecanyl group, or an adamantyl group is preferable, and a monocyclic cycloalkyl group having 5 or 6 carbon atoms is more preferable.

In the cycloalkyl group formed by the bonding of two of $Rx_1$ to $Rx_3$, for example, one of the methylene groups constituting the ring may be substituted with a heteroatom such as an oxygen atom, a group having a heteroatom, such as a carbonyl group, or a vinylidene group. In addition, in the cycloalkyl group, one or more of the ethylene groups constituting the cycloalkane ring may be substituted with a vinylene group.

With regard to the group represented by Formula (Y1) or Formula (Y2), for example, an aspect in which $Rx_1$ is a methyl group or an ethyl group, and $Rx_2$ and $Rx_3$ are bonded to each other to form a cycloalkyl group is preferable.

In Formula (Y3), $R_{36}$ to $R_{38}$ each independently represent a hydrogen atom or a monovalent organic group. $R_{37}$ and $R_{38}$ may be bonded to each other to form a ring. Examples of the monovalent organic group include an alkyl group, a cycloalkyl group, an aryl group, an aralkyl group, and an alkenyl group. It is also preferable that $R_{36}$ is the hydrogen atom.

Furthermore, the alkyl group, the cycloalkyl group, the aryl group, and the aralkyl group may include a heteroatom such as an oxygen atom, and/or a group having a heteroatom, such as a carbonyl group. For example, in the alkyl group, the cycloalkyl group, the aryl group, and the aralkyl group, one or more of the methylene groups may be substituted with a heteroatom such as an oxygen atom and/or a group having a heteroatom, such as a carbonyl group.

In addition, $R_{38}$ and another substituent contained in the main chain of the repeating unit may be bonded to each other to form a ring. A group formed by the mutual bonding of $R_{38}$ and another substituent on the main chain of the repeating unit is preferably an alkylene group such as a methylene group.

As Formula (Y3), a group represented by Formula (Y3-1) is preferable.

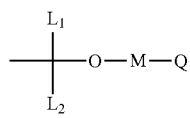
(Y3-1)

Here, $L_1$ and $L_2$ each independently represent a hydrogen atom, an alkyl group, a cycloalkyl group, an aryl group, or a group formed by combination thereof (for example, a group formed by combination of an alkyl group and an aryl group).

M represents a single bond or a divalent linking group.

Q represents an alkyl group which may include a heteroatom, a cycloalkyl group which may include a heteroatom, an aryl group which may include a heteroatom, an amino group, an ammonium group, a mercapto group, a cyano group, an aldehyde group, or a group formed by combination thereof (for example, a group formed by combination of an alkyl group and a cycloalkyl group).

In the alkyl group and the cycloalkyl group, for example, one of the methylene groups may be substituted with a heteroatom such as an oxygen atom or a group having a heteroatom, such as a carbonyl group.

In addition, it is preferable that one of $L_1$ or $L_2$ is a hydrogen atom, and the other is an alkyl group, a cycloalkyl group, an aryl group, or a group formed by combination of an alkylene group and an aryl group.

At least two of Q, M, or $L_1$ may be bonded to each other to form a ring (preferably a 5- or 6-membered ring).

From the viewpoint of pattern miniaturization, $L_2$ is preferably a secondary or tertiary alkyl group, and more preferably the tertiary alkyl group. Examples of the secondary alkyl group include an isopropyl group, a cyclohexyl group, and a norbornyl group, and examples of the tertiary alkyl group include a tert-butyl group and an adamantane group. In these aspects, since the glass transition temperature (Tg) and the activation energy are increased, it is possible to suppress fogging in addition to ensuring film hardness.

In Formula (Y4), Ar represents an aromatic ring group. Rn represents an alkyl group, a cycloalkyl group, or an aryl group. Rn and Ar may be bonded to each other to form a non-aromatic ring. Ar is more preferably the aryl group.

From the viewpoint that the acid decomposability of the repeating unit is excellent, in a case where a non-aromatic ring is directly bonded to a polar group (or a residue thereof) in an eliminable group that protects the polar group, it is also preferable that a ring member atom adjacent to the ring member atom directly bonded to the polar group (or a residue thereof) in the non-aromatic ring has no halogen atom such as a fluorine atom as a substituent.

In addition, the eliminable group that is eliminated by the action of an acid may be a 2-cyclopentenyl group having a substituent (an alkyl group and the like), such as a 3-methyl-2-cyclopentenyl group, and a cyclohexyl group having a substituent (an alkyl group and the like), such as a 1,1,4,4-tetramethylcyclohexyl group.

As the repeating unit having an acid-decomposable group, a repeating unit represented by Formula (A) is also preferable.

(A)

$L_1$ represents a divalent linking group which may have a fluorine atom or an iodine atom, $R_1$ represents a hydrogen atom, a fluorine atom, an iodine atom, a fluorine atom, an alkyl group which may have an iodine atom, or an aryl group which may have a fluorine atom or an iodine atom, and $R_2$ represents an eliminable group that is eliminated by the action of an acid and may have a fluorine atom or an iodine atom. It should be noted that at least one of $L_1$, $R_1$, or $R_2$ has a fluorine atom or an iodine atom.

$L_1$ represents a divalent linking group which may have a fluorine atom or an iodine atom. Examples of the divalent linking group which may have a fluorine atom or an iodine atom include —CO—, —O—, —S—, —SO—, —SO$_2$—, a hydrocarbon group which may have a fluorine atom or an iodine atom (for example, an alkylene group, a cycloalkylene group, an alkenylene group, and an arylene group), and a linking group formed by the linking of a plurality of these groups. Among those, as $L_1$, —CO— or -arylene group-alkylene group having a fluorine atom or an iodine atom- is preferable.

As the arylene group, a phenylene group is preferable.

The alkylene group may be linear or branched. The number of carbon atoms of the alkylene group is not particularly limited, but is preferably 1 to 10, and more preferably 1 to 3.

The total number of fluorine atoms and iodine atoms included in the alkylene group having a fluorine atom or an iodine atom is not particularly limited, but is preferably 2 or more, more preferably 2 to 10, and still more preferably 3 to 6.

$R_1$ represents a hydrogen atom, a fluorine atom, an iodine atom, an alkyl group which may have a fluorine atom or an iodine atom, or an aryl group which may have a fluorine atom or an iodine atom.

The alkyl group may be linear or branched. The number of carbon atoms of the alkyl group is not particularly limited, but is preferably 1 to 10, and more preferably 1 to 3.

The total number of fluorine atoms and iodine atoms included in the alkyl group having a fluorine atom or an iodine atom is not particularly limited, but is preferably 1 or more, more preferably 1 to 5, and still more preferably 1 to 3.

The alkyl group may include a heteroatom such as an oxygen atom, other than a halogen atom.

$R_2$ represents an eliminable group that is eliminated by the action of an acid and may have a fluorine atom or an iodine atom.

Among those, examples of the eliminable group include groups represented by Formulae (Z1) to (Z4).

Formula (Z1): —$C(Rx_1)(Rx_{12})(Rx_{13})$ Formula (Z2): —$C(=O)OC(Rx_1)(Rx_{12})(Rx_{13})$ Formula (Z3): —$C(R_{136})(R_{137})(OR_{138})$ Formula (Z4): —$C(Rn_1)(H)(Ar_1)$ In Formulae (Z1) and (Z2), $Rx_{11}$ to $Rx_{13}$ each independently represent an (linear or branched) alkyl group which may have a fluorine atom or an iodine atom, a (monocyclic or polycyclic) cycloalkyl group which may have a fluorine atom or an iodine atom, an (linear or branched) alkenyl group which may have a fluorine atom or an iodine atom, or an (monocyclic or polycyclic) aryl group which may have a fluorine atom or an iodine atom. Furthermore, in a case where all of $Rx_{11}$ to $Rx_{13}$ are each an (linear or branched) alkyl group, it is preferable that at least two of $Rx_{11}$, $Rx_{12}$, or $Rx_{13}$ are methyl groups.

$Rx_{11}$ to $Rx_{13}$ are the same as $Rx_1$ to $Rx_3$ in Formulae (Y1) and (Y2) described above, respectively, except that they may have a fluorine atom or an iodine atom, and have the same definitions and suitable ranges as those of the alkyl group, the cycloalkyl group, the alkenyl group, and the aryl group.

In Formula (Z3), $R_{136}$ to $R_{138}$ each independently represent a hydrogen atom, or a monovalent organic group which may have a fluorine atom or an iodine atom. $R_{137}$ and $R_{138}$ may be bonded to each other to form a ring. Examples of the monovalent organic group which may have a fluorine atom or an iodine atom include an alkyl group which may have a fluorine atom or an iodine atom, a cycloalkyl group which may have a fluorine atom or an iodine atom, an aryl group which may have a fluorine atom or an iodine atom, an aralkyl group which may have a fluorine atom or an iodine atom, and a group formed by combination thereof (for example, a group formed by combination of the alkyl group and the cycloalkyl group).

Incidentally, the alkyl group, the cycloalkyl group, the aryl group, and the aralkyl group may include a heteroatom such as an oxygen atom, in addition to the fluorine atom and the iodine atom. That is, in the alkyl group, the cycloalkyl group, the aryl group, and the aralkyl group, for example, one of the methylene groups may be substituted with a heteroatom such as an oxygen atom or a group having a heteroatom, such as a carbonyl group.

In addition, $R_{138}$ and another substituent contained in the main chain of the repeating unit may be bonded to each other to form a ring. In this case, a group formed by the mutual bonding of $R_{138}$ and another substituent on the main chain of the repeating unit is preferably an alkylene group such as a methylene group.

As Formula (Z3), a group represented by Formula (Z3-1) is preferable.

(Z3-1)

Here, $L_1$ and $L_{12}$ each independently represent a hydrogen atom; an alkyl group which may have a heteroatom selected from the group consisting of a fluorine atom, an iodine atom, and an oxygen atom; a cycloalkyl group which may have a heteroatom selected from the group consisting of a fluorine atom, an iodine atom, and an oxygen atom; an aryl group which may have a heteroatom selected from the group consisting of a fluorine atom, an iodine atom, and an oxygen atom; or a group formed by combination thereof (for example, a group formed by combination of an alkyl group and a cycloalkyl group, each of which may have a heteroatom selected from the group consisting of a fluorine atom, an iodine atom, and an oxygen atom).

$M_1$ represents a single bond or a divalent linking group.

$Q_1$ represents an alkyl group which may have a heteroatom selected from the group consisting of a fluorine atom, an iodine atom, and an oxygen atom; a cycloalkyl group which may have a heteroatom selected from the group consisting of a fluorine atom, an iodine atom, and an oxygen atom; an aryl group which may have a heteroatom selected from the group consisting of a fluorine atom, an iodine atom, and an oxygen atom; an amino group; an ammonium group; a mercapto group; a cyano group; an aldehyde group; a group formed by combination thereof (for example, a group formed by combination of the alkyl group and the cycloalkyl group, each of which may have a heteroatom selected from the group consisting of a fluorine atom, an iodine atom, and an oxygen atom).

In Formula (Z4), $Ar_1$ represents an aromatic ring group which may have a fluorine atom or an iodine atom. $Rn_1$ is an alkyl group which may have a fluorine atom or an iodine atom, a cycloalkyl group which may have a fluorine atom or an iodine atom, or an aryl group which may have a fluorine atom or an iodine atom. $Rn_1$ and $Ar_1$ may be bonded to each other to form a non-aromatic ring.

As the repeating unit having an acid-decomposable group, a repeating unit represented by General Formula (AI) is also preferable.

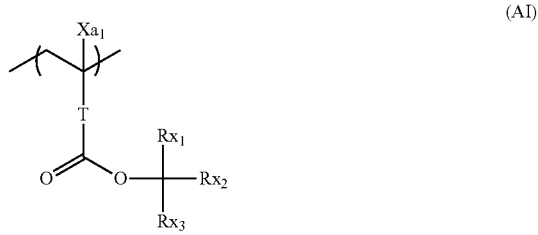

(AI)

In General Formula (AI), $Xa_1$ represents a hydrogen atom, or an alkyl group which may have a substituent.

T represents a single bond or a divalent linking group.

$Rx_1$ to $Rx_3$ each independently represent an (linear or branched) alkyl group, a (monocyclic or polycyclic) cycloalkyl group, an (linear or branched) alkenyl group, or an (monocyclic or polycyclic) aryl group. It should be noted that in a case where all of $Rx_1$ to $Rx_3$ are (linear or branched) alkyl groups, it is preferable that at least two of $Rx_1$, $Rx_2$, or $Rx_3$ are methyl groups.

Two of $Rx_1$ to $Rx_3$ may be bonded to each other to form a monocycle or polycycle (a monocyclic or polycyclic cycloalkyl group and the like).

Examples of the alkyl group which may have a substituent, represented by $Xa_1$, include a methyl group and a group represented by —$CH_2$—$R_{11}$. $R_{11}$ represents a halogen atom (a fluorine atom or the like), a hydroxyl group, or a monovalent organic group, examples thereof include an alkyl group having 5 or less carbon atoms, which may be substituted with a halogen atom, an acyl group having 5 or less carbon atoms, which may be substituted with a halogen atom, and an alkoxy group having 5 or less carbon atoms, which may be substituted with a halogen atom; and an alkyl group having 3 or less carbon atoms is preferable, and a methyl group is more preferable. $Xa_1$ is preferably a hydrogen atom, a methyl group, a trifluoromethyl group, or a hydroxymethyl group.

Examples of the divalent linking group of T include an alkylene group, an aromatic ring group, a —COO-Rt- group, and an —O-Rt- group. In the formulae, Rt represents an alkylene group or a cycloalkylene group.

T is preferably the single bond or the —COO-Rt- group. In a case where T represents the —COO-Rt-group, Rt is preferably an alkylene group having 1 to 5 carbon atoms, and more preferably a —$CH_2$— group, a —$(CH_2)_2$— group, or a —$(CH_2)_3$— group.

As the alkyl group of each of $Rx_1$ to $Rx_3$, an alkyl group having 1 to 4 carbon atoms, such as a methyl group, an ethyl group, an n-propyl group, an isopropyl group, an n-butyl group, an isobutyl group, and a t-butyl group, is preferable.

As the cycloalkyl group of each of $Rx_1$ to $Rx_3$, a monocyclic cycloalkyl group such as a cyclopentyl group and a cyclohexyl group, or a polycyclic cycloalkyl group such as a norbornyl group, a tetracyclodecanyl group, a tetracyclododecanyl group, and an adamantyl group is preferable.

As the aryl group as each of $Rx_1$ to $Rx_3$, an aryl group having 6 to 10 carbon atoms is preferable, and examples thereof include a phenyl group, a naphthyl group, and an anthryl group.

As the alkenyl group of each of $Rx_1$ to $Rx_3$, a vinyl group is preferable.

As the cycloalkyl group formed by the bonding of two of $Rx_1$ to $Rx_3$, a monocyclic cycloalkyl group such as a cyclopentyl group and a cyclohexyl group is preferable, and in addition, a polycyclic cycloalkyl group such as a norbornyl group, a tetracyclodecanyl group, a tetracyclododecanyl group, and an adamantyl group is also preferable. Among those, a monocyclic cycloalkyl group having 5 or 6 carbon atoms is preferable.

In the cycloalkyl group formed by the bonding of two of $Rx_1$ to $Rx_3$, for example, one of the methylene groups constituting the ring may be substituted with a heteroatom such as an oxygen atom, a group having a heteroatom, such as a carbonyl group, or a vinylidene group. In addition, in the cycloalkyl group, one or more of the ethylene groups constituting the cycloalkane ring may be substituted with a vinylene group.

With regard to the repeating unit represented by General Formula (AI), for example, an aspect in which $Rx_1$ is a methyl group or an ethyl group, and $Rx_2$ and $Rx_3$ are bonded to each other to form the above-mentioned cycloalkyl group is preferable.

In a case where each of the groups has a substituent, examples of the substituent include an alkyl group (having 1 to 4 carbon atoms), a halogen atom, a hydroxyl group, an alkoxy group (having 1 to 4 carbon atoms), a carboxyl group, and an alkoxycarbonyl group (having 2 to 6 carbon atoms). The substituent preferably has 8 or less carbon atoms.

The repeating unit represented by General Formula (AI) is preferably an acid-decomposable tertiary alkyl (meth) acrylate ester-based repeating unit (the repeating unit in which $Xa_1$ represents a hydrogen atom or a methyl group, and T represents a single bond).

The content of the repeating unit having an acid-decomposable group is preferably 15% by mole or more, more preferably 20% by mole or more, and still more preferably 30% by mole or more with respect to all repeating units in the resin (A). In addition, an upper limit value thereof is preferably 80% by mole or less, more preferably 70% by mole or less, and particularly preferably 60% by mole or less.

Specific examples of the repeating unit having an acid-decomposable group are shown below, but the present invention is not limited thereto. Furthermore, in the formulae, $Xa_1$ represents H, $CH_3$, $CF_3$, or $CH_2OH$, and Rxa and Rxb each represent a linear or branched alkyl group having 1 to 5 carbon atoms.

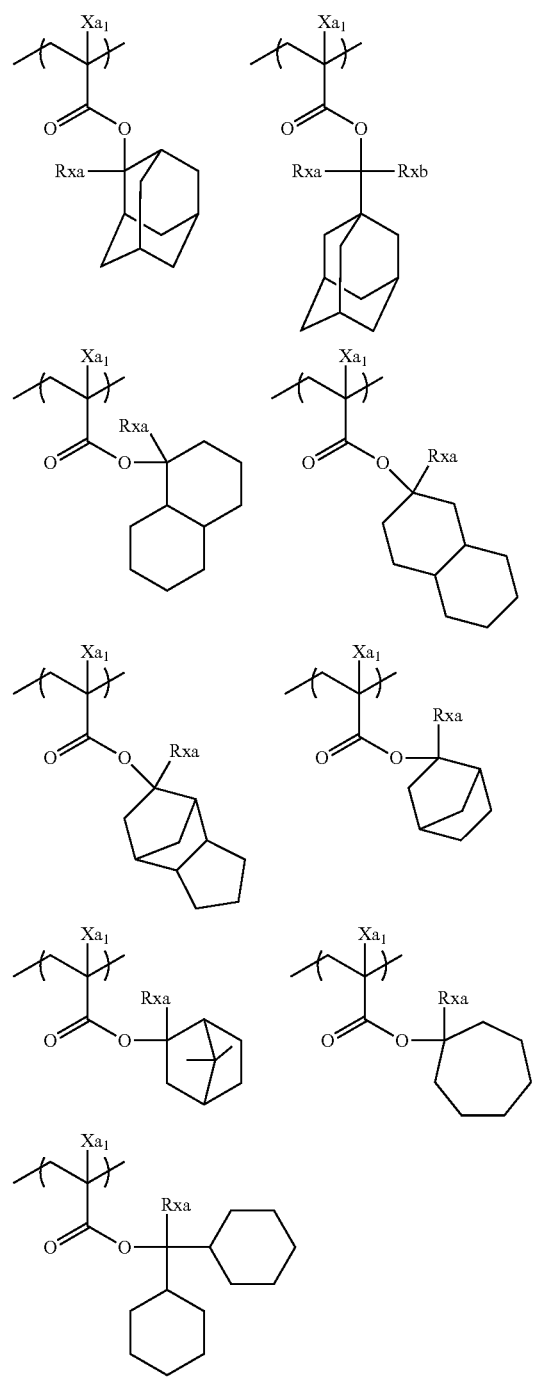

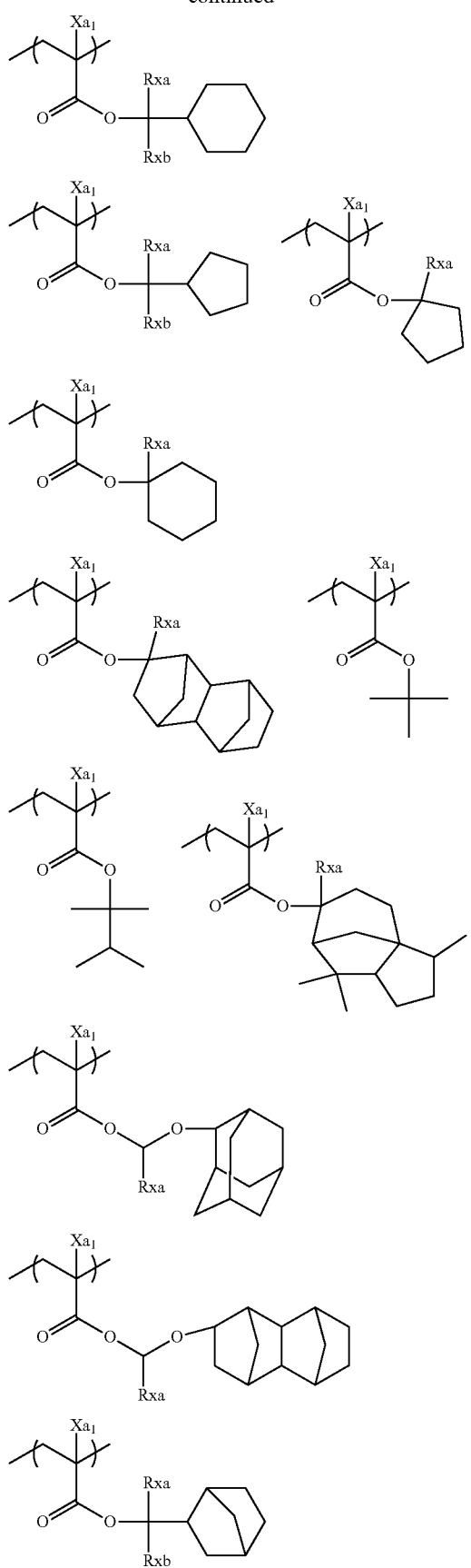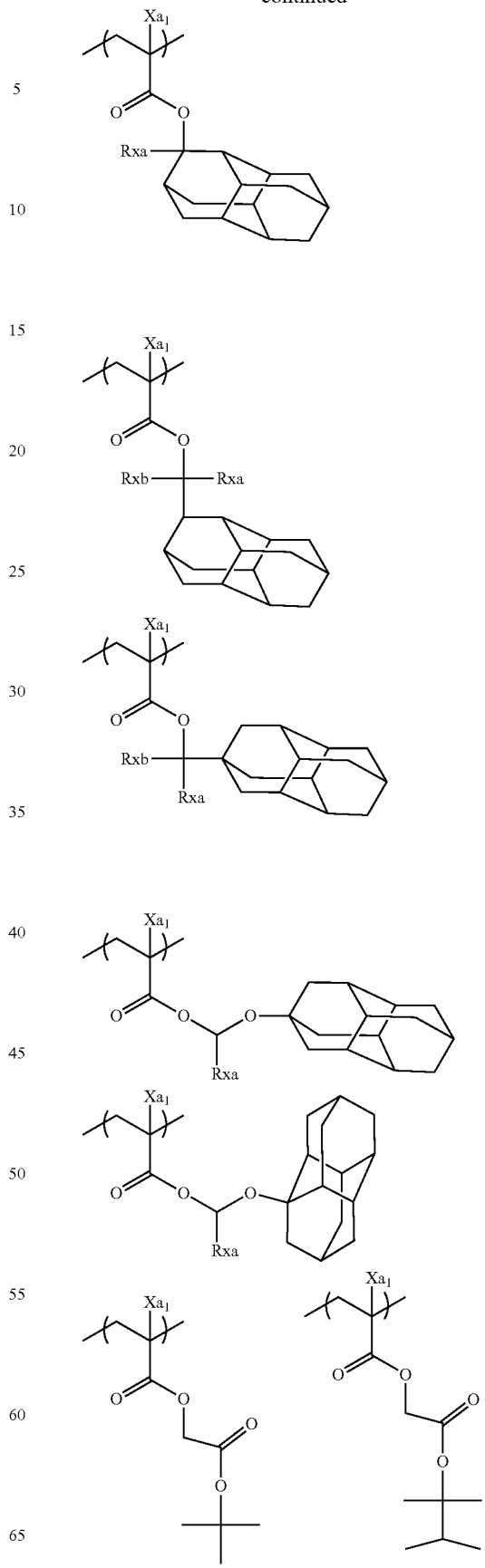

37
-continued
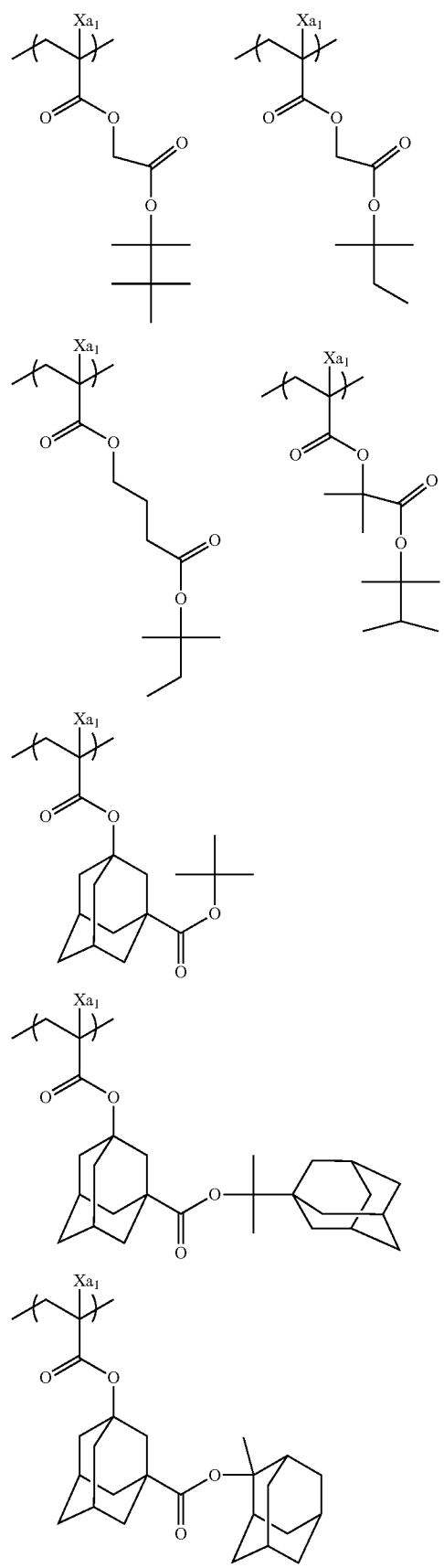
38
-continued
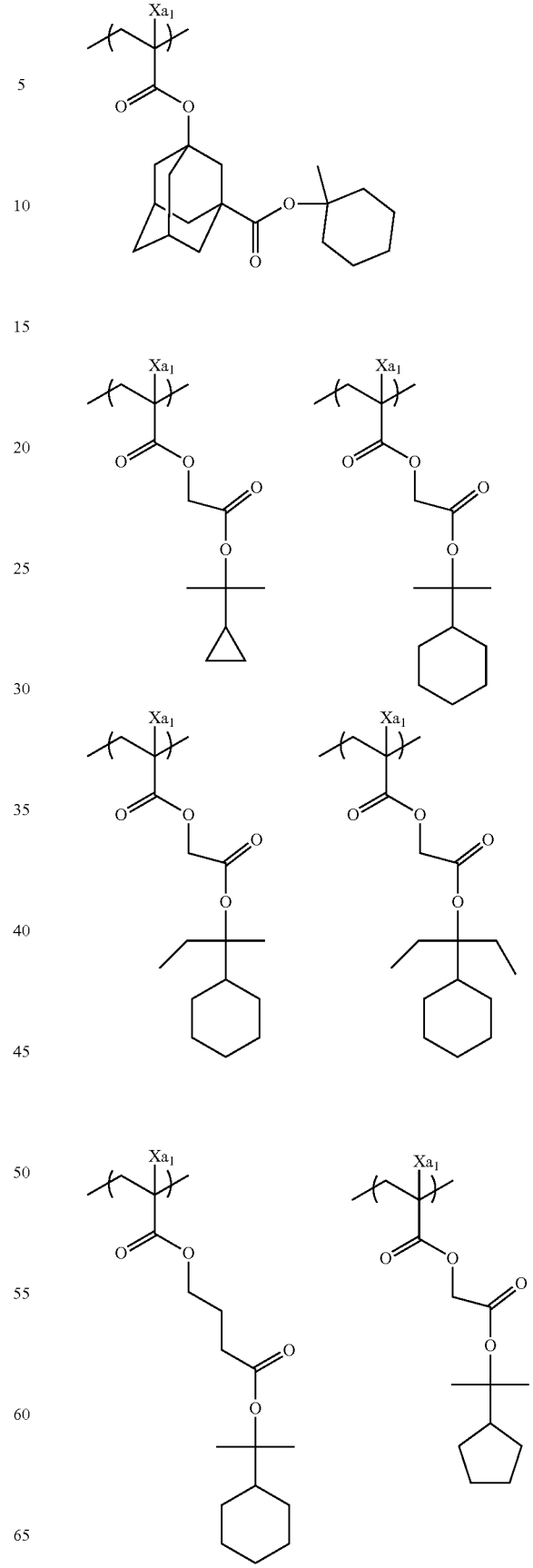

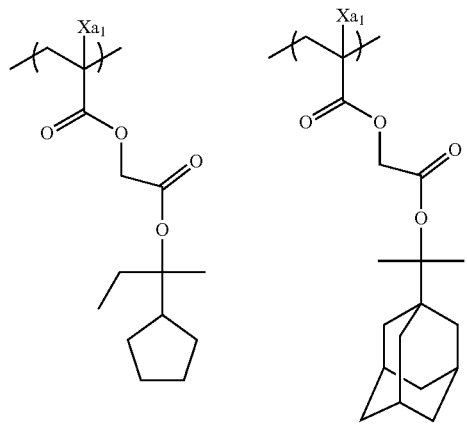
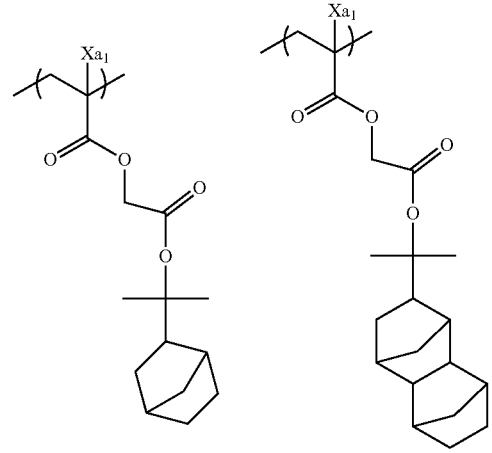
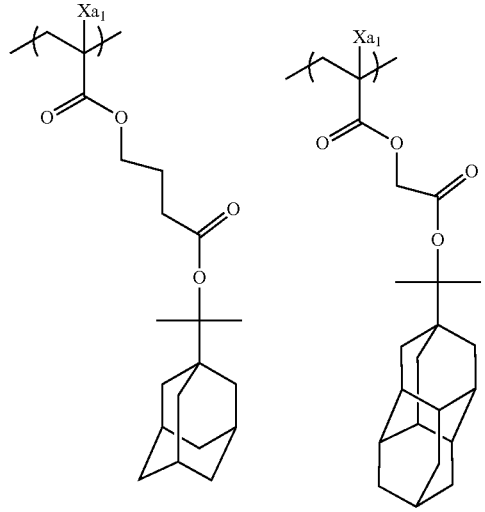
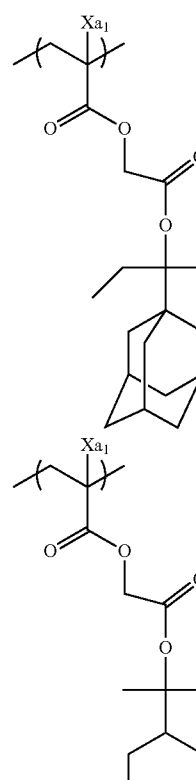
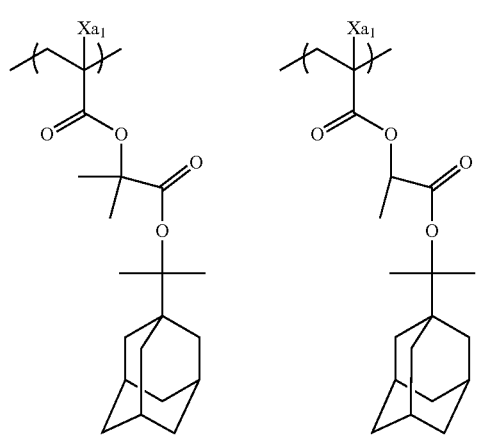
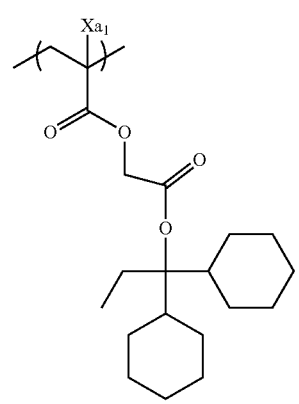

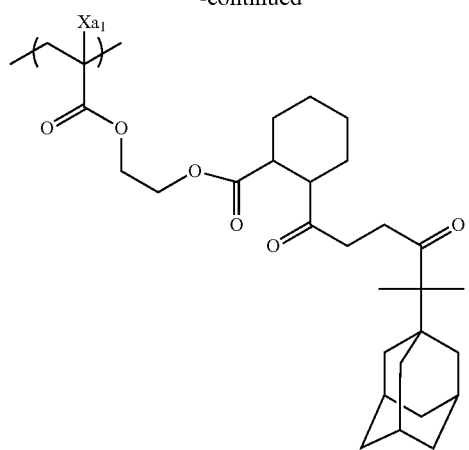
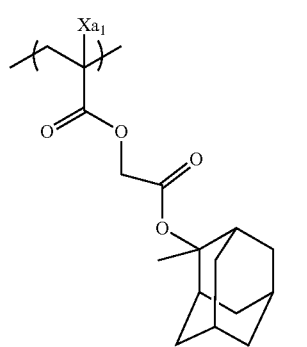
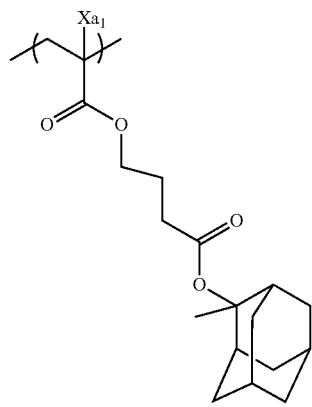
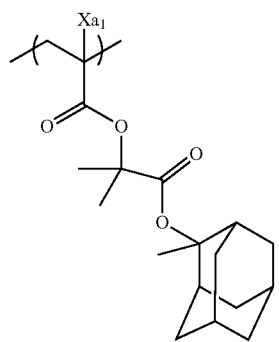
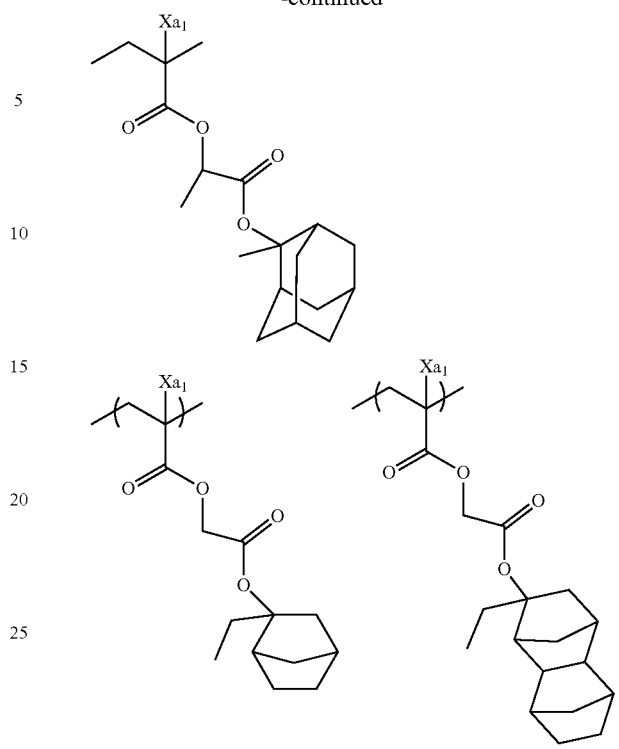
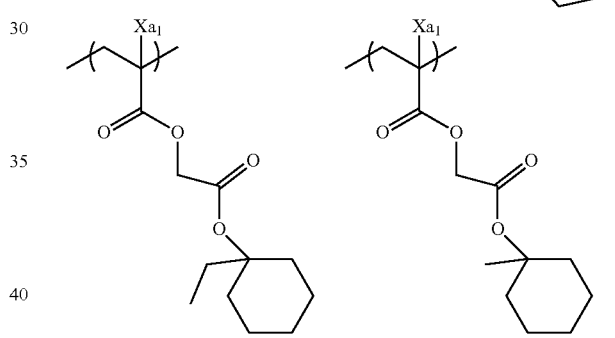
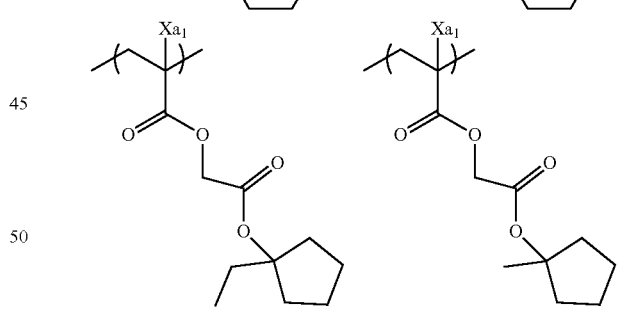
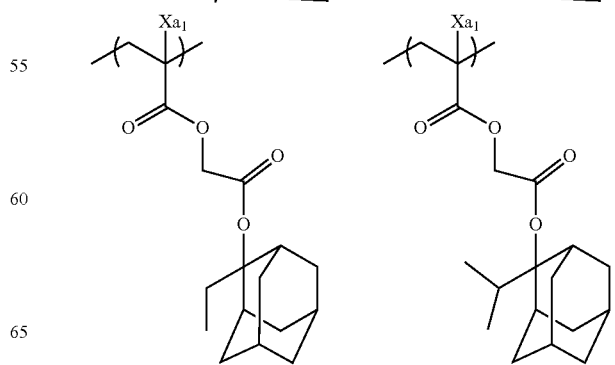

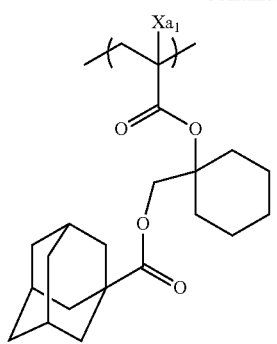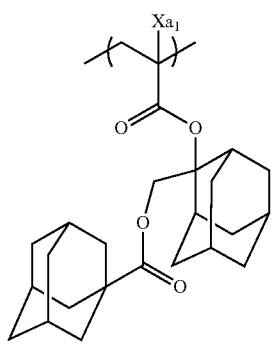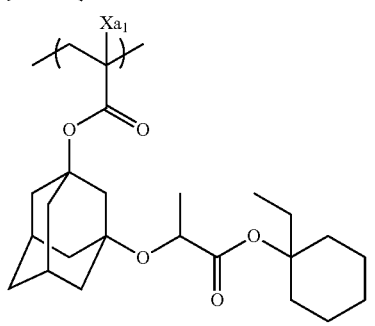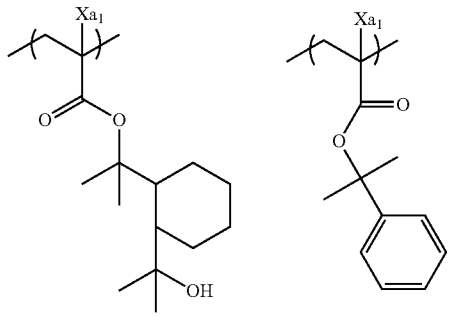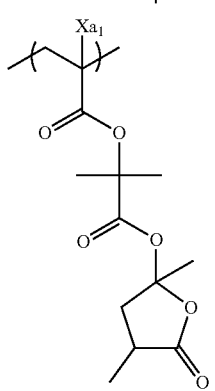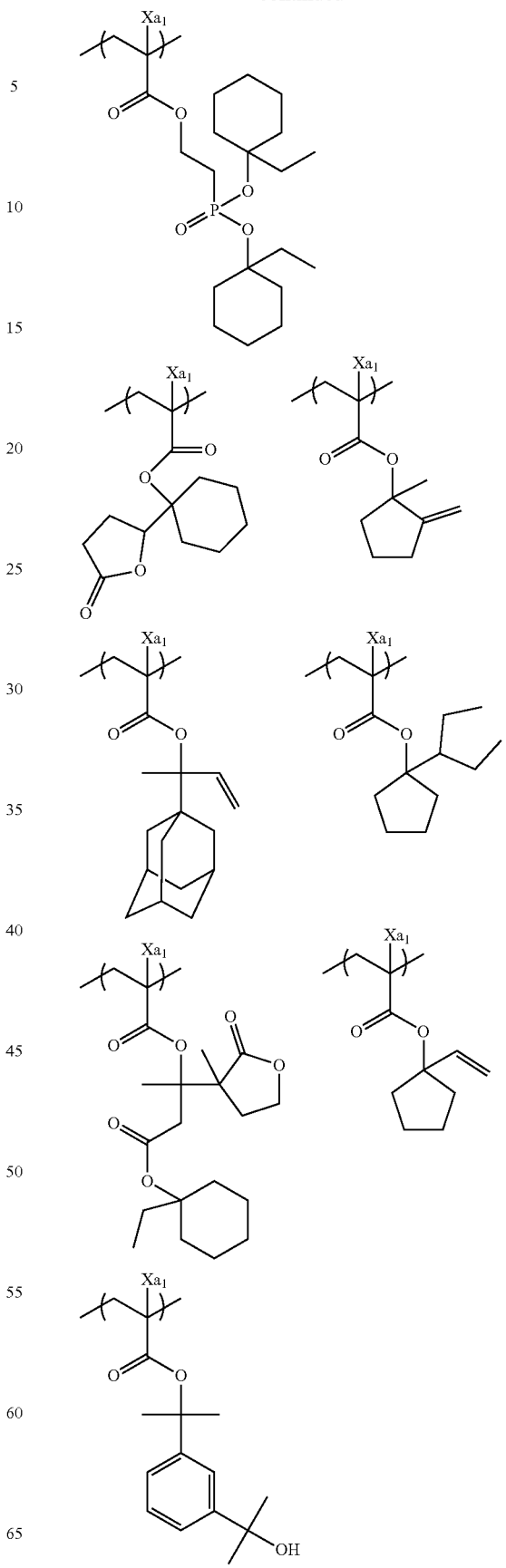

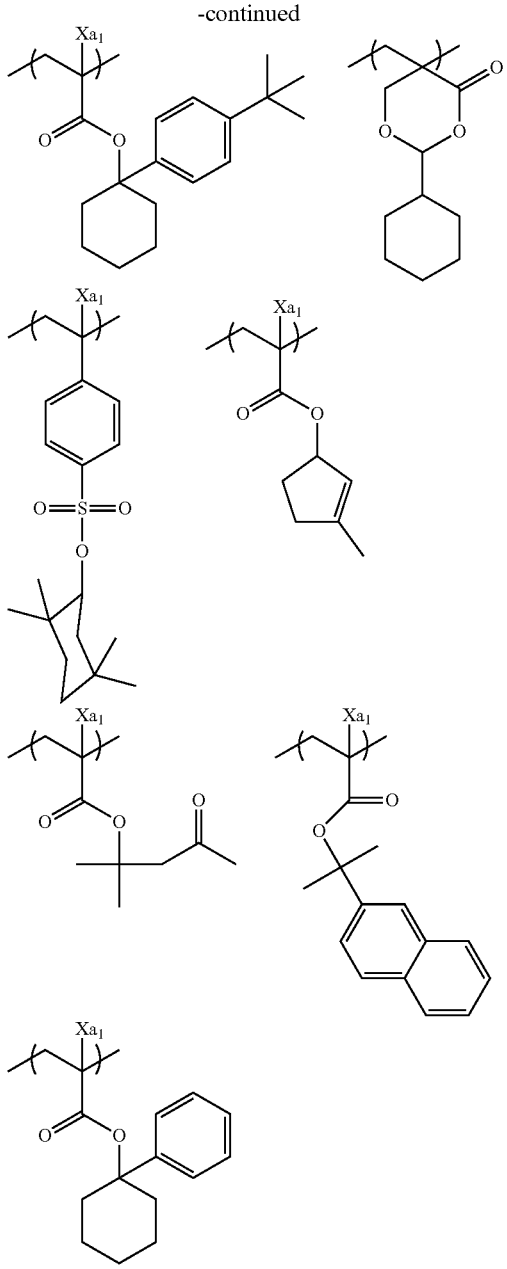

The resin (A) may include a repeating unit other than the above-mentioned repeating units.

For example, the resin (A) may include at least one repeating unit selected from the group consisting of the following group A and/or at least one repeating unit selected from the group consisting of the following group B.

Group A: A group consisting of the following repeating units (20) to (29).
- (20) A repeating unit having an acid group, which will be described later
- (21) A repeating unit having a fluorine atom or an iodine atom, which will be described later
- (22) A repeating unit having a lactone group, a sultone group, or a carbonate group, which will be described later
- (23) A repeating unit having a photoacid generating group, which will be described later
- (24) A repeating unit represented by General Formula (V-1) or General Formula (V-2), which will be described later
- (25) A repeating unit represented by Formula (A), which will be described later
- (26) A repeating unit represented by Formula (B), which will be described later
- (27) A repeating unit represented by Formula (C), which will be described later
- (28) A repeating unit represented by Formula (D), which will be described later
- (29) A repeating unit group B represented by Formula (E), which will be described later: a group consisting of the following repeating units (30) to (32).
- (30) A repeating unit having at least one group selected from a lactone group, a sultone group, a carbonate group, a hydroxyl group, a cyano group, or an alkali-soluble group, which will be described later.
- (31) A repeating unit having an alicyclic hydrocarbon structure and not exhibiting acid decomposability described later.
- (32) A repeating unit represented by General Formula (III) having neither a hydroxyl group nor a cyano group, which will be described later.

In a case where the specific resist composition is used as a resist composition for EUV, it is preferable that the resin (A) has at least one repeating unit selected from the group consisting of the group A.

In addition, in a case where the specific resist composition is used as the resist composition for EUV, it is preferable that the resin (A) includes at least one of a fluorine atom or an iodine atom. In a case where the resin (A) includes both a fluorine atom and an iodine atom, the resin (A) may have one repeating unit including both a fluorine atom and an iodine atom, and the resin (A) may include two kinds of repeating units, that is, a repeating unit having a fluorine atom and a repeating unit having an iodine atom.

In addition, in a case where the specific resist composition is used as the resist composition for EUV, it is also preferable that the resin (A) has a repeating unit having an aromatic group.

In a case where the specific resist composition is used as a resist composition for ArF it is preferable that the resin (A) has at least one repeating unit selected from the group consisting of the group B.

Furthermore, in a case where the specific resist composition is used as the resist composition for ArF, it is preferable that the resin (A) includes neither a fluorine atom nor a silicon atom.

In addition, in a case where the specific resist composition is used as the resist composition for ArF, it is preferable that the resin (A) does not have an aromatic group.

<<Repeating Unit Having Acid Group>>

The resin (A) may have a repeating unit having an acid group.

As the acid group, an acid group having a pKa of 13 or less is preferable.

As the acid group, for example, a carboxyl group, a phenolic hydroxyl group, a fluorinated alcohol group (preferably a hexafluoroisopropanol group), a sulfonic acid group, a sulfonamide group, or an isopropanol group is preferable.

In addition, in the hexafluoroisopropanol group, one or more (preferably one or two) fluorine atoms may be substituted with a group (an alkoxycarbonyl group and the like) other than a fluorine atom. —C(CF$_3$)(OH)—CF$_2$— formed as above is also preferable as the acid group. In addition, one or more fluorine atoms may be substituted with a group other than a fluorine atom to form a ring including —C(CF₃)(OH)—CF₂—.

The repeating unit having an acid group is preferably a repeating unit different from a repeating unit having the structure in which a polar group is protected by the eliminable group that is eliminated by the action of an acid as described above, and a repeating unit having a lactone group, a sultone group, or a carbonate group which will be described later.

The repeating unit having an acid group may have a fluorine atom or an iodine atom.

As the repeating unit having an acid group, a repeating unit represented by Formula (B) is preferable.

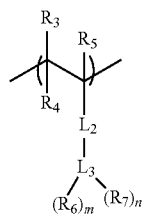

(B)

$R_3$ represents a hydrogen atom or a monovalent organic group which may have a fluorine atom or an iodine atom.

The monovalent organic group which may have a fluorine atom or an iodine atom is preferably a group represented by -$L_4$-$R_8$. $L_4$ represents a single bond or an ester group. $R_8$ is an alkyl group which may have a fluorine atom or an iodine atom, a cycloalkyl group which may have a fluorine atom or an iodine atom, an aryl group which may have a fluorine atom or an iodine atom, or a group formed by combination thereof.

$R_4$ and $R_5$ each independently represent a hydrogen atom, a fluorine atom, an iodine atom, or an alkyl group which may have a fluorine atom or an iodine atom.

$L_2$ represents a single bond or an ester group.

$L_3$ represents an (n+m+1)-valent aromatic hydrocarbon ring group or an (n+m+1)-valent alicyclic hydrocarbon ring group. Examples of the aromatic hydrocarbon ring group include a benzene ring group and a naphthalene ring group. The alicyclic hydrocarbon ring group may be either a monocycle or a polycycle, and examples thereof include a cycloalkyl ring group.

$R_6$ represents a hydroxyl group or a fluorinated alcohol group (preferably a hexafluoroisopropanol group). Furthermore, in a case where $R_6$ is a hydroxyl group, $L_3$ is preferably the (n+m+1)-valent aromatic hydrocarbon ring group.

$R_7$ represents a halogen atom. Examples of the halogen atom include a fluorine atom, a chlorine atom, a bromine atom, or an iodine atom.

m represents an integer of 1 or more. m is preferably an integer of 1 to 3 and more preferably an integer of 1 or 2.

n represents 0 or an integer of 1 or more. n is preferably an integer of 1 to 4.

Furthermore, (n+m+1) is preferably an integer of 1 to 5.

As the repeating unit having an acid group, a repeating unit represented by General Formula (I) is also preferable.

(I)

In General Formula (I), $R_{41}$, $R_{42}$, and $R_{43}$ each independently represent a hydrogen atom, an alkyl group, a cycloalkyl group, a halogen atom, a cyano group, or an alkoxycarbonyl group. It should be noted that $R_{42}$ may be bonded to $Ar_4$ to form a ring, in which case $R_{42}$ represents a single bond or an alkylene group.

$X_4$ represents a single bond, —COO—, or —CONR₆₄—, and $R_{64}$ represents a hydrogen atom or an alkyl group.

$L_4$ represents a single bond or an alkylene group.

$Ar_4$ represents an (n+1)-valent aromatic ring group, and in a case where $Ar_4$ is bonded to $R_{42}$ to form a ring, $Ar_4$ represents an (n+2)-valent aromatic ring group. n represents an integer of 1 to 5.

As the alkyl group represented by each of $R_{41}$, $R_{42}$, and $R_{43}$ in General Formula (I), an alkyl group having 20 or less carbon atoms, such as a methyl group, an ethyl group, a propyl group, an isopropyl group, an n-butyl group, a sec-butyl group, a hexyl group, a 2-ethylhexyl group, an octyl group, and a dodecyl group is preferable, an alkyl group having 8 or less carbon atoms is more preferable, and an alkyl group having 3 or less carbon atoms is still more preferable.

The cycloalkyl group of each of $R_{41}$, $R_{42}$, and $R_{43}$ in General Formula (I) may be monocyclic or polycyclic. Among those, a monocyclic cycloalkyl group having 3 to 8 carbon atoms, such as a cyclopropyl group, a cyclopentyl group, and a cyclohexyl group, is preferable.

Examples of the halogen atom of each of $R_{41}$, $R_{42}$, and $R_{43}$ in General Formula (I) include a fluorine atom, a chlorine atom, a bromine atom, and an iodine atom, and the fluorine atom is preferable.

As the alkyl group included in the alkoxycarbonyl group of each of $R_{41}$, $R_{42}$, and $R_{43}$ in General Formula (I), the same ones as the alkyl group in each of $R_{41}$, $R_{42}$, and $R_{43}$ are preferable.

Preferred examples of the substituent in each of the groups include an alkyl group, a cycloalkyl group, an aryl group, an amino group, an amide group, a ureide group, a urethane group, a hydroxyl group, a carboxyl group, a halogen atom, an alkoxy group, a thioether group, an acyl group, an acyloxy group, an alkoxycarbonyl group, a cyano group, and a nitro group. The substituent preferably has 8 or less carbon atoms.

$Ar_4$ represents an (n+1)-valent aromatic ring group. The divalent aromatic ring group in a case where n is 1 is preferably for example, an arylene group having 6 to 18 carbon atoms, such as a phenylene group, a tolylene group, a naphthylene group, and an anthracenylene group, or a divalent aromatic ring group including a heterocyclic ring such as a thiophene ring, a furan ring, a pyrrole ring, a benzothiophene ring, a benzofuran ring, a benzopyrrole ring, a triazine ring, an imidazole ring, a benzimidazole ring, a triazole ring, a thiadiazole ring, and a thiazole ring. Furthermore, the aromatic ring group may have a substituent.

Specific examples of the (n+1)-valent aromatic ring group in a case where n is an integer of 2 or more include groups formed by removing any (n−1) hydrogen atoms from the above-described specific examples of the divalent aromatic ring group.

The (n+1)-valent aromatic ring group may further have a substituent.

Examples of the substituent which can be contained in the alkyl group, the cycloalkyl group, the alkoxycarbonyl group, the alkylene group, and the (n+1)-valent aromatic ring group, each mentioned above, include the alkyl groups; the alkoxy groups such as a methoxy group, an ethoxy group, a hydroxyethoxy group, a propoxy group, a hydroxypropoxy group, and a butoxy group; the aryl groups such as a phenyl group; and the like, as mentioned for each of $R_{41}$, $R_{42}$, and $R_{43}$ in General Formula (I).

Examples of the alkyl group of $R_{64}$ in —CONR$_{64}$— represented by $X_4$ ($R_{64}$ represents a hydrogen atom or an alkyl group) include an alkyl group having 20 or less carbon atoms, such as a methyl group, an ethyl group, a propyl group, an isopropyl group, an n-butyl group, a sec-butyl group, a hexyl group, a 2-ethylhexyl group, an octyl group, and a dodecyl group, and an alkyl group having 8 or less carbon atoms, is preferable.

As $X_4$, a single bond, —COO—, or —CONH— is preferable, and the single bond or —COO— is more preferable.

As the alkylene group in $L_4$, an alkylene group having 1 to 8 carbon atoms, such as a methylene group, an ethylene group, a propylene group, a butylene group, a hexylene group, and an octylene group, is preferable.

As $Ar_4$, an aromatic ring group having 6 to 18 carbon atoms is preferable, and a benzene ring group, a naphthalene ring group, and a biphenylene ring group are more preferable.

The repeating unit represented by General Formula (I) preferably comprises a hydroxystyrene structure. That is, $Ar_4$ is preferably the benzene ring group.

The repeating unit represented by General Formula (I) is preferably a repeating unit represented by General Formula (1).

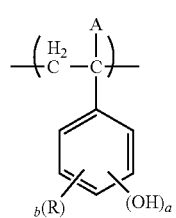

(1)

In General Formula (1),

A represents a hydrogen atom, an alkyl group, a cycloalkyl group, a halogen atom, or a cyano group.

R represents a halogen atom, an alkyl group, a cycloalkyl group, an aryl group, an alkenyl group, an aralkyl group, an alkoxy group, an alkylcarbonyloxy group, an alkylsulfonyloxy group, an alkyloxycarbonyl group, or an aryloxycarbonyl group, and in a case where a plurality of R's are present, R's may be the same as or different from each other. In a case where there are a plurality of R's, R's may be bonded to each other to form a ring. As R, the hydrogen atom is preferable.

a represents an integer of 1 to 3.

b represents an integer of 0 to (5−a).

The repeating unit having an acid group is exemplified below. In the formulae, a represents 1 or 2.

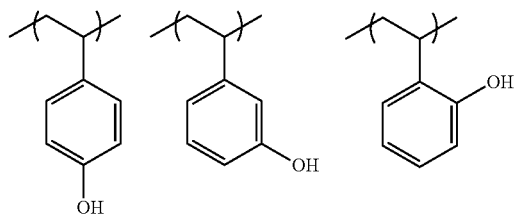

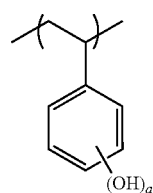

(B-1)

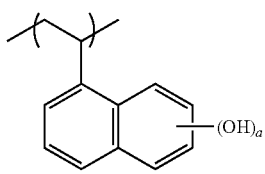

(B-2)

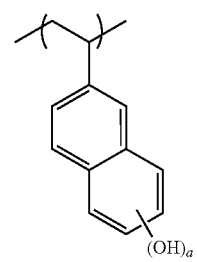

(B-3)

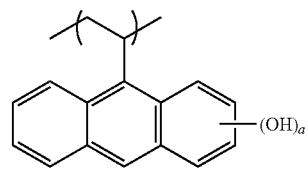

(B-4)

(B-5)

(B-6) 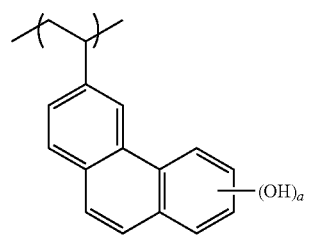
(B-7) 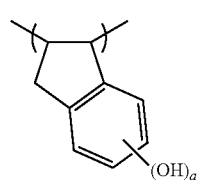
(B-8) 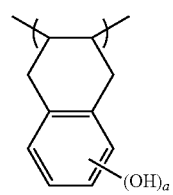
(B-9) 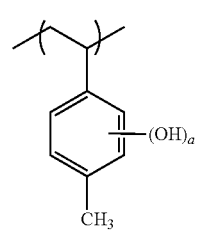
(B-10) 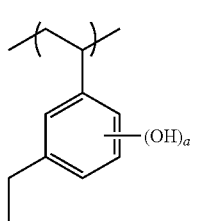
(B-11) 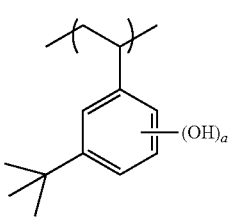
(B-12) 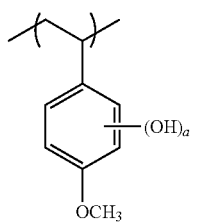
(B-13) 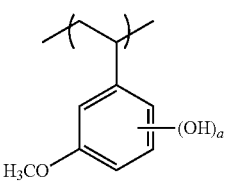
(B-14) 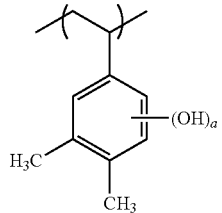
(B-15) 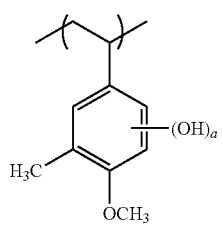
(B-16) 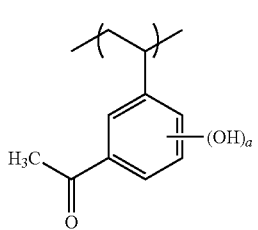
(B-17) 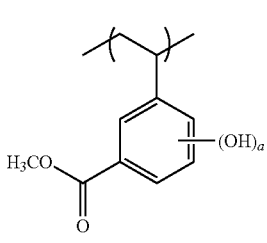
(B-18) 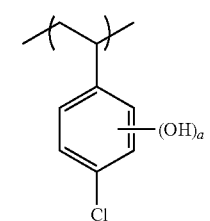
(B-19) 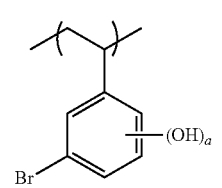

-continued (B-34) 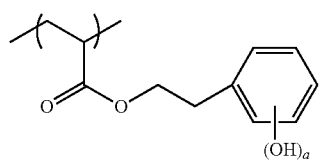 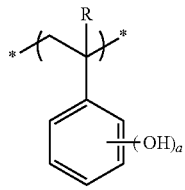
(B-35) 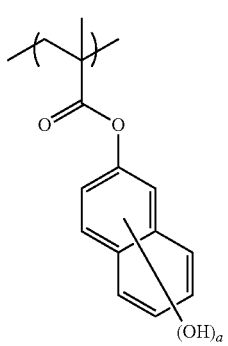 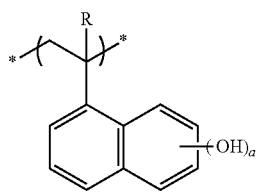 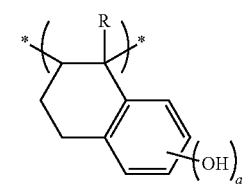
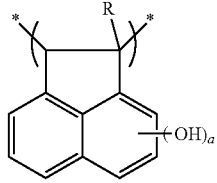
(B-36) 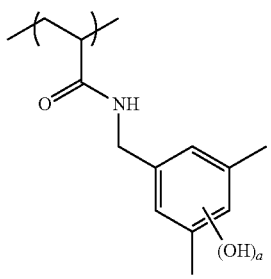 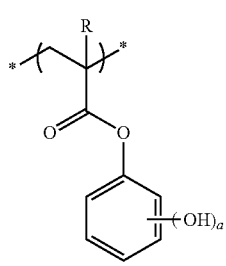 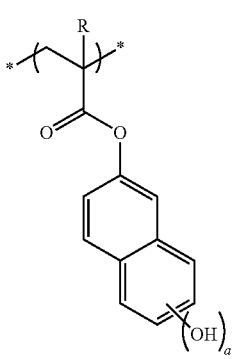
(B-37) 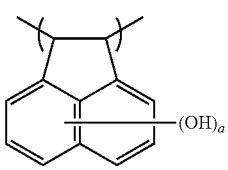
(B-38) 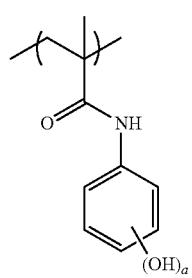 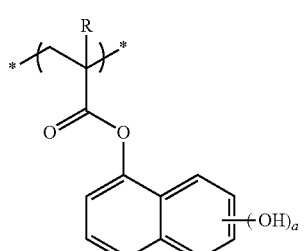
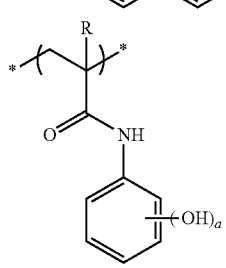
Moreover, among the repeating units, the repeating units specifically described below are preferable. In the formula, R represents a hydrogen atom or a methyl group, and a represents 2 or 3.

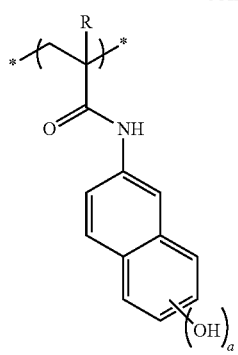
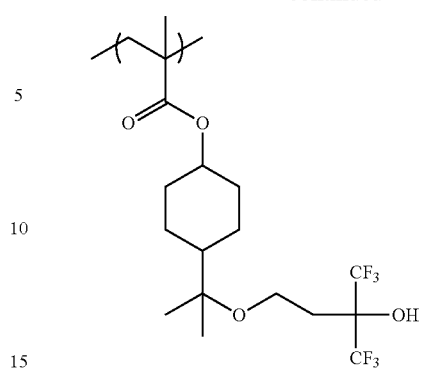
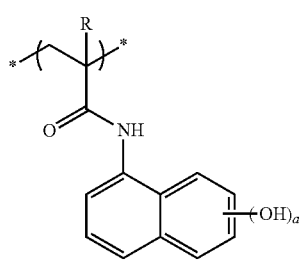
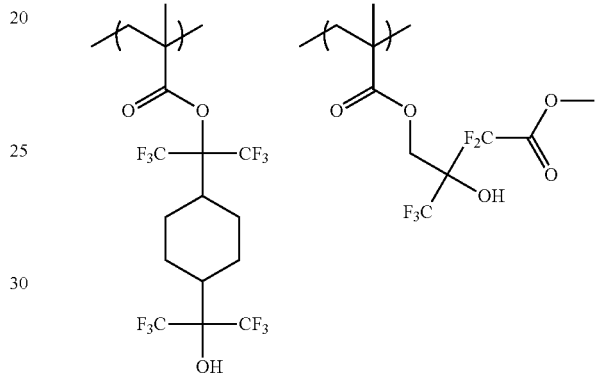
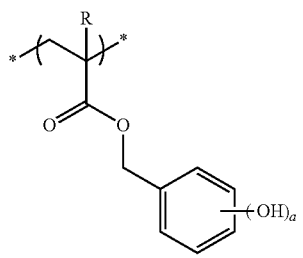
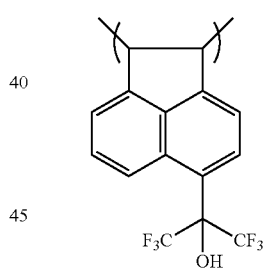
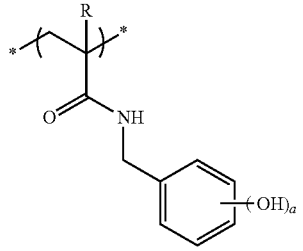
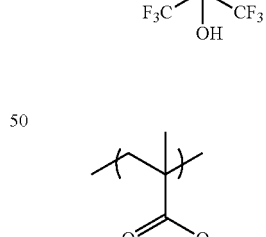
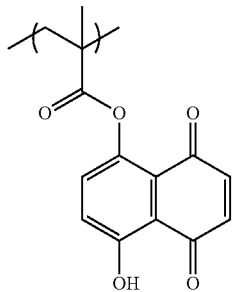
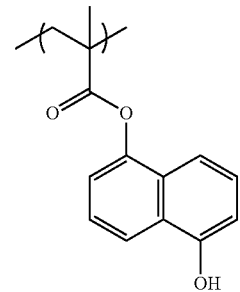
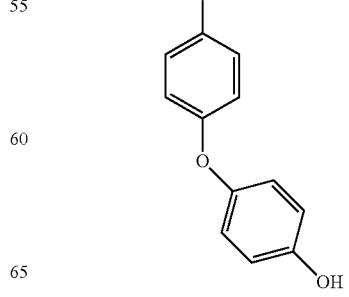

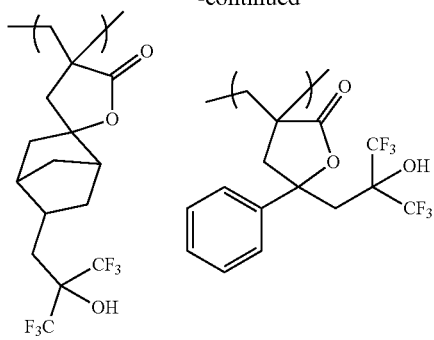

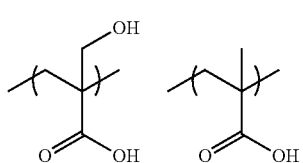

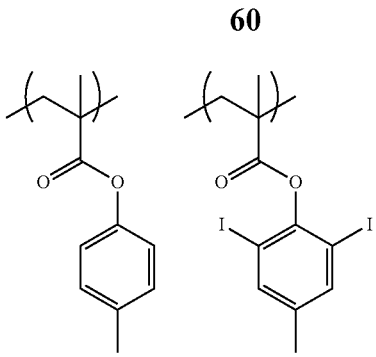

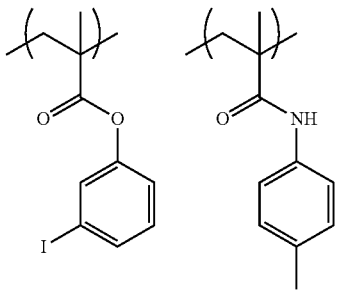

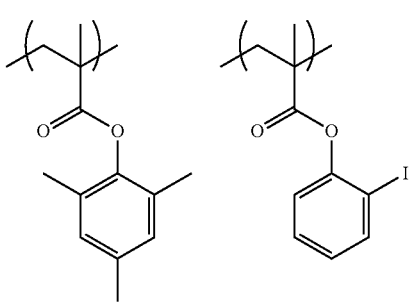

The content of the repeating unit having an acid group is preferably 10% by mole or more, and more preferably 15% by mole or more with respect to all repeating units in the resin (A). In addition, an upper limit value thereof is preferably 70% by mole or less, more preferably 65% by mole or less, and still more preferably 60% by mole or less.

<<Repeating Unit Having Fluorine Atom or Iodine Atom>>

The resin (A) may have a repeating unit having a fluorine atom or an iodine atom, in addition to "<<Repeating Unit Having Acid-Decomposable Group>>" and "<<Repeating Unit Having Acid Group>>", each mentioned above. In addition, <<Repeating Unit Having Fluorine Atom or Iodine Atom>> as mentioned herein is preferably different from other kinds of repeating units belonging to the group A, such as <<Repeating Unit Having Lactone Group, Sultone Group, or Carbonate Group>> and <<Repeating Unit Having Photoacid Generating Group>>, which will be described later.

As the repeating unit having a fluorine atom or an iodine atom, a repeating unit represented by Formula (C) is preferable.

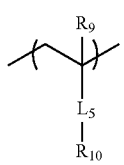

(C)

$L_5$ represents a single bond or an ester group.

$R_9$ represents a hydrogen atom, or an alkyl group which may have a fluorine atom or an iodine atom.

$R_{10}$ represents a hydrogen atom, an alkyl group which may have a fluorine atom or an iodine atom, a cycloalkyl group which may have a fluorine atom or an iodine atom, an aryl group which may have a fluorine atom or an iodine atom, or a group formed by combination thereof.

The repeating unit having a fluorine atom or an iodine atom will be exemplified below.

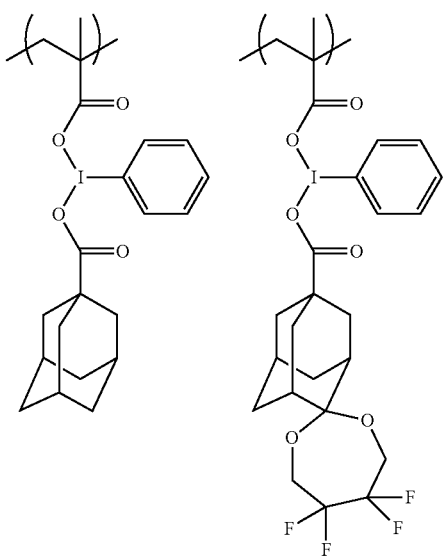

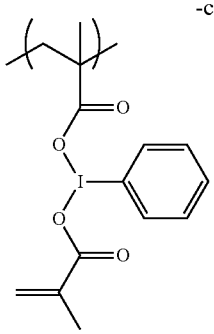

The content of the repeating unit having a fluorine atom or an iodine atom is preferably 0% by mole or more, more preferably 5% by mole or more, and still more preferably 10% by mole or more with respect to all repeating units in the resin (A). In addition, an upper limit value thereof is preferably 50% by mole or less, more preferably 45% by mole or less, and still more preferably 40% by mole or less.

Furthermore, since the repeating unit having a fluorine atom or an iodine atom does not include <<Repeating Unit Having Acid-Decomposable Group>> and <<Repeating Unit Having Acid Group>> as described above, the content of the repeating unit having a fluorine atom or an iodine atom is also intended to be the content of the repeating unit having a fluorine atom or an iodine atom excluding <<Repeating Unit Having Acid-Decomposable Group>> and <<Repeating Unit Having Acid Group>>.

The total content of the repeating units including at least one of a fluorine atom or an iodine atom in the repeating units of the resin (A) is preferably 20% by mole or more, more preferably 30% by mole or more, and still more preferably 40% by mole or more with respect to all repeating units of the resin (A). An upper limit value thereof is not particularly limited, but is, for example, 100% by mole or less.

In addition, examples of the repeating unit including at least one of a fluorine atom or an iodine atom include a repeating unit which has a fluorine atom or an iodine atom, and has an acid-decomposable group, a repeating unit which has a fluorine atom or an iodine atom, and has an acid group, and a repeating unit having a fluorine atom or an iodine atom.

<<Repeating Unit Having Lactone Group, Sultone Group, or Carbonate Group>>

The resin (A) may have a repeating unit having at least one selected from the group consisting of a lactone group, a sultone group, and a carbonate group (hereinafter also collectively referred to as a "repeating unit having a lactone group, a sultone group, or a carbonate group").

It is also preferable that the repeating unit having a lactone group, a sultone group, or a carbonate group has no acid group such as a hexafluoropropanol group.

The lactone group or the sultone group may have a lactone structure or a sultone structure. The lactone structure or the sultone structure is preferably a 5- to 7-membered ring lactone structure or a 5- to 7-membered ring sultone structure. Among those, the structure is more preferably a 5- to 7-membered ring lactone structure with which another ring structure is fused so as to form a bicyclo structure or a spiro structure or a 5- to 7-membered ring sultone structure with which another ring structure is fused so as to form a bicyclo structure or a spiro structure.

The resin (A) preferably has a repeating unit having a lactone group or a sultone group, formed by extracting one or more hydrogen atoms from a ring member atom of a lactone structure represented by any of General Formulae (LC1-1) to (LC1-21) or a sultone structure represented by any of General Formulae (SL1-1) to (SL1-3).

In addition, the lactone group or the sultone group may be bonded directly to the main chain. For example, a ring member atom of the lactone group or the sultone group may constitute the main chain of the resin (A).

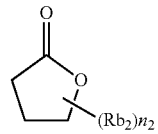

LC1-1

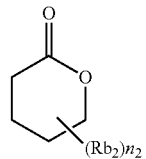

LC1-2

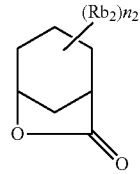

LC1-3

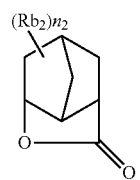

LC1-4

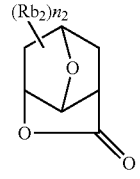

LC1-5

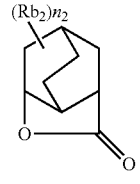

LC1-6

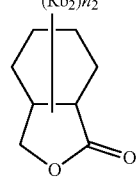

LC1-7

LC1-8 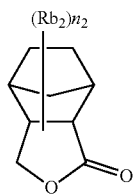
LC1-9 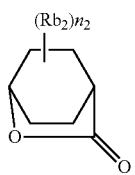
LC1-10 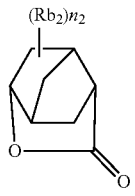
LC1-11 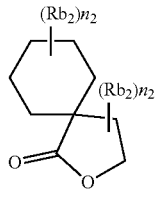
LC1-12 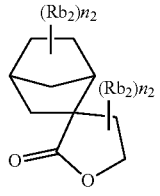
LC1-13 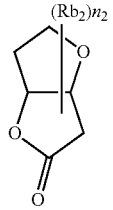
LC1-14 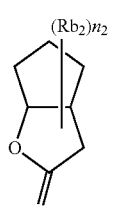
LC1-15 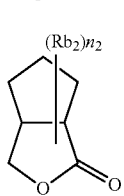
LC1-16 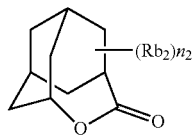
LC1-17 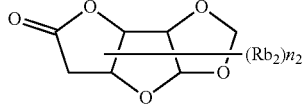
LC1-18 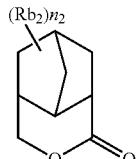
LC1-19 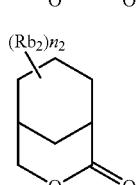
LC1-20 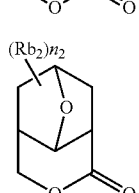
LC1-21 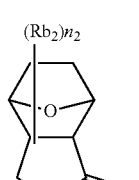
SL1-1 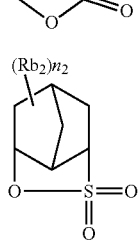
SL1-2 
SL1-3 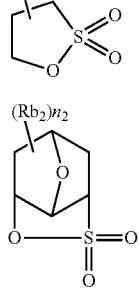
The moiety of the lactone structure or the sultone structure may have a substituent ($Rb_2$). Preferred examples of the substituent ($Rb_2$) include an alkyl group having 1 to 8 carbon atoms, a cycloalkyl group having 4 to 7 carbon atoms, an alkoxy group having 1 to 8 carbon atoms, an alkoxycarbonyl group having 1 to 8 carbon atoms, a carboxyl group, a halogen atom, a hydroxyl group, a cyano group, and an acid-decomposable group. n2 represents an integer of 0 to 4. In a case where n2 is 2 or more, $Rb_2$'s which are present in a plural number may be different from each other, and $Rb_2$'s which are present in a plural number may be bonded to each other to form a ring.

Examples of the repeating unit having a group having the lactone structure represented by any of General Formulae (LC1-1) to (LC1-21) or the sultone structure represented by any of General Formulae (SL1-1) to (SL1-3) include a repeating unit represented by General Formula (AI).

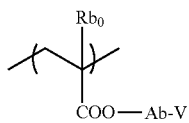

(AI)

In General Formula (AI), $Rb_0$ represents a hydrogen atom, a halogen atom, or an alkyl group having 1 to 4 carbon atoms.

Preferred examples of the substituent which may be contained in the alkyl group of $Rb_0$ include a hydroxyl group and a halogen atom.

Examples of the halogen atom of $Rb_0$ include a fluorine atom, a chlorine atom, a bromine atom, and an iodine atom. $Rb_0$ is preferably the hydrogen atom or a methyl group.

Ab represents a single bond, an alkylene group, a divalent linking group having a monocyclic or polycyclic alicyclic hydrocarbon structure, an ether group, an ester group, a carbonyl group, a carboxyl group, or a divalent group formed by combination thereof. Among those, the single bond or a linking group represented by -$Ab_1$-$CO_2$— is preferable. $Ab_1$ is a linear or branched alkylene group, or a monocyclic or polycyclic cycloalkylene group, and is preferably a methylene group, an ethylene group, a cyclohexylene group, an adamantylene group, or a norbornylene group.

V represents a group formed by extracting one hydrogen atom from a ring member atom of the lactone structure represented by any of General Formulae (LC1-1) to (LC1-21) or a group formed by extracting one hydrogen atom from a ring member atom of the sultone structure represented by any of General Formulae (SL1-1) to (SL1-3).

In a case where an optical isomer is present in the repeating unit having a lactone group or a sultone group, any of optical isomers may be used. In addition, one kind of optical isomers may be used alone or a plurality of kinds of optical isomers may be mixed and used. In a case where one kind of optical isomers is mainly used, an optical purity (ee) thereof is preferably 90 or more, and more preferably 95 or more.

As the carbonate group, a cyclic carbonic acid ester group is preferable.

As the repeating unit having a cyclic carbonic acid ester group, a repeating unit represented by General Formula (A-1) is preferable.

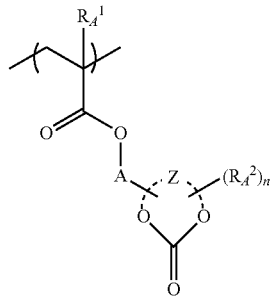

(A-1)

In General Formula (A-1), $R_A^1$ represents a hydrogen atom, a halogen atom, or a monovalent organic group (preferably a methyl group).

n represents an integer of 0 or more.

$R_A^2$ represents a substituent. In a case where n is 2 or more, $R_A^2$ which are present in a plural number may be the same as or different from each other.

A represents a single bond or a divalent linking group. As the divalent linking group, an alkylene group, a divalent linking group having a monocyclic or polycyclic alicyclic hydrocarbon structure, an ether group, an ester group, a carbonyl group, a carboxyl group, or a divalent group formed by combination thereof is preferable.

Z represents an atomic group that forms a monocycle or polycycle with a group represented by —O—CO—O— in the formula.

The repeating unit having a lactone group, a sultone group, or a carbonate group will be exemplified below.

(in the formulae, Rx represents H, $CH_3$, $CH_2OH$, or CF)

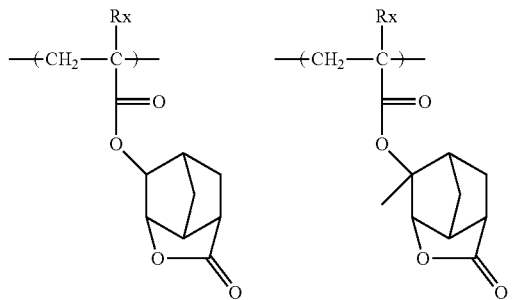

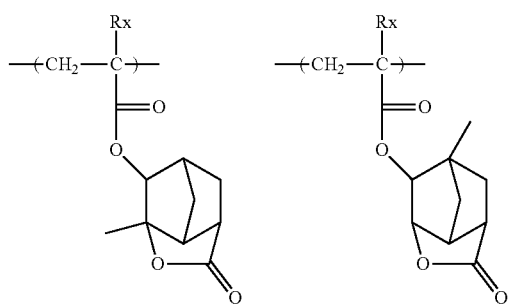

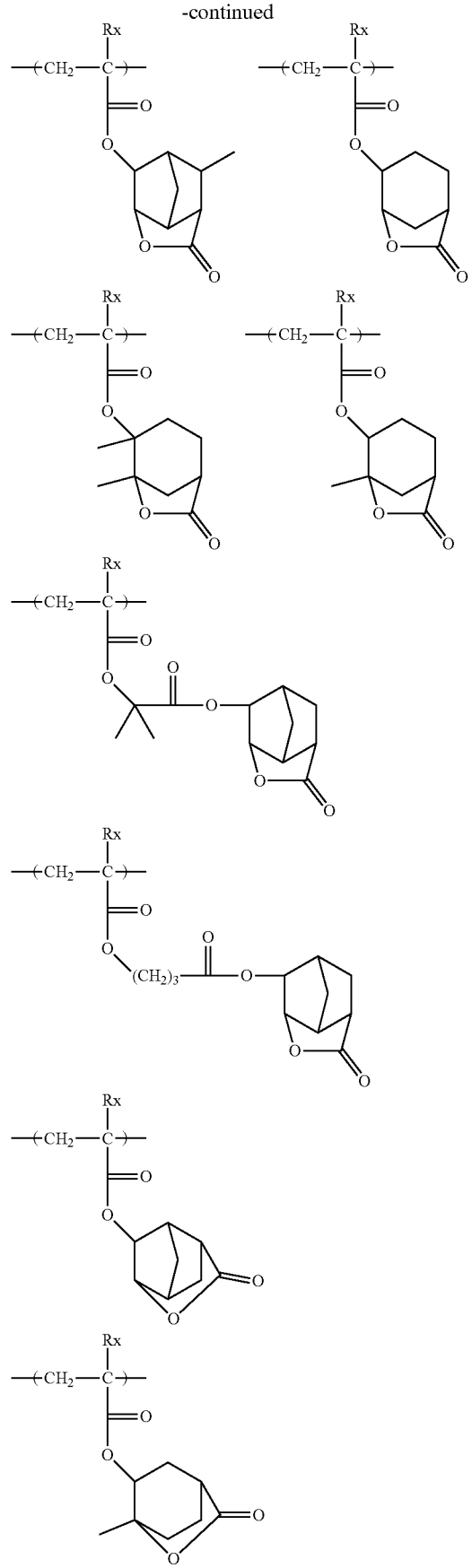
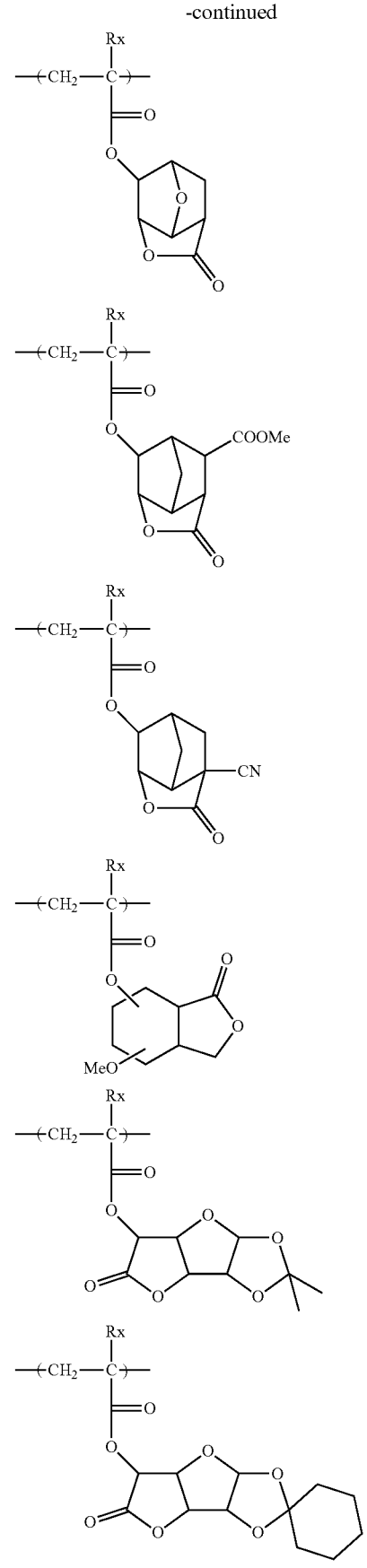

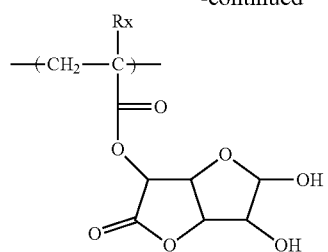
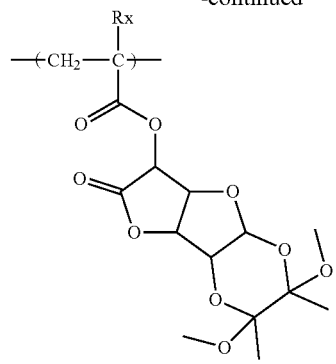
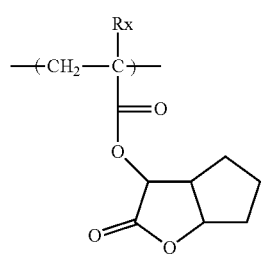
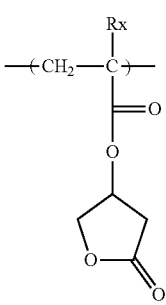
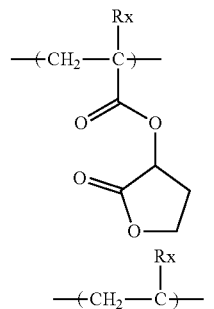
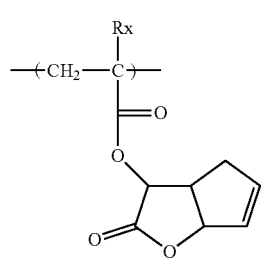
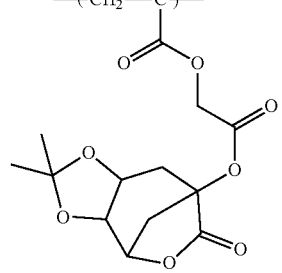
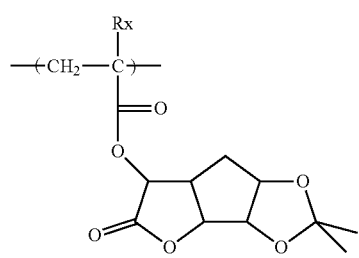
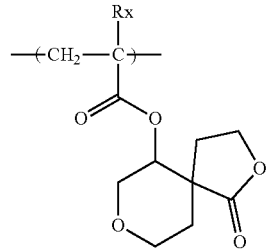
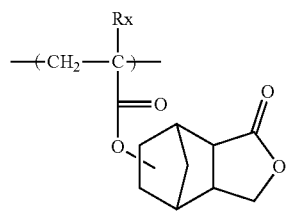
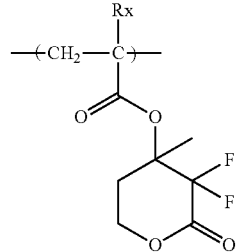
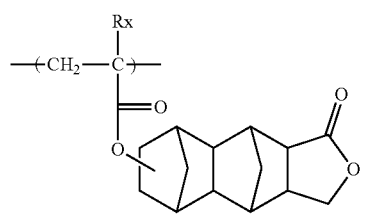
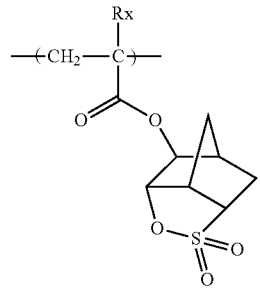
(in the formulae, Rx represents H, CH₃, CH₂OH, or CF₃)

71
-continued

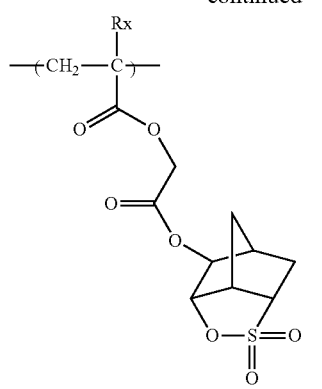

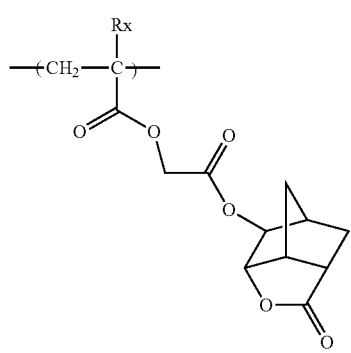

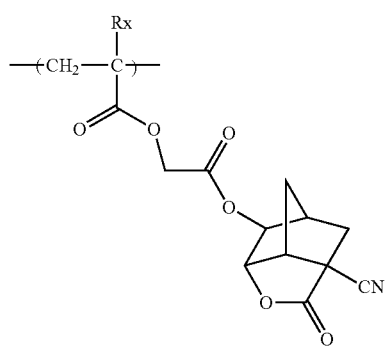

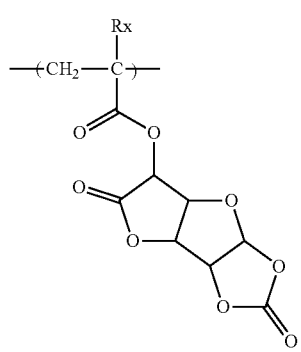

72
-continued

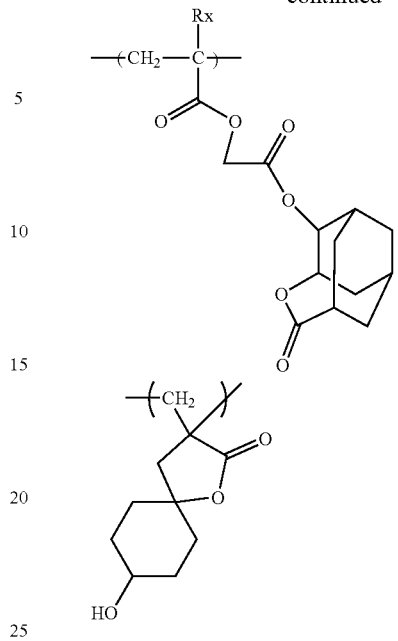

(in the formulae, Rx represents H, $CH_3$, $CH_2OH$, or $CF_3$)

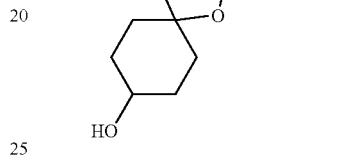

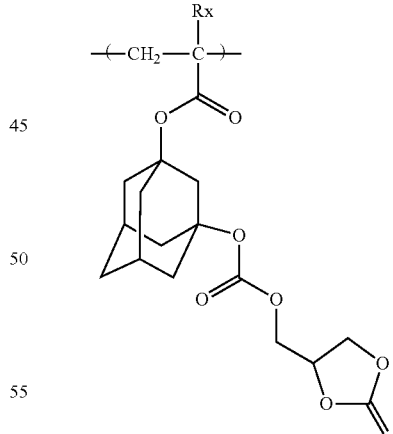

The content of the repeating unit having a lactone group, a sultone group, or a carbonate group is preferably 1% by mole or more, and more preferably 10% by mole or more with respect to all repeating units in the resin (A). In addition, an upper limit value thereof is preferably 85% by mole or less, more preferably 80% by mole or less, still more preferably 70% by mole or less, and particularly preferably 60% by mole or less.

<<Repeating Unit Having Photoacid Generating Group>>

The resin (A) may have, as a repeating unit other than those above, a repeating unit having a group that generates an acid upon irradiation with actinic rays or radiation (hereinafter also referred to as a "photoacid generating group").

In this case, it can be considered that the repeating unit having a photoacid generating group corresponds to a compound that generates an acid upon irradiation with actinic rays or radiation which will be described later (also referred to as a "photoacid generator").

Examples of such the repeating unit include a repeating unit represented by General Formula (4).

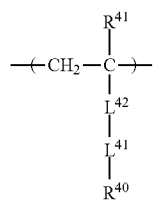
(4)

$R^{41}$ represents a hydrogen atom or a methyl group. $L^{41}$ represents a single bond or a divalent linking group. $L^{42}$ represents a divalent linking group. $R^{40}$ represents a structural moiety that decomposes upon irradiation with actinic rays or radiation to generate an acid in a side chain.

The repeating unit having a photoacid generating group is exemplified below.

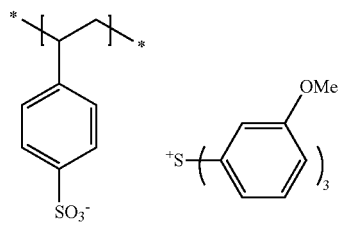

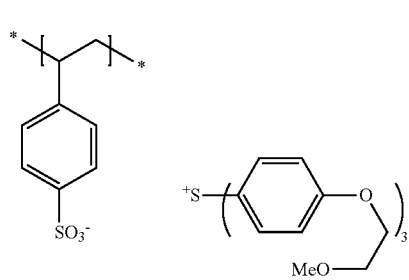

-continued

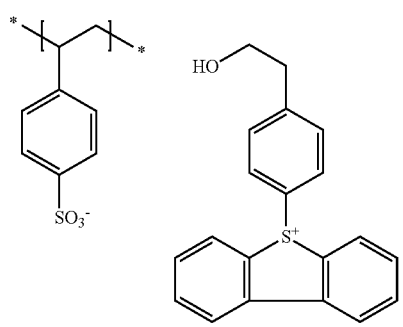

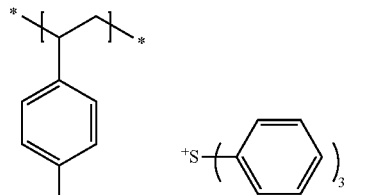

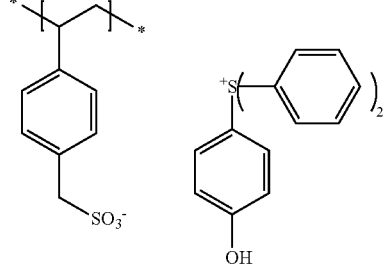

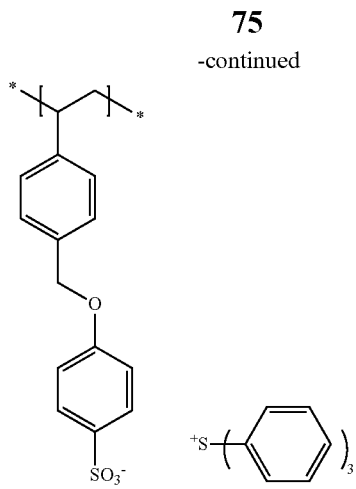
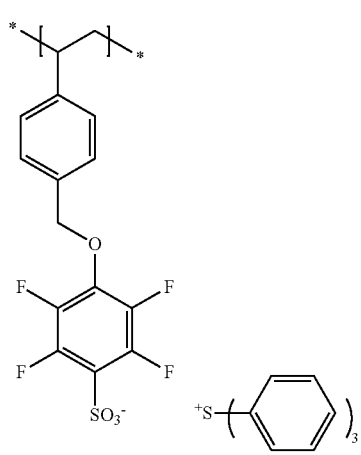
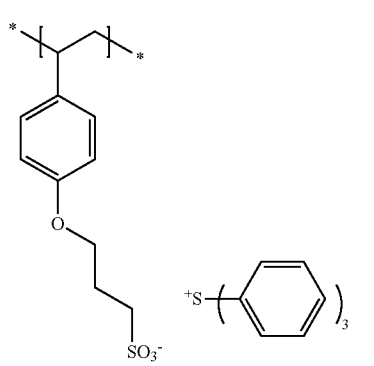
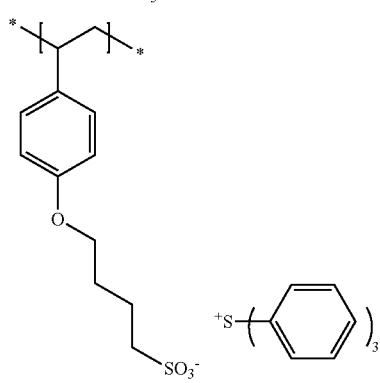

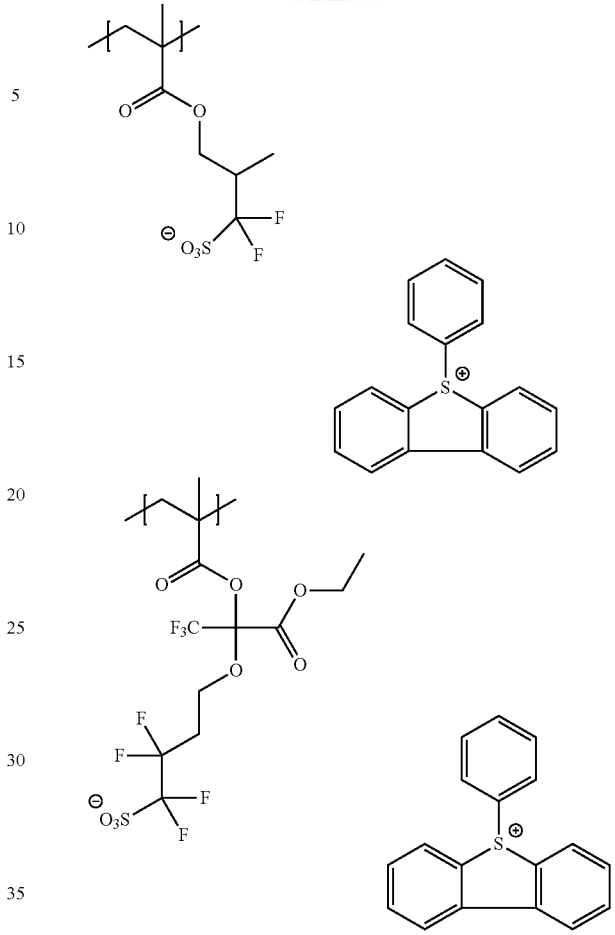

In addition, examples of the repeating unit represented by General Formula (4) include the repeating units described in paragraphs [0094] to [0105] of JP2014-041327A.

The content of the repeating unit having a photoacid generating group is preferably 1% by mole or more, and more preferably 5% by mole or more with respect to all repeating units in the resin (A). In addition, an upper limit value thereof is preferably 40% by mole or less, more preferably 35% by mole or less, and still more preferably 30% by mole or less.

<<Repeating Unit Represented by General Formula (V-1) or General Formula (V-2)>>

The resin (A) may have a repeating unit represented by General Formula (V-1) or General Formula (V-2).

The repeating unit represented by General Formula (V-1) and General Formula (V-2) is preferably a repeating unit different from the above-mentioned repeating units.

(V-1)

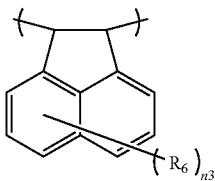

(V-2)

In the formulae, $R_6$ and $R_7$ each independently represent a hydrogen atom, a hydroxyl group, an alkyl group, an alkoxy group, an acyloxy group, a cyano group, a nitro group, an amino group, a halogen atom, an ester group (—OCOR or —COOR: R is an alkyl group or fluorinated alkyl group having 1 to 6 carbon atoms), or a carboxyl group. As the alkyl group, a linear, branched, or cyclic alkyl group having 1 to 10 carbon atoms is preferable.

n3 represents an integer of 0 to 6.

n4 represents an integer of 0 to 4.

$X^4$ is a methylene group, an oxygen atom, or a sulfur atom.

The repeating unit represented by General Formula (V-1) or (V-2) will be exemplified below.

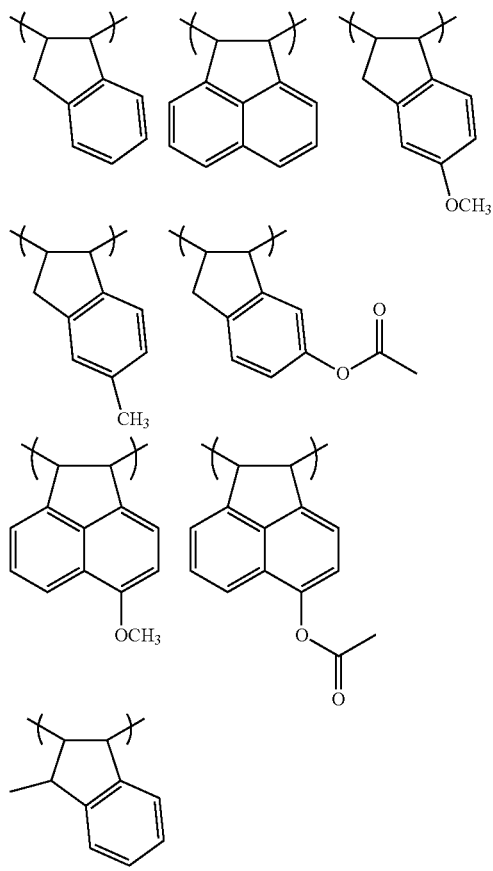

<<Repeating Unit for Reducing Motility of Main Chain>>

The resin (A) preferably has a high glass transition temperature (Tg) from the viewpoint that excessive diffusion of an acid generated or pattern collapse during development can be suppressed. Tg is preferably higher than 90° C., more preferably higher than 100° C., still more preferably higher than 110° C., and particularly preferably higher than 125° C. In addition, since an excessive increase in Tg causes a decrease in the dissolution rate in a developer, Tg is preferably 400° C. or lower, and more preferably 350° C. or lower.

Furthermore, in the present specification, the glass transition temperature (Tg) of a polymer such as the resin (A) is calculated by the following method. First, the Tg of a homopolymer consisting only of each repeating unit included in the polymer is calculated by a Bicerano method. Hereinafter, the calculated Tg is referred to as the "Tg of the repeating unit". Next, the mass proportion (%) of each repeating unit to all repeating units in the polymer is calculated. Then, the Tg at each mass proportion is calculated using a Fox's equation (described in Materials Letters 62 (2008) 3152, and the like), and these are summed to obtain the Tg (° C.) of the polymer.

The Bicerano method is described in Prediction of polymer properties, Marcel Dekker Inc., New York (1993), and the like. The calculation of a Tg by the Bicerano method can be carried out using MDL Polymer (MDL Information Systems, Inc.), which is software for estimating physical properties of a polymer.

In order to raise the Tg of the resin (A) (preferably to raise the Tg to higher than 90° C.), it is preferable to reduce the motility of the main chain of the resin (A). Examples of a method for reducing the motility of the main chain of the resin (A) include the following (a) to (e) methods.

(a) Introduction of a bulky substituent into the main chain
(b) Introduction of a plurality of substituents into the main chain
(c) Introduction of a substituent that induces an interaction between the resins (A) near the main chain
(d) Formation of the main chain in a cyclic structure
(e) Linking of a cyclic structure to the main chain Furthermore, the resin (A) preferably has a repeating unit having a Tg of a homopolymer exhibiting 130° C. or higher.

In addition, the type of the repeating unit having a Tg of the homopolymer exhibiting 130° C. or higher is not particularly limited, and may be any of repeating units having a Tg of a homopolymer of 130° C. or higher calculated by the Bicerano method. Moreover, it corresponds to a repeating unit having a Tg of a homopolymer exhibiting 130° C. or higher, depending on the type of a functional group in the repeating units represented by Formula (A) to Formula (E) which will be described later.

(Repeating Unit Represented by Formula (A))

As an example of a specific unit for accomplishing (a) above, a method of introducing a repeating unit represented by Formula (A) into the resin (A) may be mentioned.

(A)

In Formula (A), $R_A$ represents a group having a polycyclic structure. Rx represents a hydrogen atom, a methyl group, or an ethyl group. The group having a polycyclic structure is a group having a plurality of ring structures, and the plurality of ring structures may or may not be fused.

Specific examples of the repeating unit represented by Formula (A) include the following repeating units.

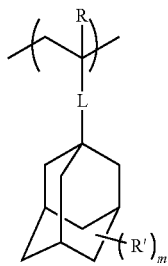 (A-1)

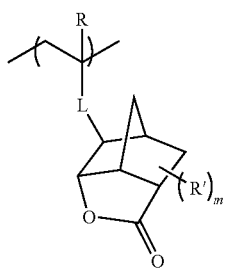 (A-2)

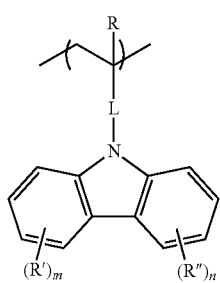 (A-3)

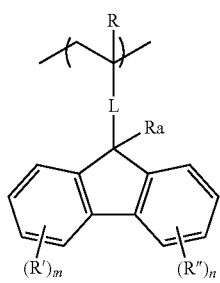 (A-4)

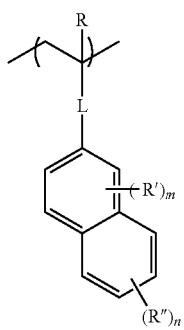 (A-5)

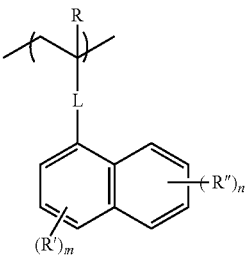 (A-6)

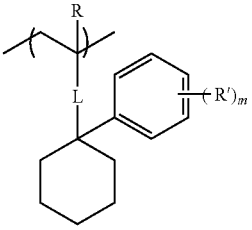 (A-7)

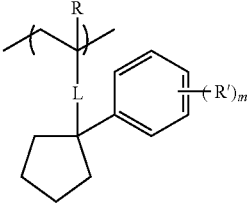 (A-8)

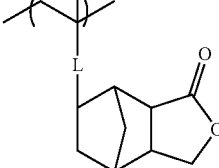 (A-9)

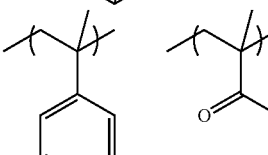
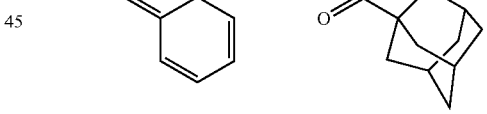

In the formulae, R represents a hydrogen atom, a methyl group, or an ethyl group.

Ra represents a hydrogen atom, an alkyl group, a cycloalkyl group, an aryl group, an aralkyl group, an alkenyl group, a hydroxyl group, an alkoxy group, an acyloxy group, a cyano group, a nitro group, an amino group, a halogen atom, an ester group (—OCOR''' or —COOR''': R''' is an alkyl group or fluorinated alkyl group having 1 to 20 carbon atoms), or a carboxyl group. Furthermore, the alkyl group, the cycloalkyl group, the aryl group, the aralkyl group, and the alkenyl group may each have a substituent. In addition, a hydrogen atom bonded to the carbon atom in the group represented by Ra may be substituted with a fluorine atom or an iodine atom.

Moreover, R' and R'' each independently represent an alkyl group, a cycloalkyl group, an aryl group, an aralkyl group, an alkenyl group, a hydroxyl group, an alkoxy group, an acyloxy group, a cyano group, a nitro group, an amino group, a halogen atom, an ester group (—OCOR''' or —COOR''': R''' is an alkyl group or fluorinated alkyl group having 1 to 20 carbon atoms), or a carboxyl group. Furthermore, the alkyl group, the cycloalkyl group, the aryl group, the aralkyl group, and the alkenyl group may each have a substituent. In addition, a hydrogen atom bonded to the carbon atom in the groups represented by each of R' and R" may be substituted with a fluorine atom or an iodine atom.

L represents a single bond or a divalent linking group. Examples of the divalent linking group include —COO—, —CO—, —O—, —S—, —SO—, —SO$_2$—, an alkylene group, a cycloalkylene group, an alkenylene group, and a linking group in which a plurality of these groups are linked. m and n each independently represent an integer of 0 or more. An upper limit of each of n and n is not particularly limited, but is 2 or less in many cases, and 1 or less in more cases.

(Repeating Unit Represented by Formula (B))

As an example of a specific unit for accomplishing (b) above, a method of introducing a repeating unit represented by Formula (B) into the resin (A) may be mentioned.

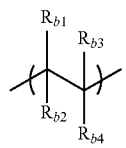

(B)

In Formula (B), $R_{b1}$ to $R_{b4}$ each independently represent a hydrogen atom or an organic group, and at least two or more of $R_{b1}$, . . . , or $R_{b4}$ represent an organic group.

Furthermore, in a case where at least one of the organic groups is a group in which a ring structure is directly linked to the main chain in the repeating unit, the types of the other organic groups are not particularly limited.

In addition, in a case where none of the organic groups is a group in which a ring structure is directly linked to the main chain in the repeating unit, at least two or more of the organic groups are substituents having three or more constituent atoms excluding hydrogen atoms.

Specific examples of the repeating unit represented by Formula (B) include the following repeating units.

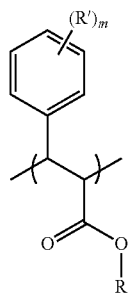

(B-1)

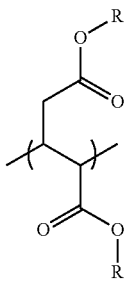

(B-2)

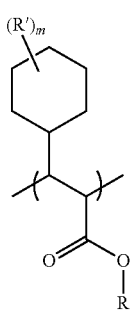

(B-3)

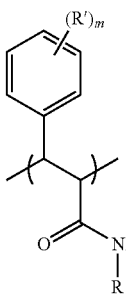

(B-4)

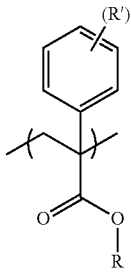

(B-5)

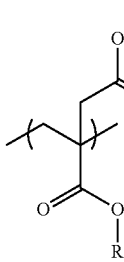

(B-6)

In the formula, R's each independently represent a hydrogen atom or an organic group. Examples of the organic group include an organic group such as an alkyl group, a cycloalkyl group, an aryl group, an aralkyl group, and an alkenyl group, each of which may have a substituent.

R"s each independently represent an alkyl group, a cycloalkyl group, an aryl group, an aralkyl group, an alkenyl group, a hydroxyl group, an alkoxy group, an acyloxy group, a cyano group, a nitro group, an amino group, a halogen atom, an ester group (—OCOR" or —COOR": R" is an alkyl group or fluorinated alkyl group having 1 to 20 carbon atoms), or a carboxyl group. Furthermore, the alkyl group, the cycloalkyl group, the aryl group, the aralkyl group, and the alkenyl group may each have a substituent. In addition, a hydrogen atom bonded to the carbon atom in the group represented by R' may be substituted with a fluorine atom or an iodine atom. m represents an integer of 0 or more. An upper limit of m is not particularly limited, but is 2 or less in many cases, and 1 or less in more cases.

(Repeating Unit Represented by Formula (C))

As an example of a specific unit for accomplishing (c) above, a method of introducing a repeating unit represented by Formula (C) into the resin (A) may be mentioned.

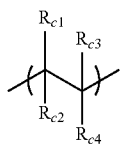
(C)

In Formula (C), $R_{c1}$ to $R_{c4}$ each independently represent a hydrogen atom or an organic group, and at least one of $R_{c1}, \ldots,$ or $R_{c4}$ is a group having a hydrogen-bonding hydrogen atom with a number of atoms of 3 or less from the main chain carbon. Among those, it is preferable that the group has hydrogen-bonding hydrogen atoms with a number of atoms of 2 or less (on a side closer to the vicinity of the main chain) to induce an interaction between the main chains of the resin (A).

Specific examples of the repeating unit represented by Formula (C) include the following repeating units.

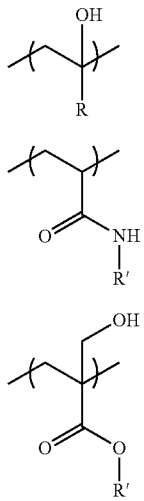

(C-1)

(C-2)

(C-3)

In the formula, R represents an organic group. Examples of the organic group include an alkyl group, a cycloalkyl group, an aryl group, an aralkyl group, an alkenyl group, and an ester group (—OCOR or —COOR: R represents an alkyl group or fluorinated alkyl group having 1 to 20 carbon atoms), each of which may have a substituent.

R' represents a hydrogen atom or an organic group. Examples of the organic group include an organic group such as an alkyl group, a cycloalkyl group, an aryl group, an aralkyl group, and an alkenyl group. In addition, a hydrogen atom in the organic group may be substituted with a fluorine atom or an iodine atom.

(Repeating Unit Represented by Formula (D))

As an example of a specific unit for accomplishing (d) above, a method of introducing a repeating unit represented by Formula (D) into the resin (A) may be mentioned.

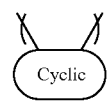
(D)

In Formula (D), "Cyclic" is a group that forms a main chain with a cyclic structure. The number of the ring-constituting atoms is not particularly limited.

Specific examples of the repeating unit represented by Formula (D) include the following repeating units.

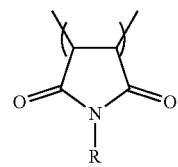
(D-1)

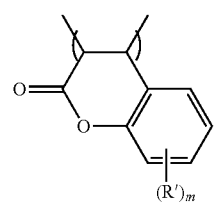
(D-2)

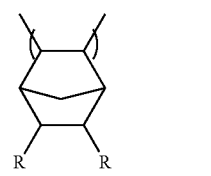
(D-3)

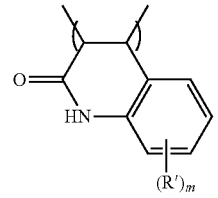
(D-4)

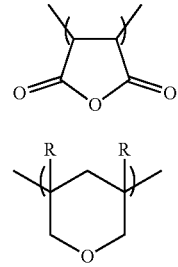
(D-5)

(D-6)

-continued (D-7) 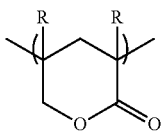

(D-8) 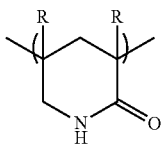

(D-9) 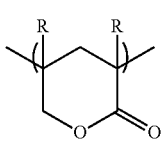

(D-10) 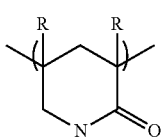

(D-11) 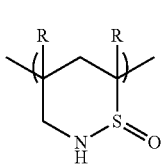

(D-12) 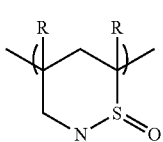

(D-13) 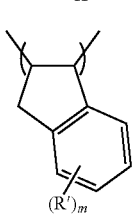

(D-14) 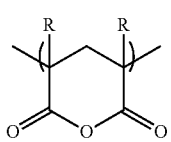

(D-15) 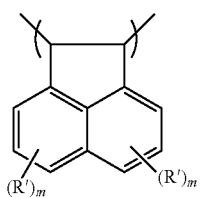

(D-16) 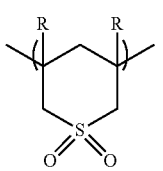

-continued (D-17) 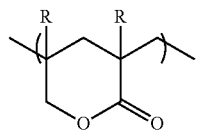

(D-18) 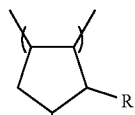

(D-19) 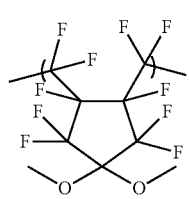

In the formula, R's each independently represent a hydrogen atom, an alkyl group, a cycloalkyl group, an aryl group, an aralkyl group, an alkenyl group, a hydroxyl group, an alkoxy group, an acyloxy group, a cyano group, a nitro group, an amino group, a halogen atom, an ester group (—OCOR" or —COOR": R" is an alkyl group or fluorinated alkyl group having 1 to 20 carbon atoms), or a carboxyl group. Furthermore, the alkyl group, the cycloalkyl group, the aryl group, the aralkyl group, and the alkenyl group may each have a substituent. In addition, the hydrogen atom bonded to the carbon atom in the group represented by R may be substituted with a fluorine atom or an iodine atom.

In the formula, R"s each independently represent an alkyl group, a cycloalkyl group, an aryl group, an aralkyl group, an alkenyl group, a hydroxyl group, an alkoxy group, an acyloxy group, a cyano group, a nitro group, an amino group, a halogen atom, an ester group (—OCOR" or —COOR": R" is an alkyl group or fluorinated alkyl group having 1 to 20 carbon atoms), or a carboxyl group. Furthermore, the alkyl group, the cycloalkyl group, the aryl group, the aralkyl group, and the alkenyl group may each have a substituent. In addition, a hydrogen atom bonded to the carbon atom in the group represented by R' may be substituted with a fluorine atom or an iodine atom. m represents an integer of 0 or more. An upper limit of m is not particularly limited, but is 2 or less in many cases, and 1 or less in more cases.

(Repeating Unit Represented by Formula (E))

As an example of a specific unit for accomplishing (e) above, a method of introducing a repeating unit represented by Formula (E) into the resin (A) may be mentioned.

(E) 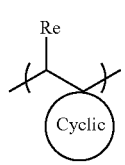

In Formula (E), Re's each independently represent a hydrogen atom or an organic group. Examples of the organic group include an alkyl group, a cycloalkyl group, an aryl group, an aralkyl group, and an alkenyl group, which may have a substituent.

"Cyclic" is a cyclic group including a carbon atom of the main chain. The number of atoms included in the cyclic group is not particularly limited.

Specific examples of the repeating unit represented by Formula (E) include the following repeating units.

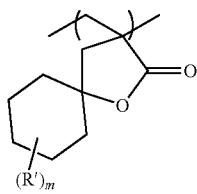
(E-1)

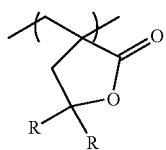
(E-2)

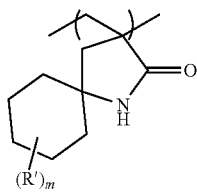
(E-3)

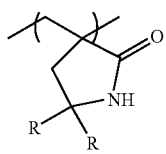
(E-4)

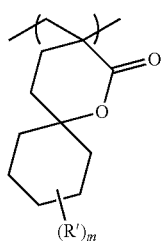
(E-5)

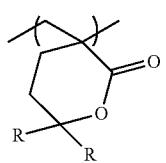
(E-6)

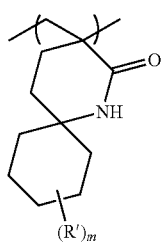
(E-7)

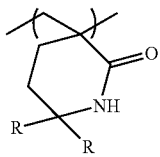
(E-8)

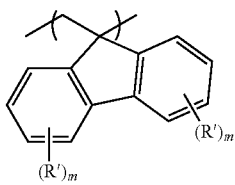
(E-9)

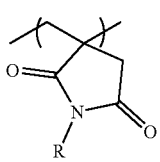
(E-10)

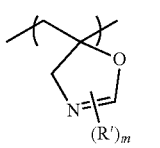
(E-11)

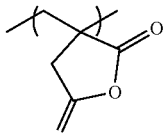
(E-12)

In the formula, R's each independently represent a hydrogen atom, an alkyl group, a cycloalkyl group, an aryl group, an aralkyl group, an alkenyl group, a hydroxyl group, an alkoxy group, an acyloxy group, a cyano group, a nitro group, an amino group, a halogen atom, an ester group (—OCOR" or —COOR": R" is an alkyl group or fluorinated alkyl group having 1 to 20 carbon atoms), or a carboxyl group. Furthermore, the alkyl group, the cycloalkyl group, the aryl group, the aralkyl group, and the alkenyl group may each have a substituent. In addition, the hydrogen atom bonded to the carbon atom in the group represented by R may be substituted with a fluorine atom or an iodine atom.

R"s each independently represent a hydrogen atom, an alkyl group, a cycloalkyl group, an aryl group, an aralkyl group, an alkenyl group, a hydroxyl group, an alkoxy group, an acyloxy group, a cyano group, a nitro group, an amino group, a halogen atom, an ester group (—OCOR" or —COOR": R" is an alkyl group or fluorinated alkyl group having 1 to 20 carbon atoms), or a carboxyl group. Furthermore, the alkyl group, the cycloalkyl group, the aryl group, the aralkyl group, and the alkenyl group may each have a substituent. In addition, a hydrogen atom bonded to the carbon atom in the group represented by R' may be substituted with a fluorine atom or an iodine atom.

m represents an integer of 0 or more. An upper limit of m is not particularly limited, but is 2 or less in many cases, and 1 or less in more cases.

In addition, in Formula (E-2), Formula (E-4), Formula (E-6), and Formula (E-8), two R's may be bonded to each other to form a ring.

The content of the repeating unit represented by Formula (E) is preferably 5% by mole or more, and more preferably 10% by mole or more with respect to all repeating units in the resin (A). In addition, an upper limit value thereof is preferably 60% by mole or less, and more preferably 55% by mole or less.

<<Repeating Unit Having at Least One Group selected from Lactone Group, Sultone Group, Carbonate Group, Hydroxyl Group, Cyano Group, or Alkali-Soluble Group>>

The resin (A) may have a repeating unit having at least one group selected from a lactone group, a sultone group, a carbonate group, a hydroxyl group, a cyano group, or an alkali-soluble group.

Examples of the repeating unit having a lactone group, a sultone group, or a carbonate group contained in the resin (A) include the repeating units described in <<Repeating Unit Having Lactone Group, Sultone Group, or Carbonate Group>> mentioned above. A preferred content thereof is also the same as described in "<<Repeating Unit Having Lactone Group, Sultone Group, or Carbonate Group>>" mentioned above.

The resin (A) may have a repeating unit having a hydroxyl group or a cyano group. As a result, the adhesiveness to a substrate and the affinity for a developer are improved.

The repeating unit having a hydroxyl group or a cyano group is preferably a repeating unit having an alicyclic hydrocarbon structure substituted with a hydroxyl group or a cyano group.

The repeating unit having a hydroxyl group or a cyano group preferably has no acid-decomposable group. Examples of the repeating unit having a hydroxyl group or a cyano group include repeating units represented by General Formulae (AIIa) to (AIId).

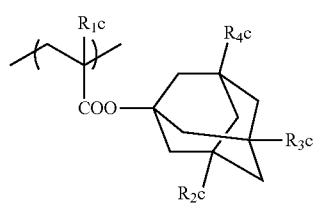

(AIIa)

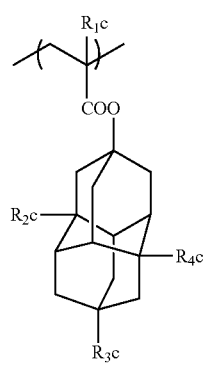

(AIIb)

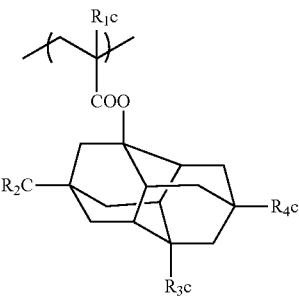

(AIIc)

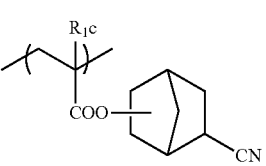

(AIId)

In General Formulae (AIIa) to (AIId), $R_{1c}$ represents a hydrogen atom, a methyl group, a trifluoromethyl group, or a hydroxymethyl group.

$R_{2c}$ to $R_{4c}$ each independently represent a hydrogen atom, a hydroxyl group, or a cyano group. It should be noted that at least one of $R_{2c}$, . . . , or $R_{4c}$ represents a hydroxyl group or a cyano group. It is preferable that one or two of $R_{2c}$ to $R_{4c}$ are hydroxyl groups, and the rest are hydrogen atoms. It is more preferable that two of $R_{2c}$ to $R_{4c}$ are hydroxyl groups and the rest are hydrogen atoms.

The content of the repeating unit having a hydroxyl group or a cyano group is preferably 5% by mole or more, and more preferably 10% by mole or more with respect to all repeating units in the resin (A). In addition, an upper limit value thereof is preferably 40% by mole or less, more preferably 35% by mole or less, and still more preferably 30% by mole or less.

Specific examples of the repeating unit having a hydroxyl group or a cyano group are shown below, but the present invention is not limited thereto.

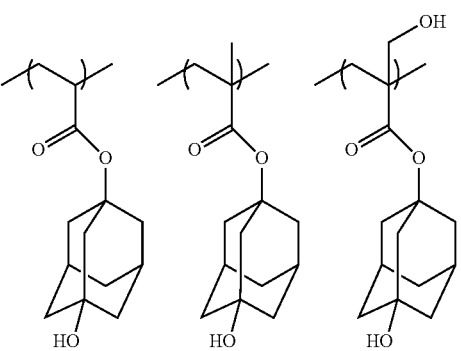

-continued

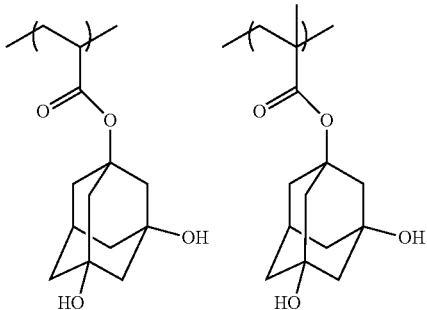

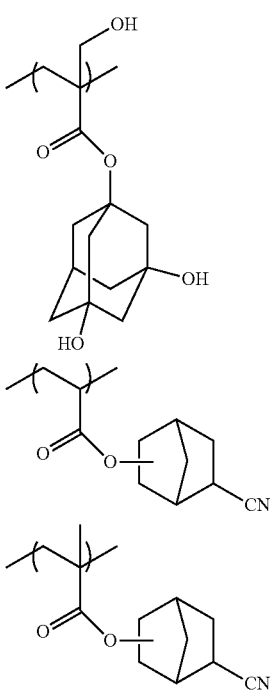

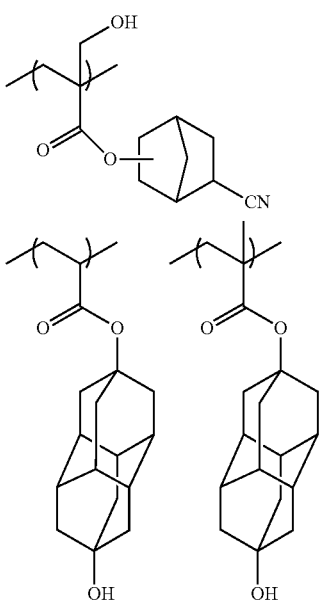

-continued

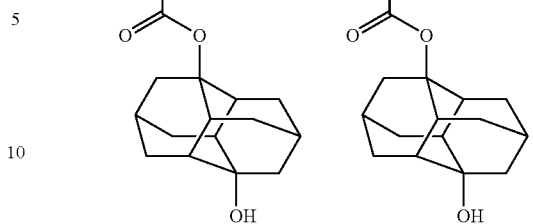

The resin (A) may have a repeating unit having an alkali-soluble group.

Examples of the alkali-soluble group include a carboxyl group, a sulfonamide group, a sulfonylimide group, a bis-sulfonylimide group, or an aliphatic alcohol group (for example, a hexafluoroisopropanol group) in which the α-position is substituted with an electron-withdrawing group, and the carboxyl group is preferable. In a case where the resin (A) includes a repeating unit having an alkali-soluble group, the resolution for use in contact holes increases.

Examples of the repeating unit having an alkali-soluble group include a repeating unit in which an alkali-soluble group is directly bonded to the main chain of a resin such as a repeating unit with acrylic acid and methacrylic acid, or a repeating unit in which an alkali-soluble group is bonded to the main chain of the resin through a linking group. Furthermore, the linking group may have a monocyclic or polycyclic cyclic hydrocarbon structure.

The repeating unit having an alkali-soluble group is preferably a repeating unit with acrylic acid or methacrylic acid.

The content of the repeating unit having an alkali-soluble group is preferably 0% by mole or more, more preferably 3% by mole or more, and still more preferably 5% by mole or more with respect to all repeating units in the resin (A). An upper limit value thereof is preferably 20% by mole or less, more preferably 15% by mole or less, and still more preferably 10% by mole or less.

Specific examples of the repeating unit having an alkali-soluble group are shown below, but the present invention is not limited thereto. In the specific examples, Rx represents H, $CH_3$, $CH_2OH$, or $CF_3$.

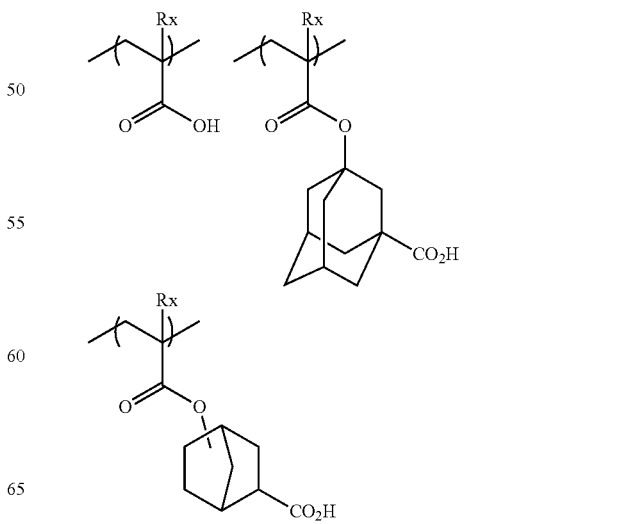

-continued

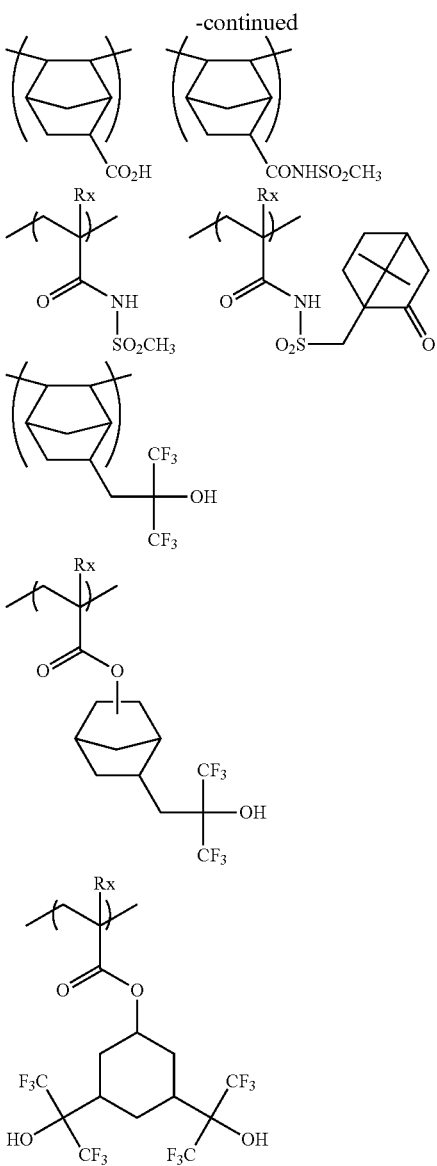

As the repeating unit having at least one group selected from a lactone group, a hydroxyl group, a cyano group, or an alkali-soluble group, a repeating unit having at least two selected from a lactone group, a hydroxyl group, a cyano group, or an alkali-soluble group is preferable, a repeating unit having a cyano group and a lactone group is more preferable, and a repeating unit having a structure in which a cyano group is substituted in the lactone structure represented by General Formula (LC1-4) is still more preferable.

<<Repeating Unit Having Alicyclic Hydrocarbon Structure and Not Exhibiting Acid Decomposability>>

The resin (A) may have a repeating unit having an alicyclic hydrocarbon structure and not exhibiting acid decomposability. This can reduce the elution of low-molecular-weight components from the resist film into an immersion liquid during liquid immersion exposure. Examples of such the repeating unit include repeating units derived from 1-adamantyl (meth)acrylate, diamantyl (meth)acrylate, tricyclodecanyl (meth)acrylate, and cyclohexyl (meth)acrylate.

<<Repeating Unit Represented by General Formula (III) Having Neither Hydroxyl Group Nor Cyano Group>>

The resin (A) may have a repeating unit represented by General Formula (III), which has neither a hydroxyl group nor a cyano group.

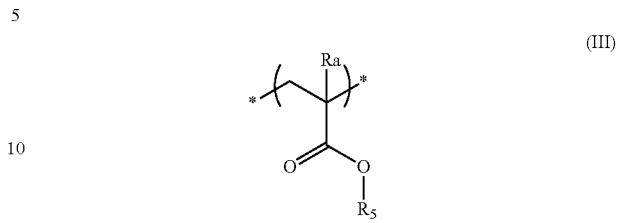

In General Formula (III), $R_5$ represents a hydrocarbon group having at least one cyclic structure and having neither a hydroxyl group nor a cyano group.

Ra represents a hydrogen atom, an alkyl group, or a —$CH_2$—O—$Ra_2$ group. In the formula, $Ra_2$ represents a hydrogen atom, an alkyl group, or an acyl group.

The cyclic structure contained in $R_5$ includes a monocyclic hydrocarbon group and a polycyclic hydrocarbon group. Examples of the monocyclic hydrocarbon group include a cycloalkyl group having 3 to 12 carbon atoms (more preferably 3 to 7 carbon atoms) or a cycloalkenyl group having 3 to 12 carbon atoms.

Examples of the polycyclic hydrocarbon group include a ring-assembled hydrocarbon group and a crosslinked cyclic hydrocarbon group.

Examples of the crosslinked cyclic hydrocarbon ring include a bicyclic hydrocarbon ring, a tricyclic hydrocarbon ring, and a tetracyclic hydrocarbon ring. Furthermore, examples of the crosslinked cyclic hydrocarbon ring also include a fused ring formed by fusing a plurality of 5- to 8-membered cycloalkane rings.

As the crosslinked cyclic hydrocarbon group, a norbornyl group, an adamantyl group, a bicyclooctanyl group, or a tricyclo[5,2,1,0$^{2,6}$]decanyl group is preferable, and the norbornyl group or the adamantyl group is more preferable.

The alicyclic hydrocarbon group may have a substituent, and examples of the substituent include a halogen atom, an alkyl group, a hydroxyl group protected by a protective group, and an amino group protected by a protective group.

The halogen atom is preferably a bromine atom, a chlorine atom, or a fluorine atom.

As the alkyl group, a methyl group, an ethyl group, a butyl group, or a t-butyl group is preferable. The alkyl group may further have a substituent, and examples of the substituent include a halogen atom, an alkyl group, a hydroxyl group protected by a protective group, and an amino group protected by a protective group.

Examples of the protective group include an alkyl group, a cycloalkyl group, an aralkyl group, a substituted methyl group, a substituted ethyl group, an alkoxycarbonyl group, and an aralkyloxycarbonyl group.

As the alkyl group, an alkyl group having 1 to 4 carbon atoms is preferable.

As the substituted methyl group, a methoxymethyl group, a methoxythiomethyl group, a benzyloxymethyl group, a t-butoxymethyl group, or a 2-methoxyethoxymethyl group is preferable.

The substituted ethyl group is preferably a 1-ethoxyethyl group or a 1-methyl-1-methoxyethyl group.

As the acyl group, an aliphatic acyl group having 1 to 6 carbon atoms, such as a formyl group, an acetyl group, a propionyl group, a butyryl group, an isobutyryl group, a valeryl group, and a pivaloyl group, is preferable.

As the alkoxycarbonyl group, an alkoxycarbonyl group having 1 to 4 carbon atoms is preferable.

The content of the repeating unit represented by General Formula (III), which has neither a hydroxyl group nor a cyano group, is preferably 0% to 40% by mole, and more preferably 0% to 20% by mole with respect to all repeating units in the resin (A).

Specific examples of the repeating unit represented by General Formula (III) are shown below, but the present invention is not limited thereto. In the formulae, Ra represents H, $CH_3$, $CH_2OH$, or $CF_3$.

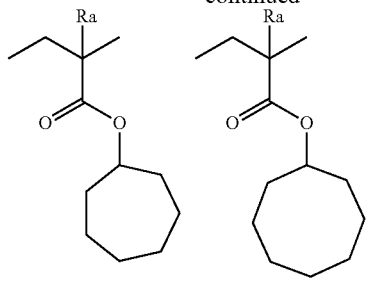

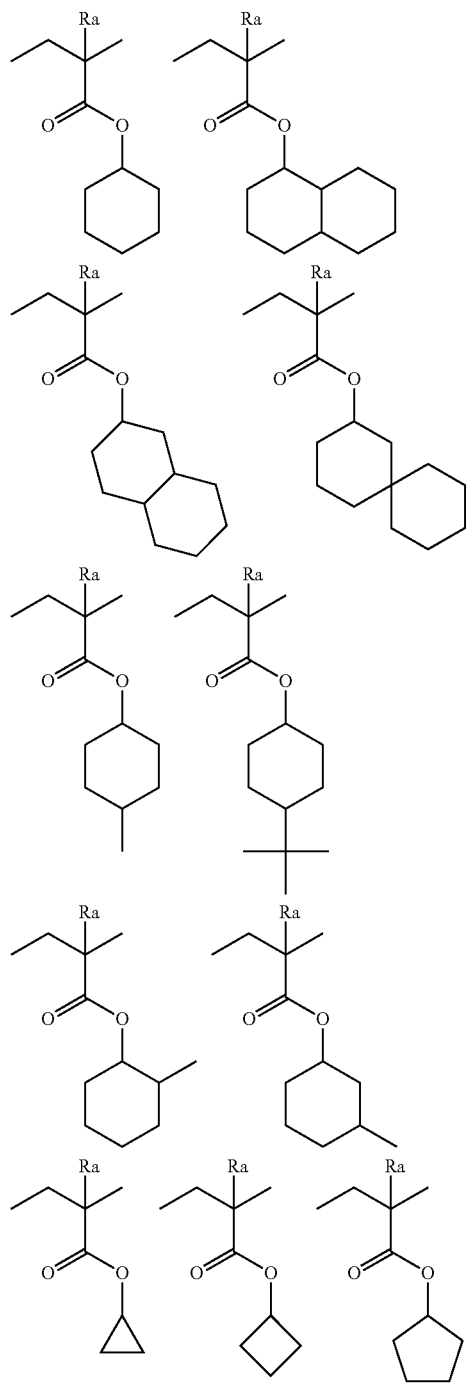

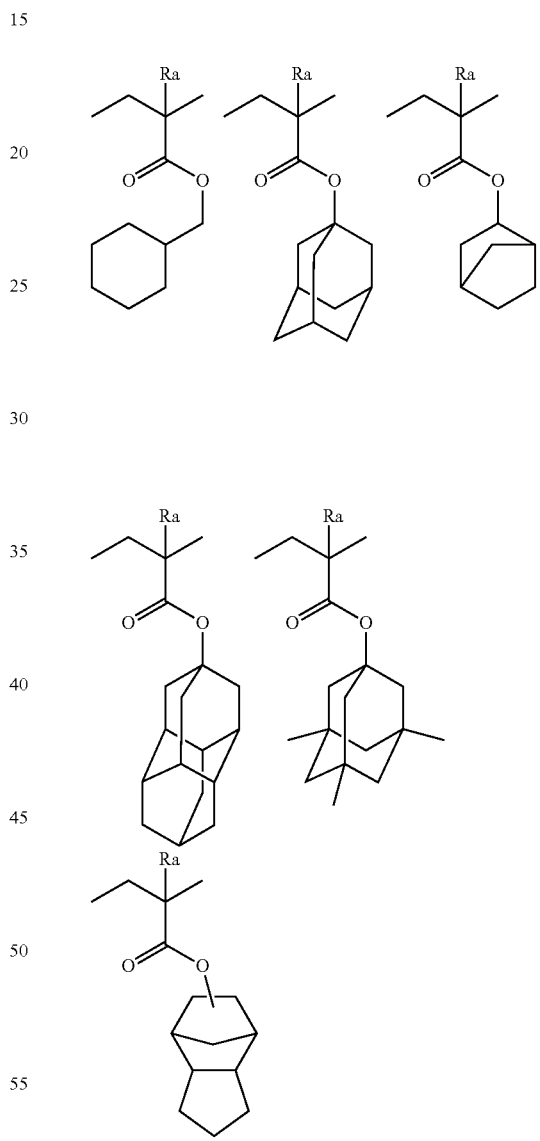

<<Other Repeating Units>>

The resin (A) may further have a repeating unit other than the above-mentioned repeating units.

For example, the resin (A) may have a repeating unit selected from the group consisting of a repeating unit having an oxathiane ring group, a repeating unit having an oxazolone ring group, a repeating unit having a dioxane ring group, and a repeating unit having a hydantoin ring group.

Such repeating units will be exemplified below.

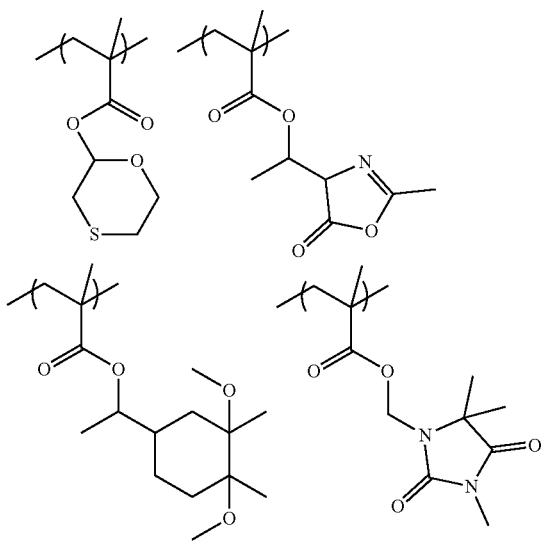

The resin (A) may have a variety of repeating structural units, in addition to the repeating structural units described above, for the purpose of adjusting dry etching resistance, suitability for a standard developer, adhesiveness to a substrate, a resist profile, resolving power, heat resistance, sensitivity, and the like.

As the resin (A), all repeating units also preferably include (meth)acrylate-based repeating units (particularly in a case where the specific resist composition is used as a resist composition for ArF). In this case, any of a resin in which all of the repeating units are methacrylate-based repeating units, a resin in which all of the repeating units are acrylate-based repeating units, and a resin in which all of the repeating units are methacrylate-based repeating units and acrylate-based repeating units can be used, and it is preferable that the amount of the acrylate-based repeating units is 50% by mole or less with respect to all repeating units.

The resin (A) can be synthesized in accordance with an ordinary method (for example, radical polymerization).

The weight-average molecular weight of the resin (A) as a value expressed in terms of polystyrene by a GPC method is preferably 3,000 to 20,000, and more preferably 5,000 to 15,000. By setting the weight-average molecular weight of the resin (A) to 3,000 to 200,000, deterioration of heat resistance and dry etching resistance can be further suppressed. In addition, deterioration of developability and deterioration of film forming property due to high viscosity can also be further suppressed.

The dispersity (molecular weight distribution) of the resin (A) is usually 1 to 5, preferably 1 to 3, more preferably 1.2 to 3.0, and still more preferably 1.2 to 2.0. The smaller the dispersity, the more excellent the resolution and the resist shape, and the smoother the side wall of the resist pattern, the more excellent the roughness.

The content of the resin (A) in the specific resist composition is preferably 50% to 99.9% by mass, and more preferably 60% to 99.0% by mass with respect to the total solid content of the composition.

Furthermore, the solid content is intended to be components excluding the solvent in the composition, and any of components other than the solvent are regarded as the solid content even in a case where they are liquid components.

In addition, the resin (A) may be used alone or in combination of a plurality thereof.

<Acid Diffusion Control Agent>

The specific resist composition may further include an acid diffusion control agent.

The acid diffusion control agent acts as a quencher that suppresses a reaction of an acid-decomposable resin in the unexposed area by excessive generated acids by trapping the acids generated from a photoacid generator and the like upon exposure. As the acid diffusion control agent, for example, a basic compound (DA), a basic compound (DB) having basicity that is reduced or lost upon irradiation with actinic rays or radiation, a low-molecular-weight compound (DD) having a nitrogen atom and a group that is eliminated by the action of an acid, and an onium salt compound (DE) having a nitrogen atom in the cationic moiety, can be used. In the specific resist composition, a known acid diffusion control agent can be appropriately used. For example, the known compounds disclosed in paragraphs [0627] to [0664] of the specification of US2016/0070167A1, paragraphs [0095] to [0187] of the specification of US2015/0004544A1, paragraphs [0403] to [0423] of the specification of US2016/0237190A1, and paragraphs [0259] to [0328] of the specification of US2016/0274458A1 can be suitably used as the acid diffusion control agent.

(Basic Compound (DA))

As the basic compound (DA), compounds having structures represented by Formulae (A) to (E) are preferable.

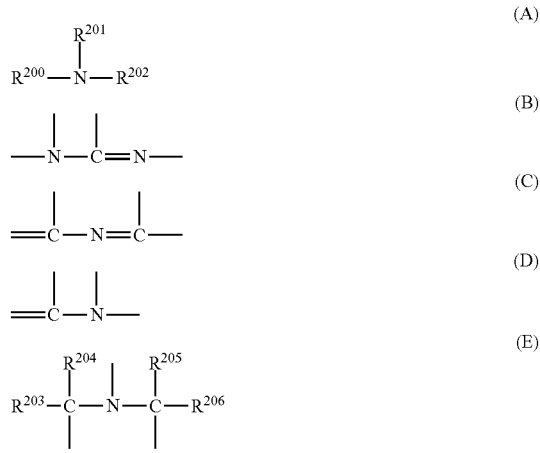

In General Formulae (A) and (E), $R^{200}$, $R^{201}$, and $R^{202}$ may be the same as or different from each other, and each independently represent a hydrogen atom, an alkyl group (preferably having 1 to 20 carbon atoms), a cycloalkyl group (preferably having 3 to 20 carbon atoms), or an aryl group (having 6 to 20 carbon atoms). $R^{201}$ and $R^{202}$ may be bonded to each other to form a ring.

$R^{203}$, $R^{204}$, $R^{205}$, and $R^{206}$ may be the same as or different from each other and each independently represent an alkyl group having 1 to 20 carbon atoms.

The alkyl group in each of General Formulae (A) and (E) may have a substituent or may be unsubstituted.

With regard to the alkyl group, the alkyl group having a substituent is preferably an aminoalkyl group having 1 to 20 carbon atoms, a hydroxyalkyl group having 1 to 20 carbon atoms, or a cyanoalkyl group having 1 to 20 carbon atoms.

The alkyl group in each of General Formulae (A) and (E) are more preferably unsubstituted.

As the basic compound (DA), guanidine, aminopyrrolidine, pyrazole, pyrazoline, piperazine, aminomorpholine, aminoalkylmorpholine, or piperidine is preferable; and a compound having an imidazole structure, a diazabicyclo structure, an onium hydroxide structure, an onium carboxylate structure, a trialkylamine structure, an aniline structure, or a pyridine structure, an alkylamine derivative having a hydroxyl group and/or an ether bond, or an aniline derivative having a hydroxyl group and/or an ether bond is more preferable.

(Basic Compound (DB) Having Basicity that is Reduced or Lost Upon Irradiation with Actinic Rays or Radiation)

The basic compound (DB) having basicity reduced or lost upon irradiation with actinic rays or radiation (hereinafter also referred to as a "compound (DB)") is a compound which has a proton-accepting functional group, and decomposes under irradiation with actinic rays or radiation to exhibit deterioration in proton-accepting properties, no proton-accepting properties, or a change from the proton-accepting properties to acidic properties.

The proton-accepting functional group refers to a functional group having a group or electron capable of electrostatically interacting with a proton, and for example, means a functional group with a macrocyclic structure, such as a cyclic polyether, or a functional group having a nitrogen atom having an unshared electron pair not contributing to π-conjugation. The nitrogen atom having an unshared electron pair not contributing to π-conjugation is, for example, a nitrogen atom having a partial structure represented by the following formula.

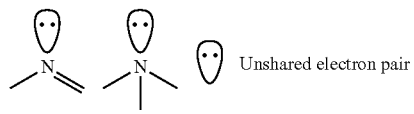

Unshared electron pair

Preferred examples of the partial structure of the proton-accepting functional group include a crown ether structure, an azacrown ether structure, primary to tertiary amine structures, a pyridine structure, an imidazole structure, and a pyrazine structure.

The compound (DB) decomposes upon irradiation with actinic rays or radiation to generate a compound exhibiting deterioration in proton-accepting properties, no proton-accepting properties, or a change from the proton-accepting properties to acidic properties. Here, exhibiting deterioration in proton-accepting properties, no proton-accepting properties, or a change from the proton-accepting properties to acidic properties means a change of proton-accepting properties due to the proton being added to the proton-accepting functional group, and specifically a decrease of the equilibrium constant in chemical equilibrium in a case where a proton adduct is generated from the compound (DB) having the proton-accepting functional group and the proton.

The proton-accepting properties can be confirmed by performing pH measurement.

The acid dissociation constant (pKa) of the compound generated by decomposition of the compound (DB) upon irradiation with actinic rays or radiation preferably satisfies pKa<−1, and more preferably satisfies −13<pKa<−1, and still more preferably satisfies −13<pKa<−3.

Furthermore, the acid dissociation constant (pKa) can be determined by the above-mentioned method.

(Low-Molecular-Weight Compound (DD) Having Nitrogen Atom and Group that is Eliminated by Action of Acid)

The low-molecular-weight compound (DD) having a nitrogen atom and having a group that is eliminated by the action of an acid (hereinafter also referred to as a "compound (DD)") is preferably an amine derivative having a group that is eliminated by the action of an acid on the nitrogen atom.

As the group that is eliminated by the action of an acid, an acetal group, a carbonate group, a carbamate group, a tertiary ester group, a tertiary hydroxyl group, or a hemiaminal ether group is preferable, and the carbamate group or the hemiaminal ether group is more preferable.

The molecular weight of the compound (DD) is preferably 100 to 1,000, more preferably 100 to 700, and still more preferably 100 to 500.

The compound (DD) may have a carbamate group having a protective group on the nitrogen atom. The protective group constituting the carbamate group is represented by General Formula (d-1).

In General Formula (d-1), $R_b$'s each independently represent a hydrogen atom, an alkyl group (preferably having 1 to 10 carbon atoms), a cycloalkyl group (preferably having 3 to 30 carbon atoms), an aryl group (preferably having 3 to 30 carbon atoms), an aralkyl group (preferably having 1 to 10 carbon atoms), or an alkoxyalkyl group (preferably having 1 to 10 carbon atoms). $R_b$'s may be linked to each other to form a ring.

The alkyl group, the cycloalkyl group, the aryl group, or the aralkyl group represented by $R_b$ may be each independently substituted with a functional group such as a hydroxyl group, a cyano group, an amino group, a pyrrolidino group, a piperidino group, a morpholino group, and an oxo group, an alkoxy group, or a halogen atom. The same applies to the alkoxyalkyl group represented by $R_b$.

As $R_b$, a linear or branched alkyl group, a cycloalkyl group, or an aryl group is preferable, and the linear or branched alkyl group, or the cycloalkyl group is more preferable.

Examples of the ring formed by the mutual linking of two $R_b$'s include an alicyclic hydrocarbon, an aromatic hydrocarbon, a heterocyclic hydrocarbon, and derivatives thereof.

Examples of the specific structure of the group represented by General Formula (d-1) include, but are not limited to, the structures disclosed in paragraph [0466] of the specification of US2012/0135348A1.

The compound (DD) is preferably a compound represented by General Formula (6).

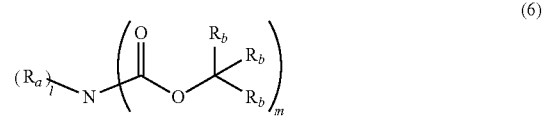

In General Formula (6), l represents an integer of 0 to 2, m represents an integer of 1 to 3, and these satisfy l+m=3.

$R_a$ represents a hydrogen atom, an alkyl group, a cycloalkyl group, an aryl group, or an aralkyl group. In a case where l is 2, two $R_a$'s may be the same as or different from each other, and the two $R_a$'s may be linked to each other to form a heterocyclic ring with the nitrogen atom in the formula. This heterocyclic ring may include a heteroatom other than the nitrogen atom in the formula.

$R_b$ has the same definition as $R_b$ in General Formula (d-1), and preferred examples are also the same.

In General Formula (6), the alkyl group, the cycloalkyl group, the aryl group, and the aralkyl group as $R_a$ may be each independently substituted with the same groups as the group mentioned above as a group which may be substituted in the alkyl group, the cycloalkyl group, the aryl group, and the aralkyl group as $R_b$.

Specific examples of the alkyl group, the cycloalkyl group, the aryl group, and the aralkyl group (these groups may be substituted with the groups as described above) of $R_a$ include the same groups as the specific examples as described above with respect to $R_b$.

Specific examples of the particularly preferred compound (DD) in the present invention include, but are not limited to, the compounds disclosed in paragraph [0475] of the specification of US2012/0135348A1.

(Onium Salt Compound (DE) Having Nitrogen Atom in Cationic Moiety)

The onium salt compound (DE) having a nitrogen atom in the cationic moiety (hereinafter also referred to as a "compound (DE)") is preferably a compound having a basic moiety including a nitrogen atom in the cationic moiety. The basic moiety is preferably an amino group, and more preferably an aliphatic amino group. All of the atoms adjacent to the nitrogen atom in the basic moiety are still more preferably hydrogen atoms or carbon atoms. In addition, from the viewpoint of improving basicity, it is preferable that an electron-withdrawing functional group (such as a carbonyl group, a sulfonyl group, a cyano group, and a halogen atom) is not directly linked to the nitrogen atom.

Preferred specific examples of the compound (DE) include, but are not limited to, the compounds disclosed in paragraph [0203] of US2015/0309408A1.

Preferred examples of the acid diffusion control agent are shown below.

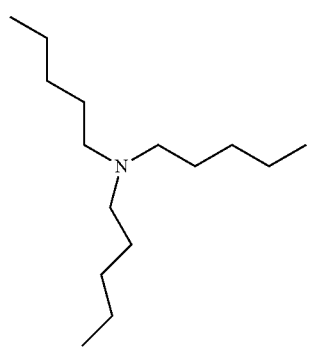

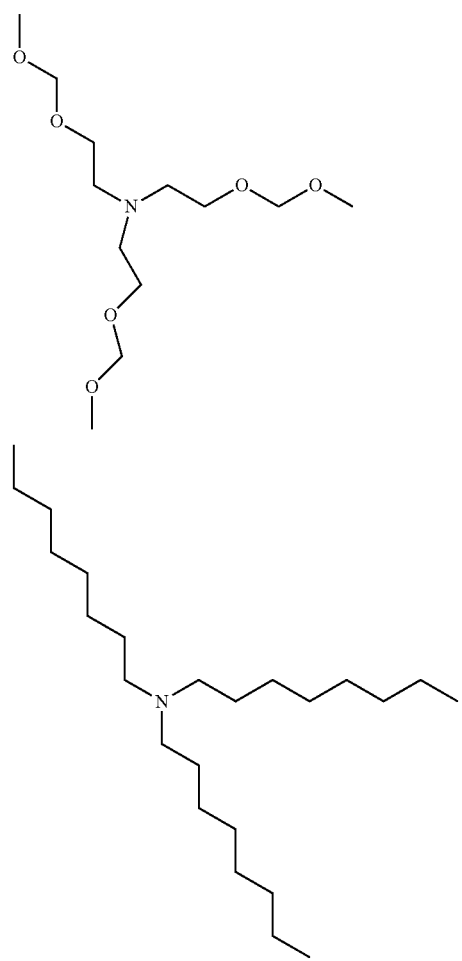

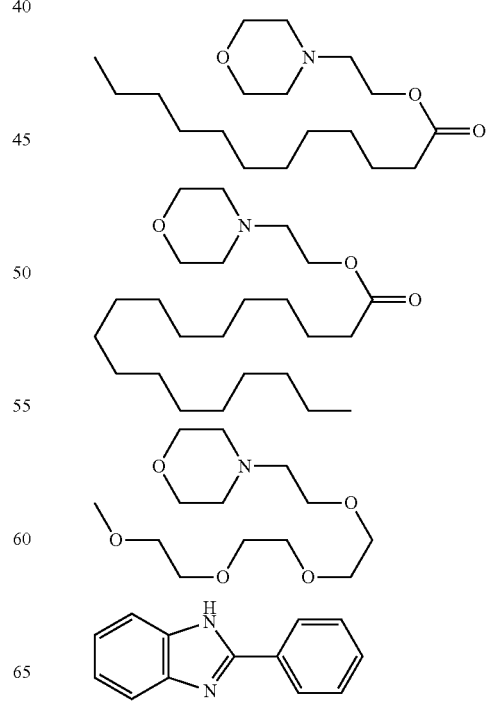

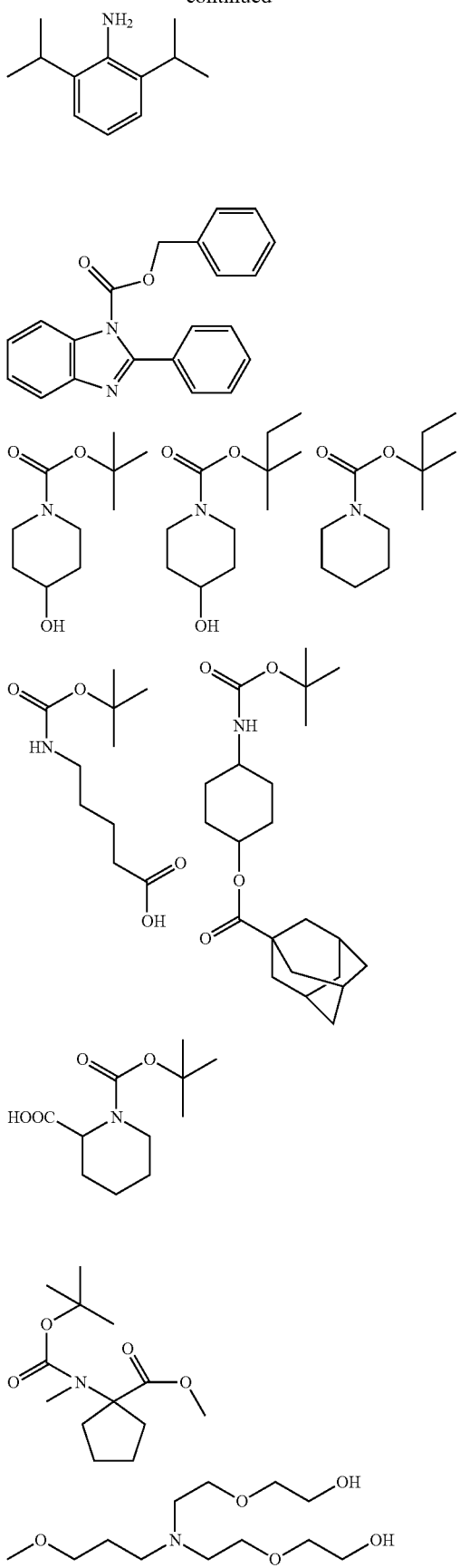

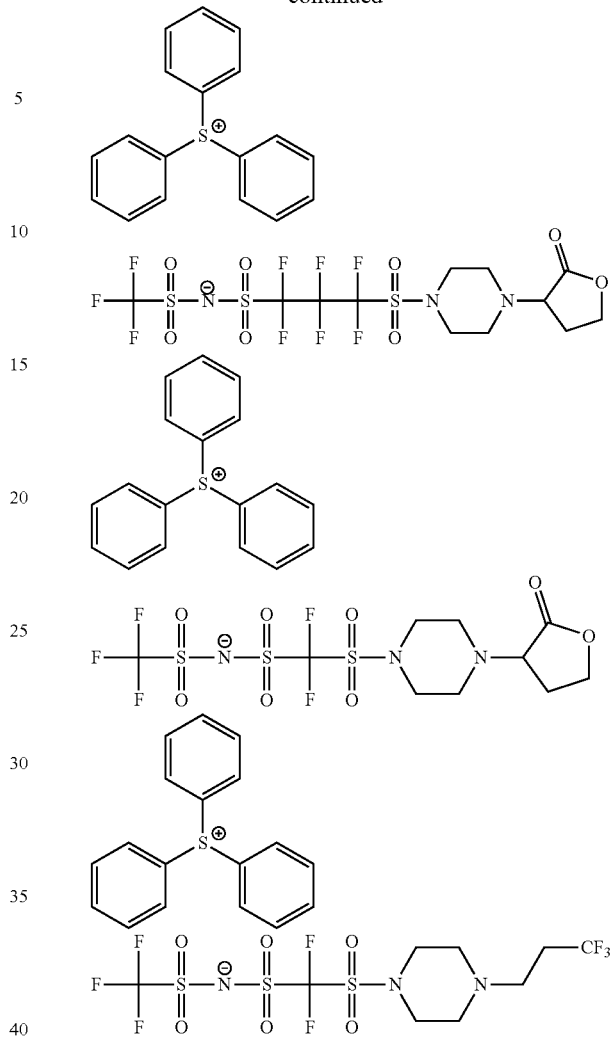

In a case where the specific resist composition includes an acid diffusion control agent, the content of the acid diffusion control agent (a total content of the acid diffusion control agents in a case where a plurality of kinds of the acid diffusion control agents are present) is preferably 0.1% to 11.0% by mass, more preferably 0.1% to 10.0% by mass, still more preferably 0.1% to 8.0% by mass, and particularly preferably 0.1% to 5.0% by mass with respect to the total solid content of the composition.

In the specific resist composition, the acid diffusion control agents may be used alone or in combination of two or more kinds thereof.

<Hydrophobic Resin>

The specific resist composition may include a hydrophobic resin different from the resin (A), in addition to the resin (A).

Although it is preferable that the hydrophobic resin is designed to be unevenly distributed on a surface of the resist film, it does not necessarily need to have a hydrophilic group in the molecule as different from the surfactant, and does not need to contribute to uniform mixing of polar materials and non-polar materials.

Examples of the effect of addition of the hydrophobic resin include a control of static and dynamic contact angles of a surface of the resist film with respect to water and suppression of out gas.

The hydrophobic resin preferably has any one or more of a "fluorine atom", a "silicon atom", and a "$CH_3$ partial structure which is contained in a side chain moiety of a resin" from the viewpoint of uneven distribution on the film surface layer, and more preferably has two or more kinds thereof. Incidentally, the hydrophobic resin preferably has a hydrocarbon group having 5 or more carbon atoms. These groups may be contained in the main chain of the resin or may be substituted in a side chain.

In a case where hydrophobic resin includes a fluorine atom and/or a silicon atom, the fluorine atom and/or the silicon atom in the hydrophobic resin may be included in the main chain or a side chain of the resin.

In a case where the hydrophobic resin includes a fluorine atom, as a partial structure having a fluorine atom, an alkyl group having a fluorine atom, a cycloalkyl group having a fluorine atom, or an aryl group having a fluorine atom is preferable.

The alkyl group having a fluorine atom (preferably having 1 to 10 carbon atoms, and more preferably having 1 to 4 carbon atoms) is a linear or branched alkyl group in which at least one hydrogen atom is substituted with a fluorine atom, and the alkyl group may further have a substituent other than a fluorine atom.

The cycloalkyl group having a fluorine atom is a monocyclic or polycyclic cycloalkyl group in which at least one hydrogen atom is substituted with a fluorine atom, and may further have a substituent other than a fluorine atom.

Examples of the aryl group having a fluorine atom include an aryl group such as a phenyl group and a naphthyl group, in which at least one hydrogen atom is substituted with a fluorine atom, and the aryl group may further have a substituent other than the fluorine atom.

Examples of the repeating unit having a fluorine atom or a silicon atom include those exemplified in paragraph [0519] of US2012/0251948A1.

Furthermore, as described above, it is also preferable that the hydrophobic resin includes a $CH_3$ partial structure in a side chain moiety.

Here, the $CH_3$ partial structure contained in the side chain moiety in the hydrophobic resin includes a $CH_3$ partial structure contained in an ethyl group, a propyl group, and the like. On the other hand, a methyl group bonded directly to the main chain of the hydrophobic resin (for example, an α-methyl group in the repeating unit having a methacrylic acid structure) makes only a small contribution of uneven distribution on the surface of the hydrophobic resin due to the effect of the main chain, and it is therefore not included in the $CH_3$ partial structure in the present invention.

With regard to the hydrophobic resin, reference can be made to the description in paragraphs [0348] to [0415] of JP2014-010245A, the contents of which are incorporated herein by reference.

Furthermore, the resins described in JP2011-248019A, JP2010-175859A, and JP2012-032544A, in addition to those above, can also be preferably used as the hydrophobic resin.

Preferred examples of a monomer corresponding to the repeating unit constituting the hydrophobic resin are shown below.

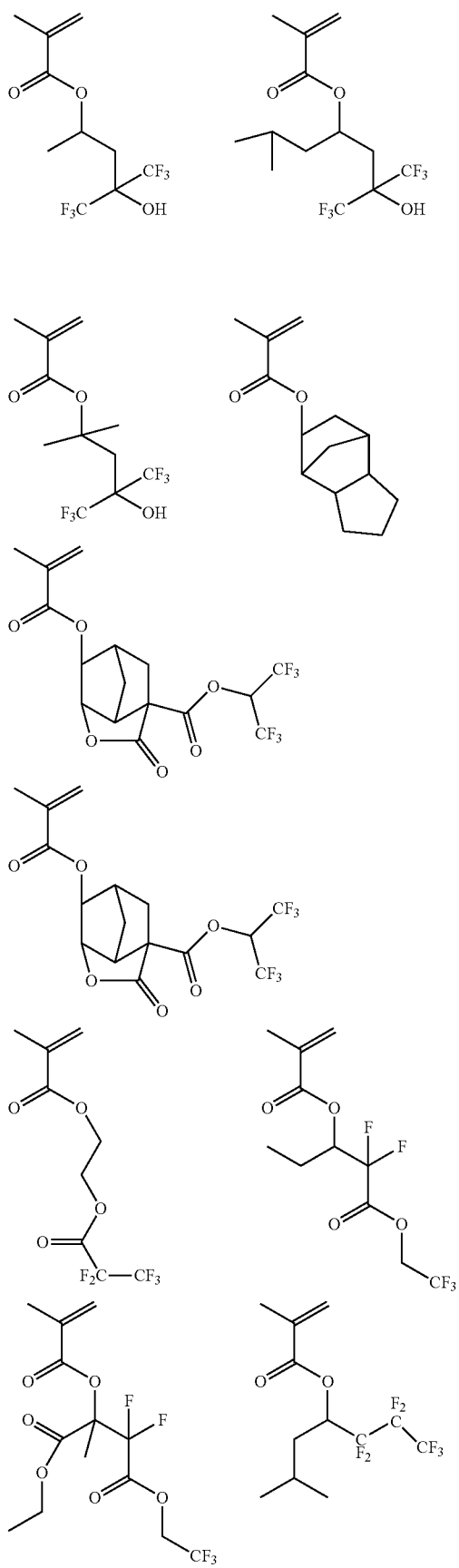

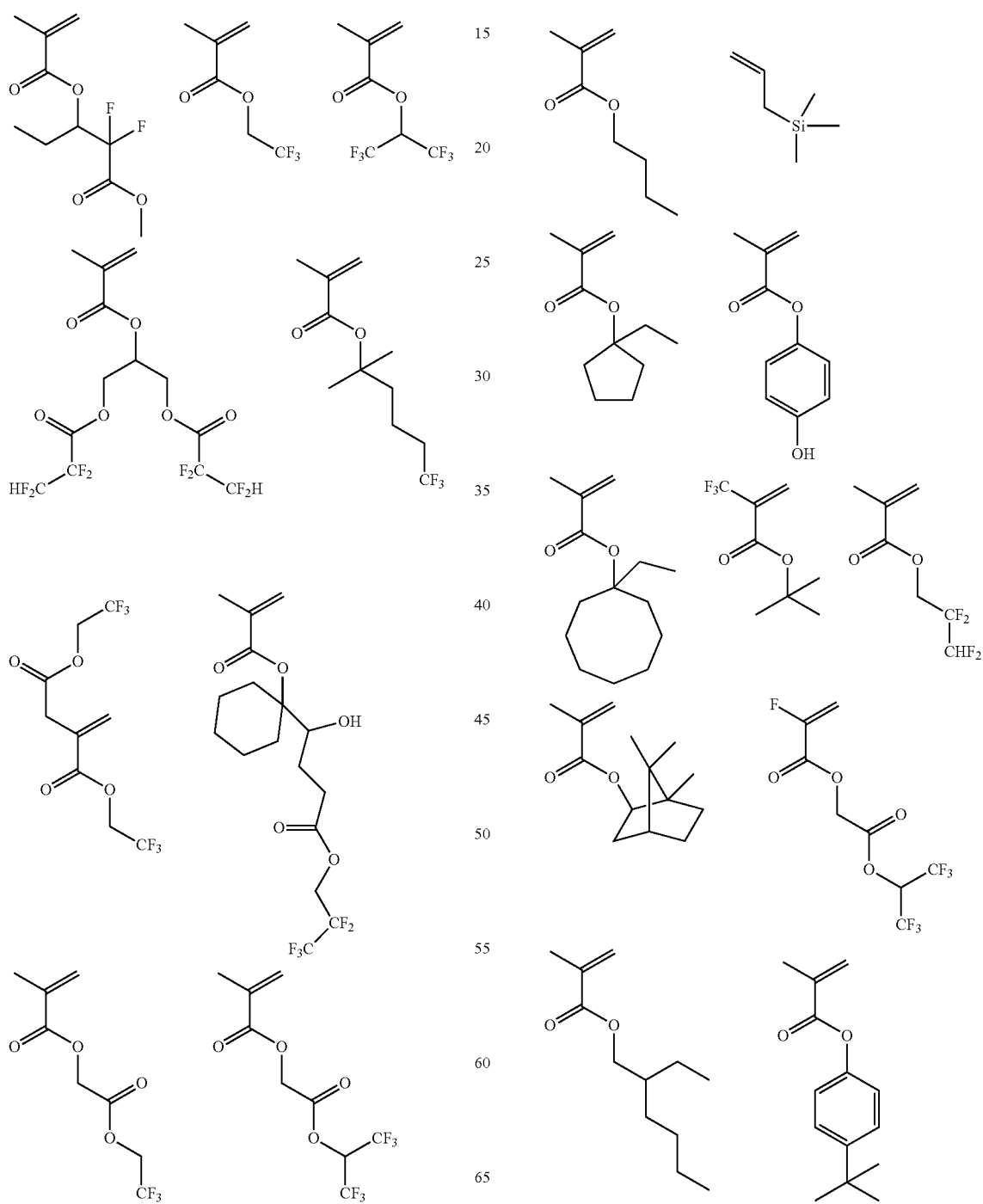

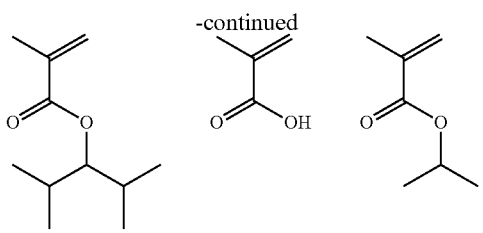

In a case where the specific resist composition includes a hydrophobic resin, a content of the hydrophobic resin is preferably 0.01% to 20.0% by mass, more preferably 0.1% to 15.0% by mass, still more preferably 0.1% to 10.0% by mass, and particularly preferably 0.1% to 6.0% by mass with respect to the total solid content of the composition.

<Surfactant>

The specific resist composition may include a surfactant. By incorporation of the surfactant, it is possible to form a pattern having more excellent adhesiveness and fewer development defects.

As the surfactant, fluorine-based and/or silicon-based surfactants are preferable.

Examples of the fluorine-based and/or silicon-based surfactants include the surfactants described in paragraph [0276] of the specification of US2008/0248425A. In addition, EFTOP EF301 or EF303 (manufactured by Shin-Akita Chemical Co., Ltd.); FLUORAD FC430, 431, or 4430 (manufactured by Sumitomo 3M Inc.); MEGAFACE F171, F173, F176, F189, F113, F110, F177, F120, or R08 (manufactured by DIC Corporation); SURFLON S-382, SC101, 102, 103, 104, 105, or 106 (manufactured by Asahi Glass Co., Ltd.); TROYSOL S-366 (manufactured by Troy Corporation); GF-300 or GF-150 (manufactured by Toagosei Co., Ltd.); SURFLON S-393 (manufactured by AGC Seimi Chemical Co., Ltd.); EFTOP EF121, EF122A, EF122B, RF122C, EF125M, EF135M, EF351, EF352, EF801, EF802, or EF601 (manufactured by JEMCO Inc.); PF636, PF656, PF6320, or PF6520 (manufactured by OMNOVA Solutions Inc.); KH-20 (manufactured by Asahi Kasei Corporation); or FTX-204G, 208G, 218G, 230G, 204D, 208D, 212D, 218D, or 222D (manufactured by NEOS COMPANY LIMITED) may be used. In addition, a polysiloxane polymer, KP-341 (manufactured by Shin-Etsu Chemical Co., Ltd.), can also be used as the silicon-based surfactant.

Moreover, in addition to the known surfactants as shown above, a surfactant may be synthesized using a fluoroaliphatic compound manufactured using a telomerization method (also referred to as a telomer method) or an oligomerization method (also referred to as an oligomer method). Specifically, a polymer including a fluoroaliphatic group derived from fluoroaliphatic compound may be used as the surfactant. This fluoroaliphatic compound can be synthesized, for example, by the method described in JP2002-90991A.

As the polymer having a fluoroaliphatic group, a copolymer of a monomer having a fluoroaliphatic group and (poly(oxyalkylene))acrylate and/or (poly(oxyalkylene)) methacrylate is preferable, and the polymer may be unevenly distributed or block-copolymerized. Furthermore, examples of the poly(oxyalkylene) group include a poly (oxyethylene) group, a poly(oxypropylene) group, and a poly(oxybutylene) group, and the group may also be a unit such as those having alkylenes having different chain lengths within the same chain length such as poly(block-linked oxyethylene, oxypropylene, and oxyethylene) and poly(block-linked oxyethylene and oxypropylene). In addition, the copolymer of a monomer having a fluoroaliphatic group and (poly(oxyalkylene))acrylate (or methacrylate) is not limited only to a binary copolymer but may also be a ternary or higher copolymer obtained by simultaneously copolymerizing monomers having two or more different fluoroaliphatic groups or two or more different (poly(oxyalkylene)) acrylates (or methacrylates).

Examples of a commercially available surfactant thereof include MEGAFACE F-178, F-470, F-473, F-475, F-476, and F-472 (manufactured by DIC Corporation), a copolymer of acrylate (or methacrylate) having a $C_6F_{13}$ group and (poly(oxyalkylene))acrylate (or methacrylate), and a copolymer of acrylate (or methacrylate) having a $C_3F_7$ group, (poly(oxyethylene))acrylate (or methacrylate), and (poly (oxypropylene))acrylate (or methacrylate).

In addition, a surfactant other than the fluorine-based surfactant and/or the silicon-based surfactants described in paragraph [0280] of the specification of US2008/0248425A may be used.

These surfactants may be used alone or in combination of two or more kinds thereof.

A content of the surfactant is preferably 0.0001% to 2.0% by mass and more preferably 0.0005% to 1.0% by mass with respect to the total solid content of the composition.

<Solvent>

The specific resist composition includes a solvent.

Furthermore, the solvent may be a solvent that is further added separately in addition to the first solvent included in the first solution which will be described later and the second solvent included in the second solution which will be described later.

As the solvent, a solvent including at least one solvent of (M1) propylene glycol monoalkyl ether carboxylate, or (M2) at least one selected from the group consisting of a propylene glycol monoalkyl ether, a lactic acid ester, an acetic acid ester, butyl butyrate, an alkoxypropionic acid ester, a chain ketone, a cyclic ketone, a lactone, and an alkylene carbonate is preferable. Furthermore, this solvent may further include components other than the components (M1) and (M2).

The present inventors have found that by using such a solvent and the above-mentioned resin (A) in combination, a pattern having a small number of development defects can be formed while improving the coating property of the composition. A reason therefor is not necessarily clear, but the present inventors have considered that since these solvents have a good balance among the solubility, the boiling point, and the viscosity of the resin (A), the unevenness of the film thickness of a composition film, the generation of precipitates during spin coating, and the like can be suppressed.

As the component (M1), one or more selected from the group consisting of propylene glycol monomethyl ether acetate (PGMEA), propylene glycol monomethyl ether propionate, and propylene glycol monoethyl ether acetate are preferable, and the propylene glycol monomethyl ether acetate (PGMEA) is more preferable.

As the component (M2), the following ones are preferable.

As the propylene glycol monoalkyl ether, propylene glycol monomethyl ether (PGME) or propylene glycol monoethyl ether (PGEE) is preferable.

As the lactic acid ester, ethyl lactate, butyl lactate, or propyl lactate is preferable.

As the acetic acid ester, methyl acetate, ethyl acetate, butyl acetate, isobutyl acetate, propyl acetate, isoamyl acetate, methyl formate, ethyl formate, butyl formate, propyl formate, or 3-methoxybutyl acetate is preferable.

As the alkoxypropionic acid ester, methyl 3-methoxypropionate (MMP) or ethyl 3-ethoxypropionate (EEP) is preferable.

As the chain ketone, 1-octanone, 2-octanone, 1-nonanone, 2-nonanone, acetone, 2-heptanone, 4-heptanone, 1-hexanone, 2-hexanone, diisobutyl ketone, phenyl acetone, methyl ethyl ketone, methyl isobutyl ketone, acetyl acetone, acetonyl acetone, ionone, diacetonyl alcohol, acetyl carbinol, acetophenone, methyl naphthyl ketone, or methyl amyl ketone is preferable.

As the cyclic ketone, methyl cyclohexanone, isophorone, or cyclohexanone is preferable.

As the lactone, γ-butyrolactone is preferable.

As the alkylene carbonate, propylene carbonate is preferable.

As the component (M2), propylene glycol monomethyl ether (PGME), ethyl lactate, ethyl 3-ethoxypropionate, methyl amyl ketone, cyclohexanone, butyl acetate, pentyl acetate, γ-butyrolactone, or propylene carbonate is more preferable, and propylene glycol monomethyl ether (PGME), ethyl lactate, cyclohexanone, or γ-butyrolactone is still more preferable.

In addition to the components, it is preferable to use an ester-based solvent having 7 or more carbon atoms (preferably 7 to 14 carbon atoms, more preferably 7 to 12 carbon atoms, and still more preferably 7 to 10 carbon atoms) and 2 or less heteroatoms.

As the ester-based solvent having 7 or more carbon atoms and 2 or less heteroatoms, amyl acetate, 2-methylbutyl acetate, 1-methylbutyl acetate, hexyl acetate, pentyl propionate, hexyl propionate, butyl propionate, isobutyl isobutyrate, heptyl propionate, or butyl butanoate is preferable, and isoamyl acetate is more preferable.

As the component (M2), a component having a flash point (hereinafter also referred to as fp) of 37° C. or higher is preferably used. As such a component (M2), propylene glycol monomethyl ether (fp: 47° C.), ethyl lactate (fp: 53° C.), ethyl 3-ethoxypropionate (fp: 49° C.), methyl amyl ketone (fp: 42° C.), cyclohexanone (fp: 44° C.), pentyl acetate (fp: 45° C.), methyl 2-hydroxyisobutyrate (fp: 45° C.), γ-butyrolactone (fp: 101° C.), or propylene carbonate (fp: 132° C.) is preferable. Among those, propylene glycol monoethyl ether, ethyl lactate, pentyl acetate, or cyclohexanone is more preferable, and propylene glycol monoethyl ether or ethyl lactate is still more preferable.

In addition, "flash point" herein means the value described in a reagent catalog of Tokyo Chemical Industry Co., Ltd. or Sigma-Aldrich Co. LLC.

The mixing mass ratio (M1/M2) of the content of the component (M1) to the component (M2) in the mixed solvent is preferably in the range of "100/0" to "15/85", and more preferably in the range of "100/0" to "40/60". In a case where such a configuration is adopted and used, it is possible to further reduce the number of development defects.

As described above, the solvent may further include components other than the components (M1) and (M2). In this case, the content of the components other than the components (M1) and (M2) is preferably in the range of 30% by mass or less, and more preferably 5% to 30% by mass with respect to the total mass of the solvent.

The content of the solvent in the specific resist composition is preferably set so that the concentration of solid contents is 0.5% to 30.0% by mass, and more preferably set so that the concentration of solid contents is 1.0% to 20.0% by mass. With this content, the coating property of the specific resist composition is more excellent.

<Other Additives>

The specific resist composition may further include a resin other than those described above, a crosslinking agent, an acid proliferation agent, a dye, a plasticizer, a photosensitizer, a light absorber, an alkali-soluble resin, a dissolution inhibitor, a dissolution accelerator, or the like.

[Method for Producing Resist Composition]

Next, the production method of the embodiment of the present invention will be described.

Specifically, the production method of the embodiment of the present invention includes a step A and a step B.

Step A: A step of preparing a first solution including an acid-decomposable resin and a first solvent Step B: A step of mixing the first solution with a specific photoacid generator Hereinbelow, the step A and the step B will be described.

<Step A>

The step A is a step of preparing a first solution including an acid-decomposable resin and a first solvent. Hereinbelow, the first solution will first be described, and the procedure (method for preparing the first solution) of the step A will then be described.

(First Solution)

The first solution includes an acid-decomposable resin and a first solvent.

The acid-decomposable resin is as described above.

The first solvent is not particularly limited, and examples thereof include solvents (specifically the above-mentioned components (M1) and (M2), and the like) that can be included in the above-mentioned resist composition, but is preferably propylene glycol monoalkyl ether carboxylate from the viewpoint that the performance of suppressing defects of a pattern formed is more excellent.

Specific examples of the propylene glycol monoalkyl ether carboxylate include propylene glycol monomethyl ether acetate (PGMEA), propylene glycol monomethyl ether propionate, and propylene glycol monoethyl ether acetate.

As the first solvent, among those, the solvent having an SP value of less than 18.5 MPa$^{1/2}$ is preferable from the viewpoints that the aggregation of the specific photoacid generators is further suppressed and the performance of suppressing defects of a pattern formed is more excellent.

Furthermore, the SP value of the present invention was calculated using the Fedor's method described in "Properties of Polymers, $2^{nd}$ Edition, 1976 Publishing". In addition, the unit of the SP value is MPa$^{1/2}$ unless otherwise specified.

Examples of the propylene glycol monoalkyl ether carboxylate having an SP value of less than 18.5 MPa$^{1/2}$ among the above-mentioned propylene glycol monoalkyl ether carboxylates include propylene glycol monomethyl ether acetate and propylene glycol monoethyl ether acetate, among which propylene glycol monomethyl ether acetate is preferable.

Furthermore, the first solvent may be used alone or in combination of two or more kinds thereof.

In a case where a plurality of kinds of the first solvents are used in combination as the first solvent, it is preferable that the SP value of at least one of the solvents is less than 18.5 MPa$^{1/2}$, and it is more preferable that the SP values of all the solvents are less than 18.5 MPa$^{1/2}$.

The first solution may include other components other than the acid-decomposable resin and the first solvent, but it is preferable that the first solution substantially does not include the specific photoacid generator. Here, the expression "the first solution substantially does not include the specific photoacid generator" is intended to mean that a content of the specific photoacid generator is 3.0% by mass or less with respect to a total mass of the first solution, and the content is preferably 2.0% by mass or less, more preferably 1.0% by mass or less, still more preferably 0.5% by mass or less, and particularly preferably 0.3% by mass or less. Furthermore, a lower limit value thereof is 0% by mass.

It is preferable that the first solution substantially does not include other components other than the acid-decomposable resin and the solvent. Here, the expression "the first solution substantially does not include other components other than the acid-decomposable resin and the solvent" is intended to mean that a total content of other components other than the acid-decomposable resin and the solvent is 3.0% by mass or less, and the total content is preferably 2.0% by mass or less, more preferably 1.0% by mass or less, still more preferably 0.5% by mass or less, and particularly preferably 0.3% by mass or less with respect to the total mass of the first solution. Furthermore, a lower limit value thereof is 0% by mass.

A concentration of solid contents of the first solution is not particularly limited, and is, for example, 1.0% to 30.0% by mass, and preferably 5.0% to 20.0% by mass from the viewpoint that the performance of suppressing defects of a pattern formed is more excellent. Furthermore, the concentration of solid contents is a mass percentage of the mass of the component excluding the solvent with respect to the total mass of the first solution.

(Method for Preparing First Solution)

A method for preparing the first solution is not particularly limited, and it is preferable to mix the acid-decomposable resin and the first solvent so that the above-mentioned concentration of solid contents is obtained, following by stirring the mixture.

A stirring time is not particularly limited, but is preferably 1 hour or more, and more preferably 5 hours or more. A longer stirring time is more preferable, and the stirring time is, for example, 12 hours.

A stirring temperature is not particularly limited, but is preferably 15° C. to 25° C.

<Step B>

The step B is a step of mixing the first solution with a specific photoacid generator.

The step B may be a step of directly mixing the specific photoacid generator with the first solution (hereinafter also referred to as a "step B1"), but it is preferable to include a step B2 and a step B3 from the viewpoint that the performance of suppressing defects of a pattern formed is more excellent. That is, it is preferable that the step is a step of preparing a solution obtained by dissolving the specific photoacid generator in a solvent in advance and mixing this solution with the first solution.

Step B2: A step of preparing a second solution including a specific photoacid generator and a second solvent Step B3: A step of mixing the first solution with the second solution Hereinbelow, the procedure of the step B1 will first be described, and then the second solution, the procedure of the step B2 (the method for preparing the second solution), and the procedure of the step B3 will be described.

(Procedure of Step B1)

The step B1 is a step of directly mixing the specific photoacid generator with the first solution.

The step B1 is not particularly limited, but it is preferable to directly mix the first solution and the specific photoacid generator, and then stir the obtained mixed liquid.

A stirring time is not particularly limited, but is preferably 1 hour or more, and more preferably 5 hours or more. A longer stirring time is more preferable, and the stirring time is, for example, 12 hours.

A stirring temperature is not particularly limited, but from the viewpoint that the aggregation of the specific photoacid generators can be further suppressed, a higher temperature is desirable, and the stirring temperature is preferably 10° C. or higher. An upper limit value of the stirring temperature is preferably 40° C. or lower from the viewpoint that stacking due to a change in the alignment of the specific photoacid generator can be suppressed.

(Second Solution)

The second solution includes a specific photoacid generator and a second solvent.

The specific photoacid generator is as described above.

The second solvent is not particularly limited, and examples thereof include solvents (specifically the above-mentioned components (M1) and (M2), and the like) that can be included in the above-mentioned resist composition, but from the viewpoint that the performance of suppressing defects of a pattern formed is more excellent, the second solvent is preferably selected from the group consisting of a propylene glycol monoalkyl ether, a lactic acid ester, an acetic acid ester, butyl butyrate, an alkoxypropionic acid ester, a chain ketone, a cyclic ketone, a lactone, and an alkylene carbonate.

As the propylene glycol monoalkyl ether, propylene glycol monomethyl ether (PGME) or propylene glycol monoethyl ether (PGEE) is preferable.

As the lactic acid ester, ethyl lactate, butyl lactate, or propyl lactate is preferable.

As the acetic acid ester, methyl acetate, ethyl acetate, butyl acetate, isobutyl acetate, propyl acetate, isoamyl acetate, methyl formate, ethyl formate, butyl formate, propyl formate, or 3-methoxybutyl acetate is preferable.

As the alkoxy propionic ester, methyl 3-methoxypropionate (MMP), or ethyl 3-ethoxypropionate (EEP) is preferable.

As the chain ketone, 1-octanone, 2-octanone, 1-nonanone, 2-nonanone, acetone, 2-heptanone, 4-heptanone, 1-hexanone, 2-hexanone, diisobutyl ketone, phenyl acetone, methyl ethyl ketone, methyl isobutyl ketone, acetyl acetone, acetonyl acetone, ionone, diacetonyl alcohol, acetyl carbinol, acetophenone, methyl naphthyl ketone, or methyl amyl ketone is preferable.

As the cyclic ketone, methyl cyclohexanone, isophorone, or cyclohexanone is preferable.

As the lactone, γ-butyrolactone is preferable.

As the alkylene carbonate, propylene carbonate is preferable.

As the second solvent, among those, the solvent having an SP value of 18.5 $MPa^{1/2}$ or more is preferable from the viewpoints that the aggregation of the specific photoacid generators is further suppressed and the performance of suppressing defects of a pattern formed is more excellent.

Among the above-mentioned solvents, the solvent having an SP value of 18.5 $MPa^{1/2}$ or more is preferably propylene glycol monomethyl ether, ethyl lactate, cyclohexanone, γ-butyrolactone, or propylene carbonate.

Furthermore, the second solvent may be used alone or in combination of two or more kinds thereof.

In a case where a plurality of kinds of the second solvents are used in combination as the second solvent, it is preferable that the SP value of at least one of the solvents is 18.5 $MPa^{1/2}$ or more, and it is more preferable that the SP values of all the solvents are 18.5 $MPa^{1/2}$ or more.

As the second solvent, a solvent having a higher SP value than the first solvent included in the first solution is preferable from the viewpoints that the aggregation of the specific photoacid generators is further suppressed and the performance of suppressing defects of a pattern formed is more excellent. Furthermore, in a case where a plurality of kinds of the first solvents are used in combination as the first solvent and/or in a case where a plurality of kinds of the second solvents are used in combination as the second solvent, it is preferable that all the solvents corresponding to the second solvent have higher SP values than the solvent corresponding to the first solvent.

As a specific combination of the first solvent and the second solvent, it is preferable that the SP value of the first solvent is less than 18.5 MPa$^{1/2}$, and the SP value of the second solvent is 18.5 MPa$^{1/2}$ or more.

The second solution may include other components other than the specific photoacid generator and the second solvent, but it is preferable that the second solution substantially does not include an acid-decomposable resin. Here, the expression "the second solution substantially does not include an acid-decomposable resin" is intended to mean that a content of the acid-decomposable resin is 3.0% by mass or less with respect to a total mass of the second solution, and the content is preferably 2.0% by mass or less, more preferably 1.0% by mass or less, still more preferably 0.5% by mass or less, and particularly preferably 0.3% by mass or less. Furthermore, a lower limit value thereof is 0% by mass.

Above all, the second solution preferably substantially does not include other components other than the specific photoacid generator and the solvent. Here, the expression "the second solution substantially does not include other components other than the specific photoacid generator and the solvent" is intended to mean that a total content of other components other than the specific photoacid generator and the solvent is 3.0% by mass or less with respect to a total mass of the second solution, and the content is preferably 2.0% by mass or less, more preferably 1.0% by mass or less, still more preferably 0.5% by mass or less, and particularly preferably 0.3% by mass or less with respect to the total mass of the second solution. Furthermore, a lower limit value thereof is 0% by mass.

The concentration of solid contents of the second solution is not particularly limited, and is, for example, 1.0% to 30.0% by mass, and preferably 5.0% to 30.0% by mass. The concentration of solid contents is a mass percentage of the mass of the component excluding the solvent with respect to the total mass of the second solution.

(Method for Preparing Second Solution)

A method for preparing the second solution is not particularly limited, and it is preferable to mix the specific photoacid generator and the second solvent so that the above-mentioned concentration of solid contents is obtained, followed by stirring the mixture.

A stirring time is not particularly limited, but is preferably 1 hour or more, and more preferably 5 hours or more. A longer stirring time is more preferable, and the stirring time is, for example, 12 hours.

A stirring temperature is not particularly limited, but is preferably 15° C. to 25° C.

(Procedure of Step B3)

The step B3 is a step of mixing the first solution with the second solution prepared in the step B2.

A method of mixing the first solution with the second solution is not particularly limited.

It is preferable to stir the obtained mixed liquid after mixing the first solution with the second solution.

A stirring time is not particularly limited, but is preferably 1 hour or more, and more preferably 5 hours or more. A longer stirring time is more preferable, and the stirring time is, for example, 12 hours.

A stirring temperature is not particularly limited, but from the viewpoint that the aggregation of the specific photoacid generators can be further suppressed, a higher temperature is desirable, and the stirring temperature is preferably 10° C. or higher. An upper limit value of the stirring temperature is preferably 40° C. or lower from the viewpoint that stacking due to a change in the alignment of the specific photoacid generator can be suppressed.

<Other Steps (Step C)>

The production method of the embodiment of the present invention may further include other steps (hereinafter also referred to as a "step C").

Hereinbelow, an example of the production method of the embodiment of the present invention, including the step A, the step B, and the step C, will be shown.

A blending amount of each of the acid-decomposable resin, the specific photoacid generator, and other components blended in the resist composition in the following production method can be appropriately set according to the blending amount of each of target resist compositions. A suitable aspect of the blending amount of each of the components in the resist composition is as described above.

Embodiment 1 of Production Method

A production method of an embodiment 1 includes a step A, a step B1, and the following step C1. A resist composition is prepared through the step C1.

Step A: A step of preparing a first solution including an acid-decomposable resin and a first solvent Step B1: A step of directly mixing the first solution with a specific photoacid generator Step C1: A step of further mixing other components to be blended in the resist composition with a solution obtained in the step B1 and/or through the step B1

Furthermore, the step A and the step B1 are as described above.

In addition, the other components to be blended in the resist composition are also as described above.

Moreover, in the step C1, in a case where other components to be further blended in the resist composition are further mixed with a solution obtained in the step B1 and/or through the step B1, it is also preferable that such other components are the first solvent used in the step A. In the step C1, in a case where the first solvent used in the step A is further added to the solution obtained in the step B1 and/or through the step B1, a concentration of solid contents of the first solution is preferably adjusted to 5.0% to 20.0% by mass. In a case where the concentration of solid contents of the first solution is 5.0% by mass or more, a concentration of the acid-decomposable resin is relatively high (that is, an abundance in the solution is relatively high), and thus, the solubility of the specific photoacid generator in the first solvent is further improved and the performance of suppressing defects of a pattern formed is more excellent. On the other hand, in a case where the concentration of solid contents of the first solution is 20.0% by mass or less, the aggregation of the acid-decomposable resin in the first solution is further suppressed and the performance of suppressing defects of a pattern formed is more excellent.

Embodiment 2 of Production Method

A production method of an embodiment 2 includes a step A, a step B2, a step B3, and the following step C2. A resist composition is prepared through the step C2.

Step A: A step of preparing a first solution including an acid-decomposable resin and a first solvent Step B2: A step of preparing a second solution including a specific photoacid generator and a second solvent Step B3: A step of mixing the first solution with the second solution Step C2: A step of further mixing other components to be blended in the resist composition with a solution obtained through the step B3 (hereinafter also referred to as a "third solution")

Furthermore, the step A, the step B2, and the step B3 are as described above.

In addition, the second solvent preferably has a higher SP value than the first solvent. The SP values of the first solvent and the second solvent are as described above.

In addition, the other components to be blended in the resist composition are also as described above. Moreover, in the step C2, in a case where other components to be further blended in the resist composition are further mixed with a solution obtained through the step B3, it is also preferable that such other components are the first solvent used in the step A. In the step C2, in a case where the first solvent used in the step A is further added to the solution obtained through the step B3, a concentration of solid contents of the first solution is preferably adjusted to 5.0% to 20.0% by mass. In a case where the concentration of solid contents of the first solution is 5.0% by mass or more, a concentration of the acid-decomposable resin is relatively high (that is, an abundance in the solution is relatively high), and thus, the solubility of the specific photoacid generator in the first solvent is further improved and the performance of suppressing defects of a pattern formed is more excellent. On the other hand, in a case where the concentration of solid contents of the first solution is 20.0% by mass or less, the aggregation of the acid-decomposable resin in the first solution is further suppressed and the performance of suppressing defects of a pattern formed is more excellent.

The embodiment 2 of the production method preferably satisfies the following condition T1 (preferably the following condition T2) from the viewpoint that the performance of suppressing defects of a pattern formed is more excellent.

Condition T1: The method includes a step A, a step B2', a step B3, and the following step C2.

Step A: A step of preparing a first solution including an acid-decomposable resin and a first solvent Step B2': A step of preparing a second solution including a specific photoacid generator and a second solvent having a higher SP value than the first solvent Step B3: A step of mixing the first solution with the second solution Step C2: A step of further mixing other components to be blended in the resist composition with a solution obtained through the step B3 (a third solution)

Condition T2: The method includes a step A', a step B2", a step B3, and the following step C2 are included.

Step A': A step of preparing a first solution including an acid-decomposable resin and a first solvent having an SP value of less than 18.5 MPa$^{1/2}$ Step B2": A step of preparing a second solution including a specific photoacid generator and a second solvent having an SP value of 18.5 MPa$^{1/2}$ or more Step B3: A step of mixing the first solution with the second solution Step C2: A step of further mixing other components to be blended in the resist composition with a solution obtained through the step B3 (a third solution).

Embodiment 3 of Production Method

A production method of an embodiment 3 includes a step A", a step B2, a step B3, and the following step C3. A resist composition is prepared through the step C3.

Step A": A step of preparing a first solution having a concentration of solid contents of 5.0% to 20.0% by mass, which includes an acid-decomposable resin and a first solvent Step B2: A step of preparing a second solution including a specific photoacid generator and a second solvent Step B3: A step of mixing the first solution with the second solution Step C3: A step of further mixing the first solvent and other components to be optionally blended in the resist composition with the solution obtained through the step B3 (hereinafter also referred to as a "third solution").

That is, the production method of the embodiment 3 is a method in which the first solvent (and optionally other components constituting the resist composition) is further added to a third solution obtained by mixing the first solution having a concentration of solid contents of 5.0% to 20.0% by mass with the second solution, thereby producing a resist composition. In a case where the concentration of solid contents of the first solution is 5.0% by mass or more, a concentration of the acid-decomposable resin is relatively high (that is, an abundance in the solution is relatively high), and thus, in the step C3, the solubility of the specific photoacid generator in the first solvent is further improved and the performance of suppressing defects of a pattern formed is more excellent. On the other hand, in a case where the concentration of solid contents of the first solution is 20.0% by mass or less, the aggregation of the acid-decomposable resin in the first solution is further suppressed and the performance of suppressing defects of a pattern formed is more excellent. That is, in a case of using the production method of the embodiment 3, the performance of suppressing defects of a pattern formed is more excellent.

Furthermore, the step B2 and the step B3 are as described above.

In addition, the second solvent preferably has a higher SP value than the first solvent. The SP values of the first solvent and the second solvent are as described above.

In addition, the other components to be blended in the resist composition are also as described above.

The step C3 is preferably a step of further mixing the first solvent and other components to be blended in the resist composition with a solution obtained through the step B3 (third solution).

It is preferable that the embodiment 3 of the production method satisfies the following condition T3 from the viewpoint that the performance of suppressing defects of a pattern formed is more excellent.

Condition T3: The method includes a step A'", a step B2", a step B3, and the following step C3'.

Step A'": A step of preparing a first solution including an acid-decomposable resin and a first solvent having an SP value of less than 18.5 MPa$^{1/2}$, and having a concentration of solid contents of 5.0% to 20.0% by mass Step B2": A step of preparing a second solution including a specific photoacid generator and a second solvent having an SP value of 18.5 MPa$^{1/2}$ or more Step B3: A step of mixing the first solution with the second solution Step C3': A step of further mixing the first solvent and other components to be blended in the resist composition with a solution obtained through the step B3 (third solution).

<Purifying Treatment and Storing Method>

In the production method of the embodiment of the present invention, the resist composition that had been subjected to the above-mentioned steps A, B, and optional step C is preferably filtered (for circulatory filtration may be used), using a plurality of filters made of different materials. For example, it is preferable to connect a polyethylene-made filter with a pore diameter of 50 nm, a nylon-made filter with a pore diameter of 10 nm, and a polyethylene-made filter with a pore diameter of 3 to 5 nm in permuted connection, and then perform filtration. As for the filtration, a method of performing circulatory filtration twice or more is also preferable. Furthermore, the filtration the step also has an effect of reducing the content of the metal impurities in the composition. A smaller pressure difference among the filters is more preferable, and the pressure difference is generally 0.1 MPa or less, preferably 0.05 MPa or less, and more preferably 0.01 MPa or less. A smaller pressure difference between the filter and the charging nozzle is also preferable, and the pressure difference is generally 0.5 MPa or less, preferably 0.2 MPa or less, and more preferably 0.1 MPa or less.

In addition, as a method for performing circulatory filtration using a filter in the production of the resist composition, for example, a method of performing circulatory filtration twice or more using a polytetrafluoroethylene-made filter having a pore diameter of 50 nm is also preferable.

Moreover, it is preferable to subject the inside of a device for producing the resist composition to gas replacement with an inert gas such as nitrogen. With this, it is possible to suppress dissolution of an active gas such as oxygen in the resist composition.

After being filtered by a filter, the resist composition is charged into a clean container. It is preferable that the resist composition charged in the container is subjected to refrigeration storage. This enables performance deterioration caused by the lapse of time to be suppressed. A shorter time from completion of the charge of the resist composition into the container to initiation of cold storage is more preferable, and the time is generally 24 hours or shorter, preferably 16 hours or shorter, more preferably 12 hours or shorter, and still more preferably 10 hours or shorter. The storage temperature is preferably 0° C. to 15° C., more preferably 0° C. to 10° C., and still more preferably 0° C. to 5° C.

In addition, the resist composition produced by the production method of the embodiment of the present invention preferably has a reduced content of metal atoms.

Hereinafter, a specific example of a method for reducing the content of metal atoms in the resist composition will be described.

Examples of the method for reducing the content of the metal atoms in the resist composition include a method for adjusting the content by filtration using a filter. As for the filter pore diameter, the pore size is preferably less than 100 nm, more preferably 10 nm or less, and still more preferably 5 nm or less. As the filter, a polytetrafluoroethylene-made, polyethylene-made, or nylon-made filter is preferable. The filter may include a composite material in which the filter material is combined with an ion exchange medium. As the filter, a filter which has been washed with an organic solvent in advance may be used. In the step of filter filtration, plural kinds of filters connected in series or in parallel may be used. In a case of using the plural kinds of filters, a combination of filters having different pore diameters and/or materials may be used. In addition, various materials may be filtered plural times, and the step of filtering plural times may be a circulatory filtration step.

In addition, examples of a method for reducing the content of the metal atoms in the resist composition include a method of selecting raw materials having a low content of metals as raw materials constituting various materials in the resist composition, a method of subjecting raw materials constituting various materials in the resist composition to filter filtration, and a method of performing distillation under the condition for suppressing the contamination as much as possible by, for example, lining the inside of a device with TEFLON (registered trademark).

Moreover, as the method for reducing the content of the metal atoms in the resist composition, removal with an adsorbing material may be performed, in addition to the above-mentioned filter filtration, and the filter filtration and the adsorbing material may be used in combination. As the adsorbing material, known adsorbing materials can be used, and for example, inorganic adsorbing materials such as silica gel and zeolite, and organic adsorbing materials such as activated carbon can be used.

In addition, in order to reduce the content of the metal atoms in the resist composition, it is necessary to prevent the incorporation of metal impurities in the production process. Sufficient removal of metal impurities from a production device can be confirmed by measuring the content of metal components included in a washing liquid used to wash the production device.

[Use]

The resist composition obtained by the production method of the embodiment of the present invention corresponds to a resist composition whose properties change in response to irradiation with actinic rays or radiation. More specifically, the resist composition obtained by the production method of the embodiment of the present invention relates to a resist composition which can be used in a step of manufacturing a semiconductor such as an integrated circuit (IC), for the manufacture of a circuit board for a liquid crystal, a thermal head, or the like, the manufacture of a mold structure for imprinting, other photofabrication processes, a planographic printing plate, or an acid-curable composition.

A pattern formed in the present invention can be used in an etching step, an ion implantation step, a bump electrode forming step, a rewiring forming step, a microelectromechanical system (MEMS), or the like.

[Pattern Forming Method]

The pattern forming method of the embodiment of the present invention includes the following steps 1 to 3.

Step 1: A step of forming a resist film on a support (on a substrate), using a resist composition obtained by the above-mentioned production method of the embodiment of the present invention Step 2: A step of exposing the resist film Step 3: A step of developing the exposed resist film, using a developer Hereinafter, the procedure of each of the steps will be described in detail.

[Step 1: Resist Film Forming Step]

The step 1 is a step of forming a resist film on a support (on a substrate), using the resist composition. Examples of a method of forming a resist film on a substrate, using the resist composition, include a method in which a resist composition is applied onto a substrate.

The resist composition can be applied onto a substrate (for example, silicon and silicon dioxide coating) as used in the manufacture of integrated circuit elements by a suitable application method such as ones using a spinner or a coater. As the application method, spin application using a spinner is preferable. The rotation speed upon spin application using a spinner is preferably 1,000 to 3,000 rpm.

After the application of the resist composition, the substrate may be dried to form a resist film. In addition, various underlying films (an inorganic film, an organic film, or an antireflection film) may be formed on the underlayer of the resist film.

Examples of the drying method include a method of heating and drying. The heating may be performed using a unit included in an ordinary exposure machine and/or an ordinary development machine, and may also be performed using a hot plate or the like. A heating temperature is preferably 80° C. to 150° C., more preferably 80° C. to 140° C., and still more preferably 80° C. to 130° C. A heating time is preferably 30 to 1,000 seconds, more preferably 60 to 800 seconds, and still more preferably 60 to 600 seconds.

A film thickness of the resist film is not particularly limited, but is preferably 10 to 150 nm, and more preferably 15 to 100 nm from the viewpoint that a fine pattern having higher accuracy can be formed.

Moreover, a topcoat may be formed on the upper layer of the resist film, using the topcoat composition.

It is preferable that the topcoat composition is not mixed with the resist film and can be uniformly applied onto the upper layer of the resist film.

Furthermore, it is preferable to dry the resist film before forming the topcoat. Then, the topcoat composition can be applied onto the obtained resist film by the same unit as the method for forming a resist film, and further dried to form a topcoat.

A film thickness of the topcoat is preferably 10 to 200 nm, and more preferably 20 to 100 nm.

The topcoat composition includes, for example, a resin, an additive, and a solvent.

As the resin, the same resin as the above-mentioned hydrophobic resin can be used. A content of the resin is preferably 50% to 99.9% by mass, and more preferably 60% to 99.7% by mass with respect to a total solid content of the topcoat composition.

As the additive, the above-mentioned acid diffusion control agent can be used. In addition, a compound having a radical trapping group such as a compound having an N-oxy free radical group can also be used. Examples of such a compound include a [4-(benzoyloxy)-2,2,6,6-tetramethylpiperidinooxy]radical. A content of the additive is preferably 0.01% to 20% by mass, and more preferably 0.1% to 15% by mass with respect to the total solid content of the topcoat composition.

It is preferable that the solvent does not dissolve a resist film, and examples of the solvent include an alcohol-based solvent (4-methyl-2-pentanol and the like), an ether-based solvent (diisoamyl ether and the like), an ester-based solvent, a fluorine-based solvent, and a hydrocarbon-based solvent (n-decane and the like).

The content of the solvent in the topcoat composition is preferably set so that the concentration of solid contents is 0.5% to 30% by mass, and more preferably set so that the concentration of solid contents is 1% to 20% by mass.

In addition, the topcoat composition may include a surfactant in addition to the above-mentioned additive, and as the surfactant, the same one as the surfactant which may be included in the resist composition can be used. A content of the surfactant is preferably 0.0001% to 2% by mass, and more preferably 0.0005% to 1% by mass with respect to the total solid content of the topcoat composition.

In addition, the topcoat is not particularly limited, a topcoat known in the related art can be formed by the methods known in the related art, and the topcoat can be formed, based on the description in paragraphs [0072] to [0082] of JP2014-059543A, for example.

It is preferable that a topcoat including a basic compound as described in JP2013-61648A, for example, is formed on a resist film. Specific examples of the basic compound which can be included in the topcoat include a basic compound which may be included in the above-mentioned resist composition.

In addition, the topcoat preferably includes a compound which includes at least one group or bond selected from the group consisting of an ether bond, a thioether bond, a hydroxyl group, a thiol group, a carbonyl bond, and an ester bond.

[Step 2: Exposing Step]

The step 2 is a step of exposing the resist film.

Examples of the exposing method include a method of irradiating the resist film formed with actinic rays or radiation through a predetermined mask.

Examples of the actinic rays or radiation include infrared light, visible light, ultraviolet light, far ultraviolet light, extreme ultraviolet light, X-rays, and electron beams, preferably a far ultraviolet light having a wavelength of 250 nm or less, more preferably a far ultraviolet light having a wavelength of 220 nm or less, and particularly preferably a far ultraviolet light having a wavelength of 1 to 200 nm, specifically, KrF excimer laser (248 nm), ArF excimer laser (193 nm), $F_2$ excimer laser (157 nm), EUV (13 nm), X-rays, and electron beams.

It is preferable to perform baking (heating) before performing development after the exposure. The baking accelerates a reaction in the exposed area, and the sensitivity and the pattern shape are improved.

A heating temperature is preferably 80° C. to 150° C., more preferably 80° C. to 140° C., and still more preferably 80° C. to 130° C.

A heating time is preferably 10 to 1,000 seconds, more preferably 10 to 180 seconds, and still more preferably 30 to 120 seconds.

The heating may be performed using a unit included in an ordinary exposure machine and/or an ordinary development machine, and may also be performed using a hot plate or the like.

This step is also referred to as a post-exposure baking.

[Step 3: Developing Step]

The step 3 is a step of developing the exposed resist film, using a developer, to form a pattern.

Examples of the developing method include a method in which a substrate is immersed in a tank filled with a developer for a certain period of time (a dip method), a method in which development is performed by heaping a developer up onto the surface of a substrate by surface tension, and then leaving it to stand for a certain period of time (a puddle method), a method in which a developer is sprayed on the surface of a substrate (a spray method), and a method in which a developer is continuously jetted onto a substrate rotating at a constant rate while scanning a developer jetting nozzle at a constant rate (a dynamic dispense method).

Furthermore, after the step of performing development, a step of stopping the development may be carried out while substituting the solvent with another solvent.

A developing time is not particularly limited as long as it is a period of time where the unexposed area of a resin is sufficiently dissolved, and is preferably 10 to 300 seconds, and more preferably 20 to 120 seconds.

The temperature of the developer is preferably 0° C. to 50° C., and more preferably 15° C. to 35° C.

Examples of the developer include an alkali developer and an organic solvent developer.

As the alkali developer, an aqueous alkali solution including an alkali is preferably used. The type of the aqueous alkali solution is not particularly limited, but examples thereof include an aqueous alkali solution including a quaternary ammonium salt typified by tetramethylammonium hydroxide, an inorganic alkali, a primary amine, a secondary amine, a tertiary amine, an alcoholamine, a cyclic amine, or the like. Among those, the aqueous solutions of the quaternary ammonium salts typified by tetramethylammonium hydroxide (TMAH) are preferable as the alkali developer. An appropriate amount of an alcohol, a surfactant, or the like may be added to the alkali developer. The alkali concentration of the alkali developer is usually 0.1% to 20% by mass. Furthermore, the pH of the alkali developer is usually 10.0 to 15.0.

The organic solvent developer is a developer including an organic solvent.

A vapor pressure of the organic solvent included in the organic solvent developer (in a case of a mixed solvent, a vapor pressure as a whole) is preferably 5 kPa or less, more preferably 3 kPa or less, and still more preferably 2 kPa or less at 20° C. By setting the vapor pressure of the organic solvent to 5 kPa or less, evaporation of the developer on a substrate or in a development cup is suppressed, the temperature uniformity in a wafer plane is improved, and as a result, the dimensional uniformity in the wafer plane is enhanced.

Examples of the organic solvent used in the organic solvent developer include known organic solvents, and include an ester-based solvent, a ketone-based solvent, an alcohol-based solvent, an amide-based solvent, an ether-based solvent, and a hydrocarbon-based solvent.

It is preferable to use an ester-based solvent having 7 or more carbon atoms (preferably having 7 to 14 carbon atoms, more preferably having 7 to 12 carbon atoms, and still more preferably having 7 to 10 carbon atoms), and 2 or less heteroatoms as the organic solvent included in the organic solvent developer from the viewpoint that the swelling of the resist film can be suppressed in a case where EUV and electron beams are used in the exposing step.

The heteroatom of the ester-based solvent is an atom other than a carbon atom and a hydrogen atom, and examples thereof include an oxygen atom, a nitrogen atom, and a sulfur atom. The number of the heteroatoms is preferably 2 or less.

As the ester-based solvent having 7 or more carbon atoms and 2 or less heteroatoms, amyl acetate, isoamyl acetate, 2-methylbutyl acetate, 1-methylbutyl acetate, hexyl acetate, pentyl propionate, hexyl propionate, butyl propionate, isobutyl isobutyrate, heptyl propionate, butyl butanoate, or the like is preferable, and isoamyl acetate is more preferable.

In a case where EUV and electron beams are used in the exposing step, a mixed solvent of the ester-based solvent and the hydrocarbon-based solvent or a mixed solvent of the ketone-based solvent and the hydrocarbon-based solvent may be used instead of the ester-based solvent having 7 or more carbon atoms and having 2 or less heteroatoms as the organic solvent included in the organic solvent developer. Also in this case, it is effective in suppressing the swelling of the resist film.

In a case where the ester-based solvent and the hydrocarbon-based solvent are used in combination, it is preferable to use isoamyl acetate as the ester-based solvent. In addition, from the viewpoint of adjusting the solubility of the resist film, a saturated hydrocarbon-based solvent (for example, octane, nonane, decane, dodecane, undecane, and hexadecane) is preferable as the hydrocarbon-based solvent.

In a case where the ketone-based solvent and the hydrocarbon-based solvent are used in combination, it is preferable to use 2-heptanone as the ketone-based solvent. In addition, from the viewpoint of adjusting the solubility of the resist film, a saturated hydrocarbon-based solvent (for example, octane, nonane, decane, dodecane, undecane, and hexadecane) is preferable as the hydrocarbon-based solvent.

In a case of using the mixed solvent, the content of the hydrocarbon-based solvent depends on the solvent solubility of the resist film, it is not particularly limited, and therefore, the content may be appropriately adjusted to determine a necessary amount of the hydrocarbon-based solvent.

A plurality of the organic solvents may be mixed or the organic solvent may be used in admixture with a solvent other than those described above or water. It should be noted that in order to fully exert the effect of the present invention, the moisture content of the developer as a whole is preferably less than 10% by mass, and the developer is more preferably substantially free of the moisture. The concentration of the organic solvent (in a case of mixing a plurality of the organic solvents, a total thereof) in the developer is preferably 50% by mass or more, more preferably 50% to 100% by mass, still more preferably 85% to 100% by mass, particularly preferably 90% to 100% by mass, and most preferably 95% to 100% by mass.

[Other Steps]

It is preferable that the pattern forming method includes a step of performing washing using a rinsing liquid after the step 3.

Examples of the rinsing liquid used in the rinsing step after the step of performing development using the developer include pure water. Furthermore, an appropriate amount of a surfactant may be added to pure water.

An appropriate amount of a surfactant may be added to the rinsing liquid.

A method for the rinsing step is not particularly limited, but examples thereof include a method in which a rinsing liquid is continuously jetted on a substrate rotated at a constant rate (a rotation application method), a method in which a substrate is immersed in a tank filled with a rinsing liquid for a certain period of time (a dip method), and a method in which a rinsing liquid is sprayed on a substrate surface (a spray method).

Furthermore, the pattern forming method of the embodiment of the present invention may include a heating step (postbaking) after the rinsing step. By the present step, the developer and the rinsing liquid remaining between and inside the patterns are removed by baking. In addition, the present step also has an effect that a resist pattern is annealed and the surface roughness of the pattern is improved. The heating step after the rinsing step is usually performed at 40° C. to 250° C. (preferably 90° C. to 200° C.) for usually 10 seconds to 3 minutes (preferably 30 to 120 seconds).

In addition, an etching treatment on the substrate may be carried out using a pattern formed as a mask. That is, the substrate (or the underlayer film and the substrate) may be processed using the pattern thus formed in the step 3 as a mask to form a pattern on the substrate.

A method for processing the substrate (or the underlayer film and the substrate) is not particularly limited, but a method in which a pattern is formed on a substrate by subjecting the substrate (or the underlayer film and the substrate) to dry etching using the pattern thus formed in the step 3 as a mask is preferable.

The dry etching may be one-stage etching or multi-stage etching. In a case where the etching is etching including a plurality of stages, the etchings at the respective stages maybe the same treatment or different treatments.

For etching, any of known methods can be used, and various conditions and the like are appropriately determined according to the type of a substrate, usage, and the like. Etching can be carried out, for example, in accordance with Journal of The International Society for Optical Engineering (Proc. of SPIE), Vol. 6924, 692420 (2008), JP2009-267112A, and the like. In addition, the etching can also be carried out in accordance with "Chapter 4 Etching" in "Semiconductor Process Text Book, 4$^{th}$ Ed., published in 2007, publisher: SEMI Japan".

Among those, oxygen plasma etching is preferable as the dry etching.

Various materials (for example, a developer, a rinsing liquid, a composition for forming an antireflection film, and a composition for forming a topcoat) other than the resist composition used in the pattern forming method of the embodiment of the present invention preferably have smaller amounts of impurities such as a metal (for example, Na, K, Ca, Fe, Cu, Mg, Al, Li, Cr, Ni, Sn, Ag, As, Au, Ba, Cd, Co, Pb, Ti, V, W, and Zn). The content of the impurities included in these materials is preferably for example, 1 ppm by mass or less.

Examples of a method for reducing impurities such as a metal in various materials other than the resist composition include filtration using a filter. As for the filter pore diameter, the pore size is preferably less than 100 nm, more preferably 10 nm or less, and still more preferably 5 nm or less. As the filter, a polytetrafluoroethylene-made, polyethylene-made, or nylon-made filter is preferable. The filter may include a composite material in which the filter material is combined with an ion exchange medium. As the filter, a filter which has been washed with an organic solvent in advance may be used. In the step of filter filtration, plural kinds of filters connected in series or in parallel may be used. In a case of using the plural kinds of filters, a combination of filters having different pore diameters and/or materials may be used. In addition, various materials may be filtered plural times, and the step of filtering plural times may be a circulatory filtration step.

In addition, examples of a method for reducing impurities such as a metal in various materials other than the resist composition include a method of selecting raw materials having a low content of metals as raw materials constituting various materials, a method of subjecting raw materials constituting various materials to filter filtration, and a method of performing distillation under the condition for suppressing the contamination as much as possible by, for example, lining the inside of a device with TEFLON (registered trademark).

Moreover, as the method for reducing impurities such as a metal in various materials other than the resist composition, removal of impurities with an adsorbing material may be performed, in addition to the above-mentioned filter filtration, and the filter filtration and the adsorbing material may be used in combination. As the adsorbing material, known adsorbing materials can be used, and for example, inorganic adsorbing materials such as silica gel and zeolite, and organic adsorbing materials such as activated carbon can be used. It is necessary to prevent the incorporation of metal impurities in the production process in order to reduce the impurities such as a metal included in the various materials other than the resist composition. Sufficient removal of metal impurities from a production device can be confirmed by measuring the content of metal components included in a washing liquid used to wash the production device.

A conductive compound may be added to an organic treatment liquid such as a rinsing liquid in order to prevent breakdown of chemical liquid pipes and various parts (a filter, an O-ring, a tube, or the like) due to electrostatic charging, and subsequently generated electrostatic discharging. The conductive compound is not particularly limited, but examples thereof include methanol. The addition amount is not particularly limited, but from the viewpoint that preferred development characteristics or rinsing characteristics are maintained, the addition amount is preferably 10% by mass or less, and more preferably 5% by mass or less.

For members of the chemical liquid pipe, various pipes coated with stainless steel (SUS), or a polyethylene, polypropylene, or fluorine resin (a polytetrafluoroethylene or perfluoroalkoxy resin, or the like) that has been subjected to an antistatic treatment can be used. In the same manner, for the filter or the O-ring, polyethylene, polypropylene, or a fluorine resin (a polytetrafluoroethylene or perfluoroalkoxy resin, or the like) that has been subjected to an antistatic treatment can be used.

A method for improving the surface roughness of a pattern may be applied to a pattern formed by the pattern forming method of the embodiment of the present invention. Examples of the method for improving the surface roughness of the pattern include the method of treating a pattern by a plasma of a hydrogen-containing gas disclosed in WO2014/002808A. Additional examples of the method include known methods as described in JP2004-235468A, US2010/0020297A, JP2008-83384A, and Proc. of SPIE Vol. 8328 83280N-1 "EUV Resist Curing Technique for LWR Reduction and Etch Selectivity Enhancement".

In a case where a pattern formed is in the form of a line, an aspect ratio determined by dividing the height of the pattern with the line width is preferably 2.5 or less, more preferably 2.1 or less, and still more preferably 1.7 or less.

In a case where a pattern formed is in the form of a trench (groove) pattern or a contact hole pattern, an aspect ratio determined by dividing the height of the pattern with the trench width or the hole diameter is preferably 4.0 or less, more preferably 3.5 or less, and still more preferably 3.0 or less.

The pattern forming method of the embodiment of the present invention can also be used for forming a guide pattern in a directed self-assembly (DSA) (see, for example, ACS Nano Vol. 4, No. 8, Pages 4815-4823).

In addition, a pattern formed by the method can be used as a core material (core) of the spacer process disclosed in, for example, JP1991-270227A (JP-H03-270227A) and JP2013-164509A.

[Method for Manufacturing Electronic Device]

In addition, the present invention further relates to a method for manufacturing an electronic device, including the pattern forming method. Examples of the electronic device include electronic devices which can be mounted on electric and electronic equipment (for example, home appliances, office automation (OA)-related equipment, media-related equipment, optical equipment, telecommunication equipment, and the like).

EXAMPLES

Hereinafter, the present invention will be described in more detail with reference to Examples. The materials, the amounts of materials used, the proportions, the treatment details, the treatment procedure, and the like shown in Examples below may be appropriately modified as long as the modifications do not depart from the spirit of the present invention. Therefore, the scope of the present invention should not be construed as being limited to Examples shown below.

[Production of Actinic Ray-Sensitive or Radiation-Sensitive Resin Composition (Resist Composition)]

Hereinbelow, first, various components to be blended in the resist composition will be described.

[Preparation of First Solution]

Hereinafter, the first solutions shown in Table 4 and Table 7 will be described.

The first solutions (X-1 to X-22) shown in Table 4 and Table 7 are shown in Table 2.

Hereinbelow, various components included in the first solution shown in Table 2 will be described, and then a method for preparing the first solution will be described.

<Various Components>

(Acid-Decomposable Resin (Resin A))

Resins A (resins A-1 to A-16) shown in Table 2 are shown below.

As the resins A-1 to A-16, those synthesized according to a method for synthesizing a resin A-1 (Synthesis Example 1) which will be described later were used. The compositional ratio (molar ratio; corresponding in order from the left) of the respective repeating units shown below, the weight-average molecular weight (Mw), and the dispersity (Mw/Mn) are shown in Table 1.

Furthermore, the weight-average molecular weight (Mw) and the dispersity (Mw/Mn) of the resins A-1 to A-16 were measured by GPC (carrier: tetrahydrofuran (THF)) (an amount expressed in terms of polystyrene). In addition, the compositional ratio (ratio based on % by mole) of the resin was measured by $^{13}$C-nuclear magnetic resonance (NMR).

TABLE 1

| | Molar ratio of repeating unit | | | | Mw | Mw/Mn |
|---|---|---|---|---|---|---|
| Resin A-1 | 50 | 50 | — | — | 6,500 | 1.52 |
| Resin A-2 | 45 | 55 | — | — | 8,300 | 1.65 |
| Resin A-3 | 40 | 50 | 10 | — | 12,000 | 1.68 |
| Resin A-4 | 25 | 30 | 30 | 15 | 8,600 | 1.63 |
| Resin A-5 | 40 | 10 | 30 | 20 | 9,600 | 1.72 |
| Resin A-6 | 30 | 20 | 40 | 10 | 7,500 | 1.54 |
| Resin A-7 | 40 | 10 | 10 | 40 | 6,500 | 1.63 |
| Resin A-8 | 30 | 10 | 60 | — | 11,500 | 1.56 |
| Resin A-9 | 40 | 10 | 50 | — | 9,200 | 1.66 |
| Resin A-10 | 30 | 20 | 50 | — | 7,600 | 1.56 |
| Resin A-11 | 35 | 10 | 55 | — | 8,400 | 1.58 |
| Resin A-12 | 30 | 20 | 40 | 10 | 9,100 | 1.65 |
| Resin A-13 | 15 | 30 | 35 | 20 | 8,300 | 1.61 |
| Resin A-14 | 40 | 50 | 10 | — | 8,500 | 1.62 |
| Resin A-15 | 20 | 20 | 40 | 20 | 13,000 | 1.7 |
| Resin A-16 | 40 | 50 | 10 | — | 16,000 | 1.72 |

The structural formulae of the resins A-1 to A-16 shown in Table 1 are shown below.

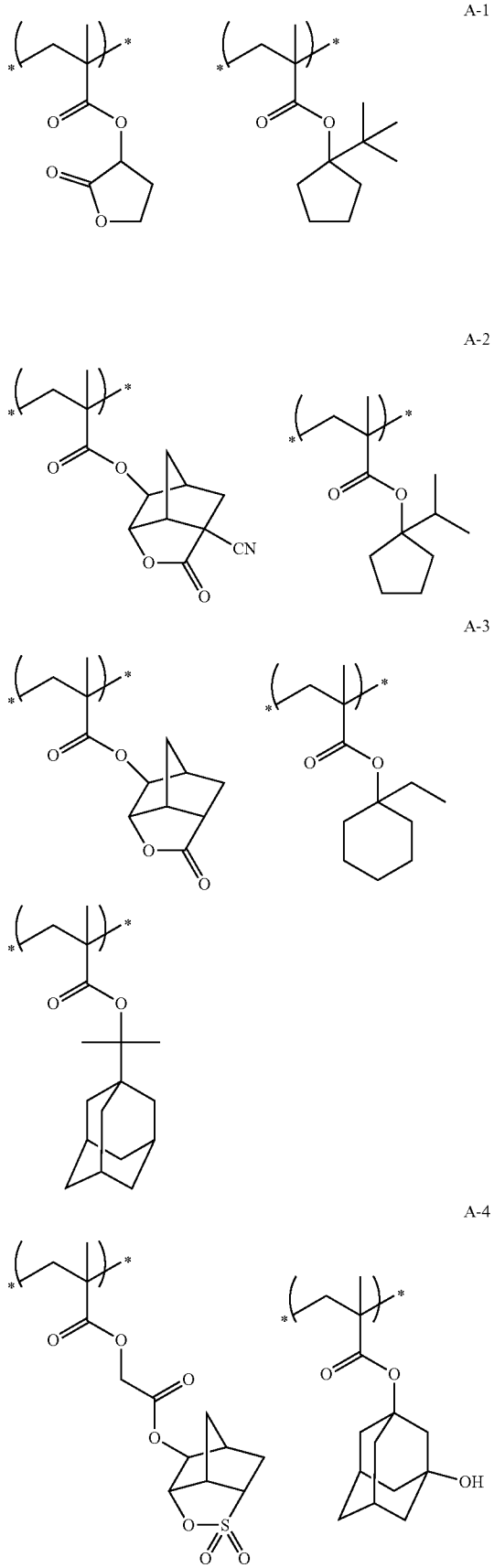

-continued
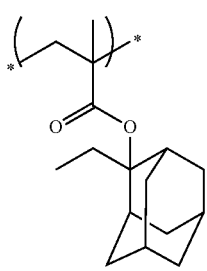 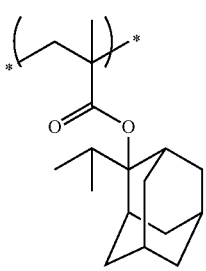
A-5
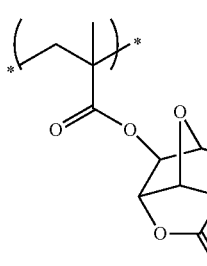 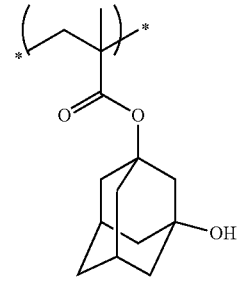
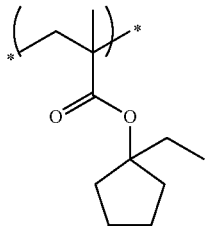 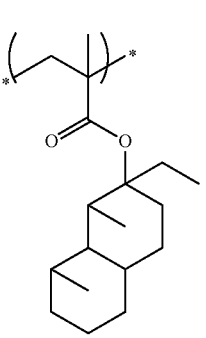
A-6
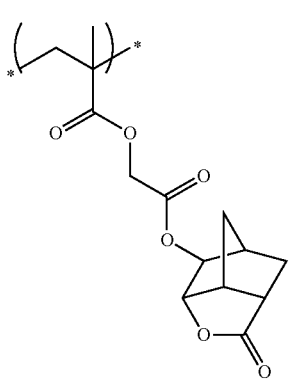
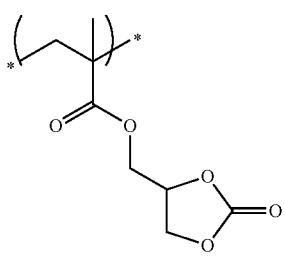 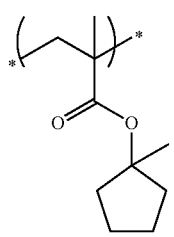
-continued
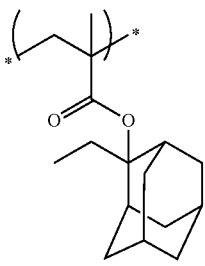
A-7
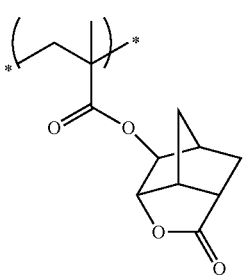 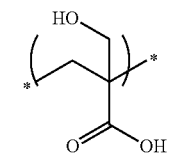
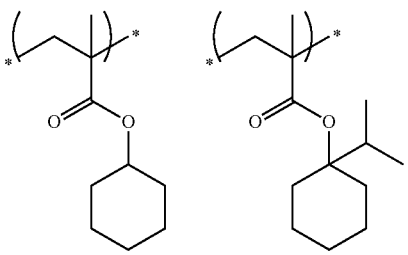
A-8
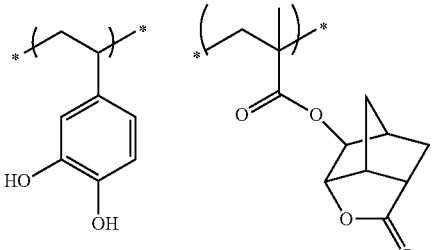
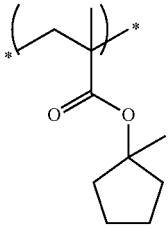
A-9
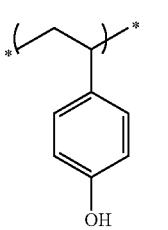

-continued
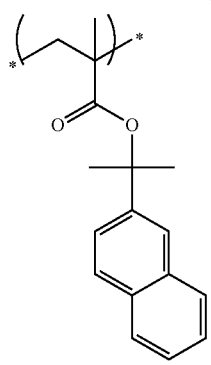
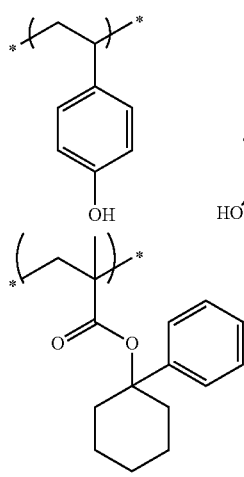
A-10
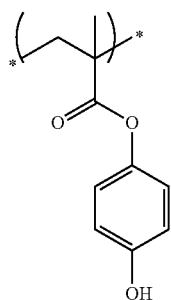
A-11
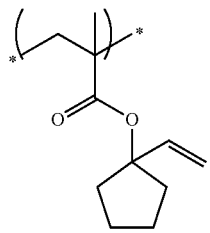
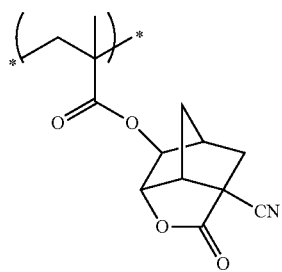
A-12
-continued
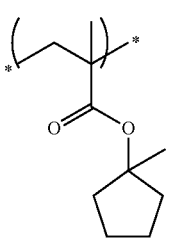 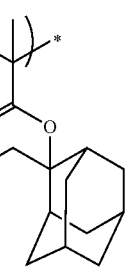
A-13
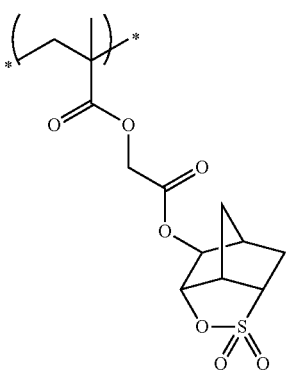 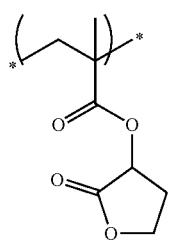
A-14
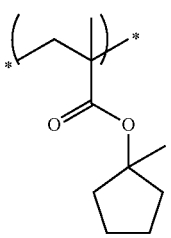 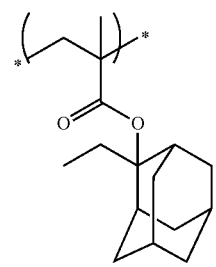

-continued

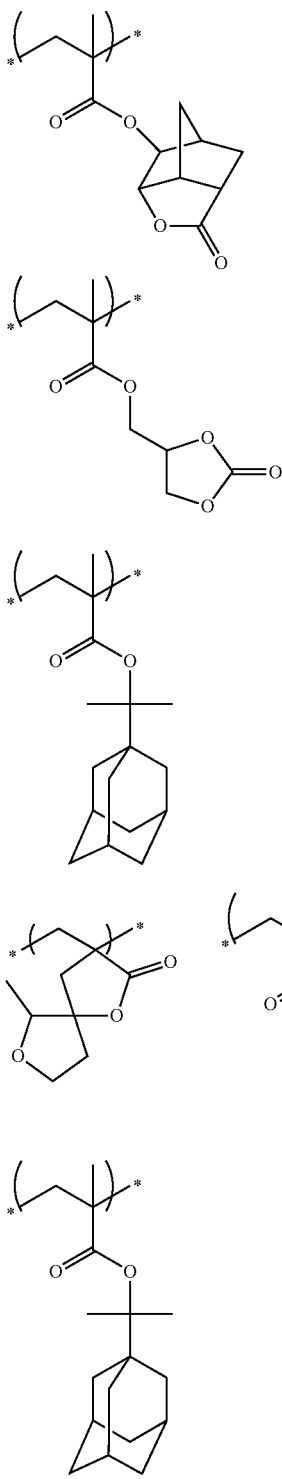

Synthesis Example 1: Synthesis of Resin A-1

Cyclohexanone (113 g) was heated to 80° C. under a nitrogen stream. While stirring this liquid, a mixed solution of a monomer represented by Formula M-1 (25.5 g), a monomer represented by Formula M-2 (31.6 g), cyclohexanone (210 g), and dimethyl 2,2'-azobisisobutyrate [V-601, manufactured by FUJIFILM Wako Pure Chemical Corporation](6.21 g) was added dropwise thereto over 6 hours to obtain a reaction solution. After completion of dropwise addition, the reaction solution was further stirred at 80° C. for 2 hours. The obtained reaction solution was cooled, then reprecipitated with a large amount of methanol/water (mass ratio: 9:1), and filtered, and the obtained solid was vacuum-dried to obtain 52 g of a resin A-1.

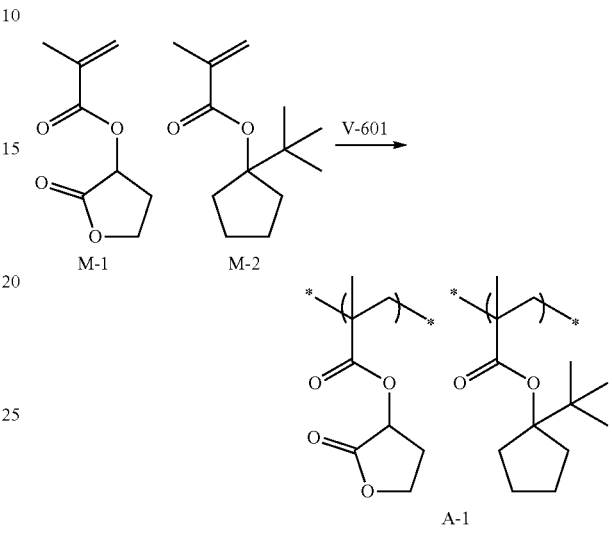

The resin A-1 thus obtained had a weight-average molecular weight (Mw: expressed in terms of polystyrene) of 6,500 and a dispersity (Mw/Mn) of 1.52, as determined from GPC (carrier: tetrahydrofuran (THF)). The compositional ratio measured by $^{13}$C-nuclear magnetic resonance (NMR) was 50/50 expressed in terms of a molar ratio.

(First Solvent)

First solvents (solvents C-1 to C-3) shown in Table 2 are shown below.

C-1: Propylene glycol monomethyl ether acetate (abbreviation: PGMEA, SP value: 17.9 MPa$^{1/2}$)
C-2: 2-Heptanone (SP value: 18.1 MPa$^{1/2}$)
C-3: Cyclohexanone (SP value: 20.0 MPa$^{1/2}$)

<Preparation of First Solution>

The resin (A) and the first solvent were mixed to reach a concentration of solid contents shown in Table 2, and the mixture was stirred for 6 hours to prepare a first solution (solutions X-1 to X-22). Furthermore, in the first solution, the solid content means all the components excluding the solvent.

TABLE 2

| | Composition of first solution | | | |
|---|---|---|---|---|
| | | First solvent | | |
| | Resin (A) | Type | SP value (MPa$^{1/2}$) | Concentration of solid contents (% by mass) |
| X-1 | A-1 | C-1 | 17.9 | 4.4 |
| X-2 | A-1 | C-1 | 17.9 | 10.0 |
| X-3 | A-1 | C-1 | 17.9 | 25.0 |
| X-4 | A-2 | C-1 | 17.9 | 12.0 |
| X-5 | A-3 | C-2 | 18.1 | 15.0 |
| X-6 | A-4 | C-1 | 17.9 | 9.0 |
| X-7 | A-5 | C-1 | 17.9 | 10.0 |
| X-8 | A-6 | C-1 | 17.9 | 11.0 |
| X-9 | A-7 | C-1 | 17.9 | 8.0 |

TABLE 2-continued

| | | Composition of first solution | | |
| | | First solvent | | |
| Resin (A) | Type | SP value (MPa$^{1/2}$) | Concentration of solid contents (% by mass) |
|---|---|---|---|---|
| X-10 | A-8 | C-1 | 17.9 | 1.6 |
| X-11 | A-8 | C-1 | 17.9 | 11.0 |
| X-12 | A-8 | C-1 | 17.9 | 23.0 |
| X-13 | A-9 | C-1 | 17.9 | 10.0 |
| X-14 | A-10 | C-2 | 18.1 | 7.0 |
| X-15 | A-11 | C-1 | 17.9 | 8.0 |
| X-16 | A-1 | C-3 | 20.0 | 10.0 |
| X-17 | A-8 | C-3 | 20.0 | 11.0 |
| X-18 | A-12 | C-1 | 17.9 | 12.0 |
| X-19 | A-13 | C-1 | 17.9 | 15.0 |
| X-20 | A-14 | C-1 | 17.9 | 10.0 |
| X-21 | A-15 | C-1 | 17.9 | 13.0 |
| X-22 | A-16 | C-1 | 17.9 | 9.0 |

[Preparation of Second Solution]

Second solutions shown in Table 4 and Table 7 will be described below.

The second solutions (Y-1 to Y-24, YY-1, and YY-2) are shown in Table 3, Table 4, and Table 7.

Hereinbelow, various components included in the second solution shown in Table 3 will be described, and then a method for preparing the second solution will be described.

<Various Components>

(Specific Photoacid Generator)

The structures of specific photoacid generators B (compounds B-1 to B-24) shown in Table 3 are shown below. Furthermore, the compounds B-1 to B-18 and B-21 to B-24 correspond to the above-mentioned compound (I), the compound B-20 corresponds to the above-mentioned compound (II), and the compound B-19 corresponds to the above-mentioned compound (III).

B-1

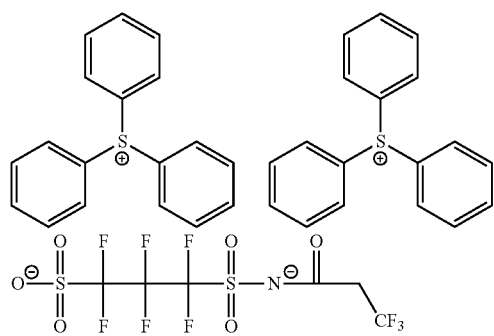

B-2

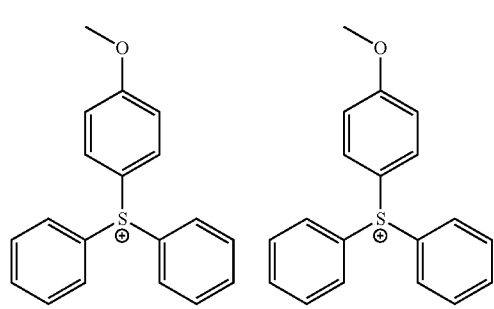

B-3

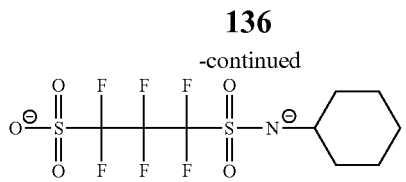

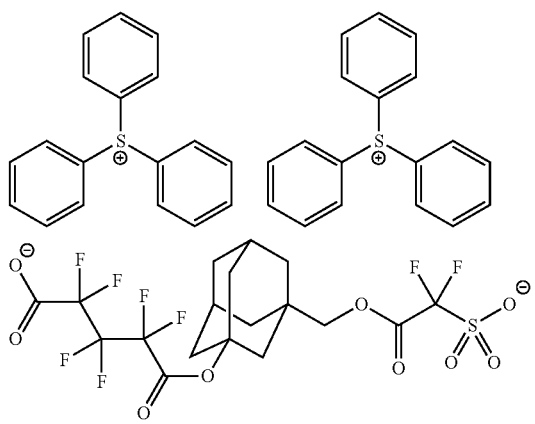

B-4

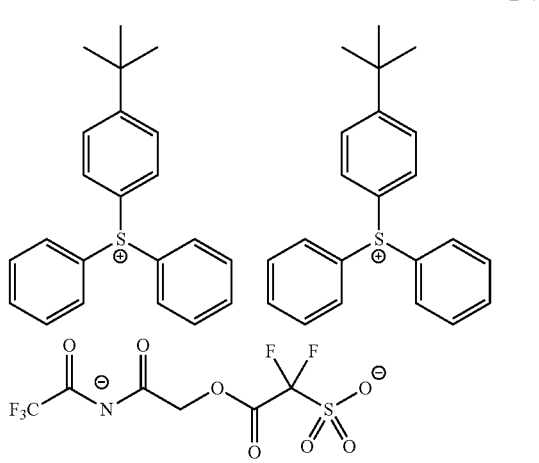

B-5

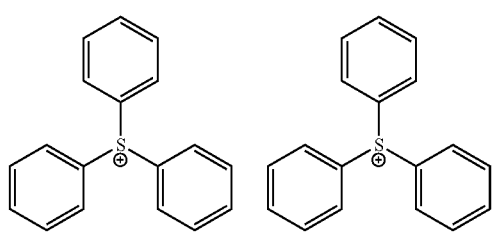

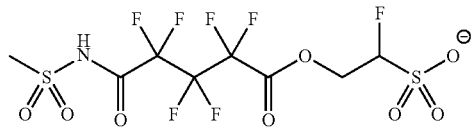

B-6
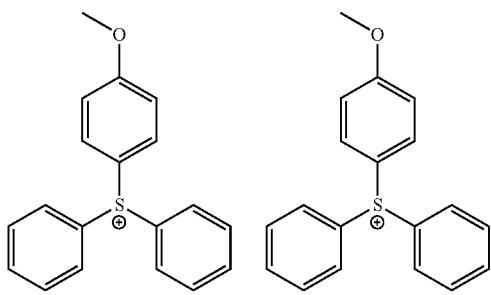
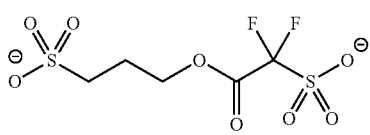
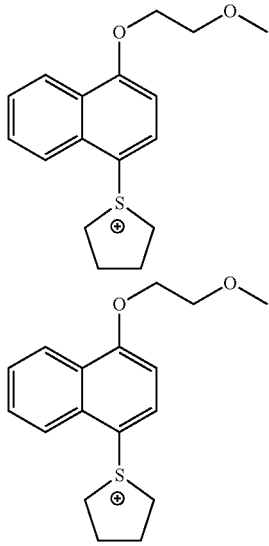
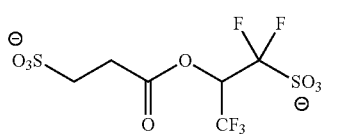
B-7
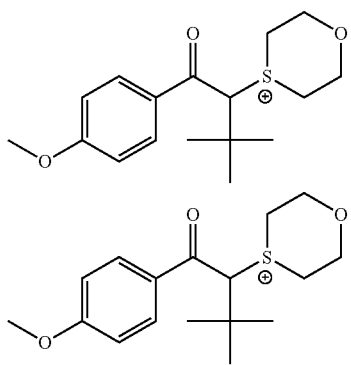
B-8
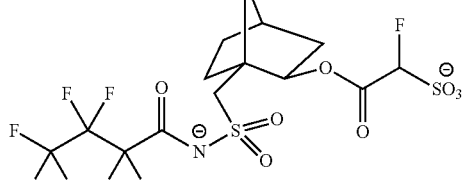
B-9
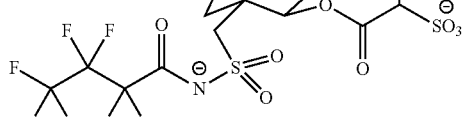
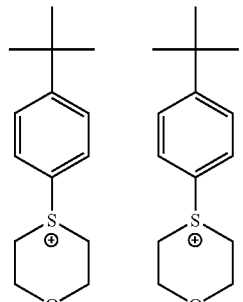
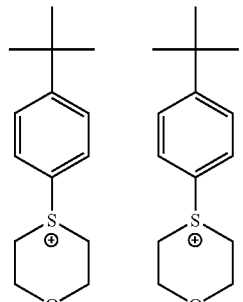
B-10
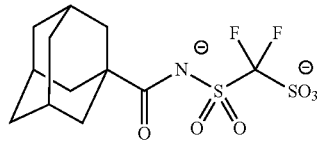
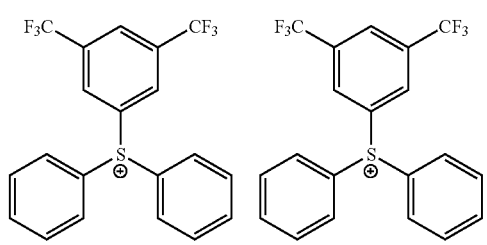
B-11
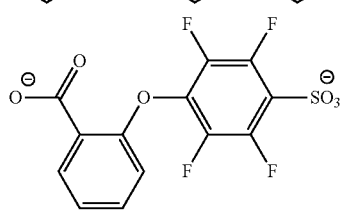
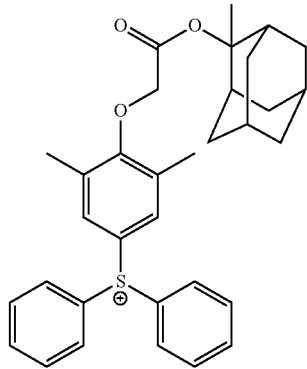

-continued
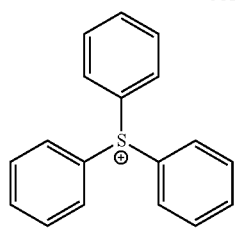
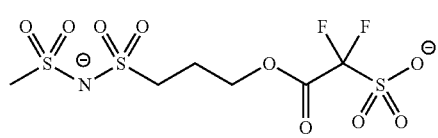
B-12
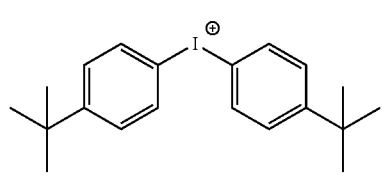
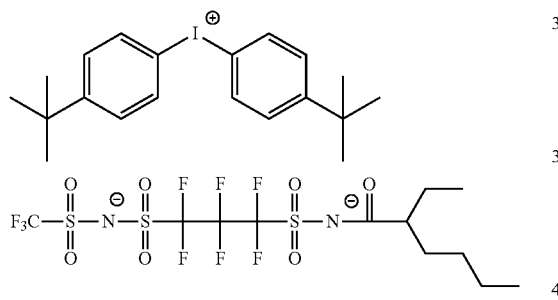
B-13
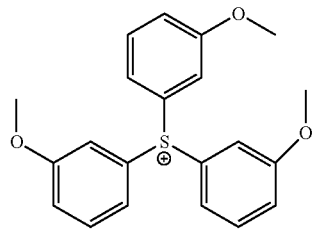
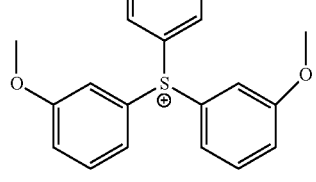
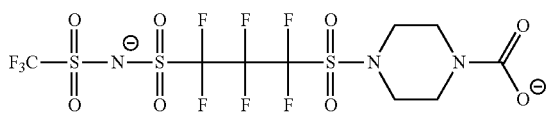
-continued
B-14
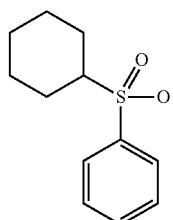 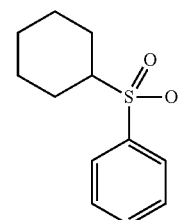
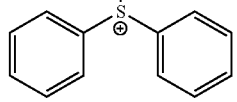 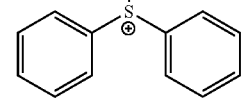
B-15
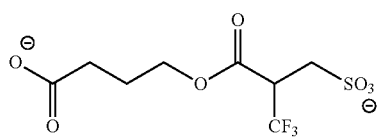
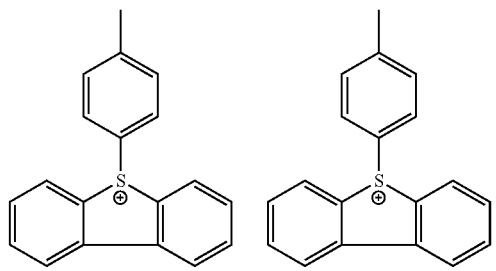 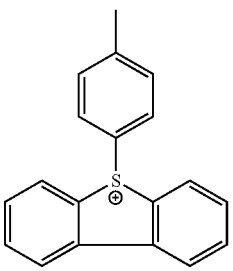
B-16
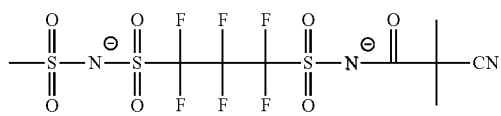 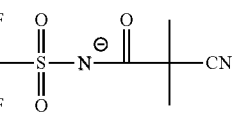
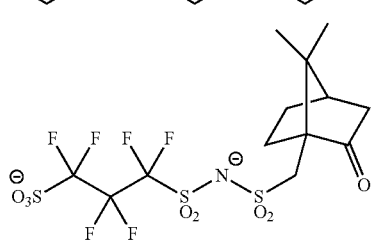

B-17
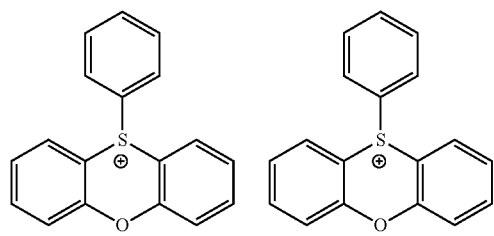
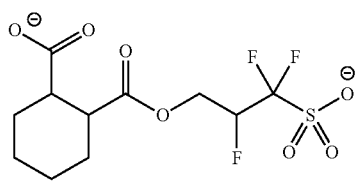
B-18
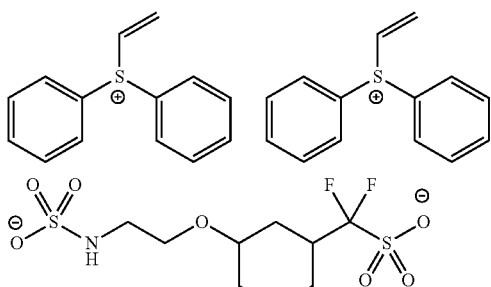
B-19
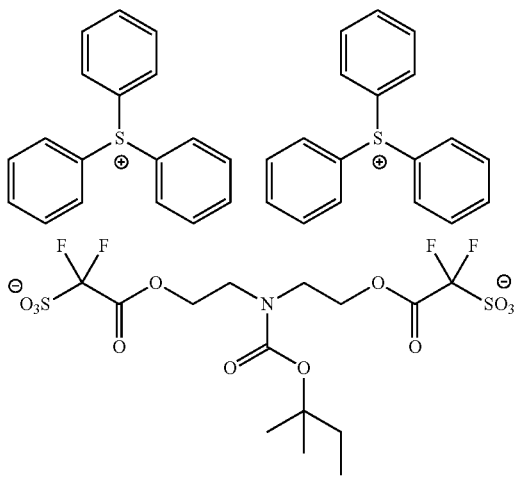
B-20
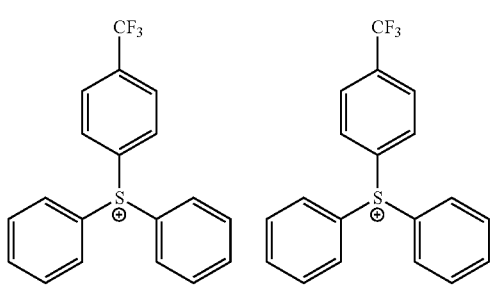
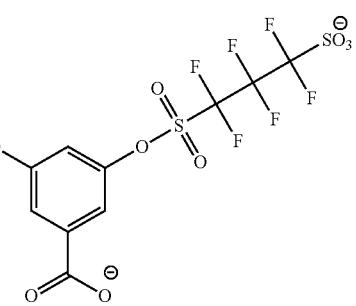
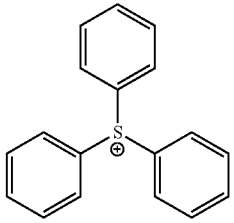
B-21
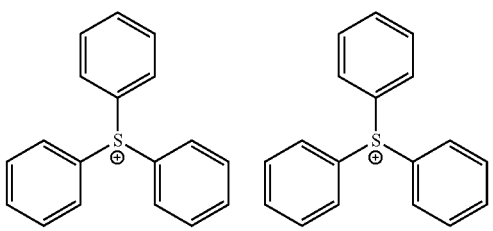
B-22
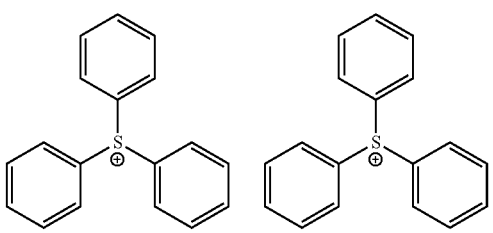
B-23
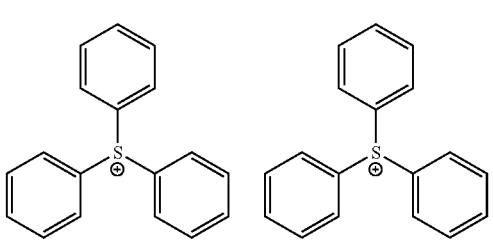

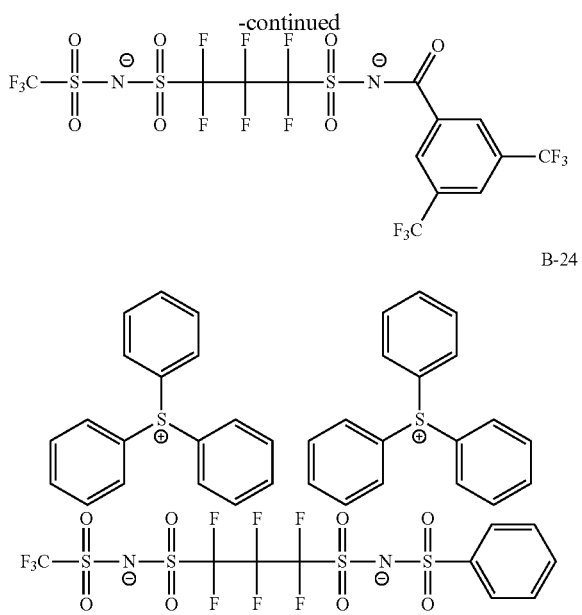

B-24

(Second Solvent)

Second solvents (solvents D-1 to D-6) shown in Table 3 are shown below.

D-1: Propylene glycol monomethyl ether (abbreviation: PGME, SP value: 23.0 MPa$^{1/2}$)

D-2: Cyclohexanone (SP value: 20.0 MPa$^{1/2}$)

D-3: γ-Butyrolactone (SP value: 23.8 MPa$^{1/2}$)

D-4: Ethyl lactate (SP value: 24.4 MPa$^{1/2}$)

D-5: Propylene glycol monomethyl ether acetate (abbreviation: PGMEA, SP value: 17.9 MPa$^{1/2}$)

D-6: 2-Heptanone (SP value: 18.1 MPa$^{1/2}$)

<Preparation of Second Solution>

The specific photoacid generator and the second solvent were mixed so that a concentration of solid contents shown in Table 3 was obtained, and the mixture was stirred for 6 hours to prepare a second solution (solutions Y-1 to Y-24, a solution YY-1, and a solution YY-2). Furthermore, in the second solution, the solid content means all the components excluding the solvent. In addition, in the solution Y-7 and the solution Y-9 in Table 3, the solvent ratio represents a mass ratio.

TABLE 3

| | Composition of second solution | | | |
|---|---|---|---|---|
| | Specific photoacid generator | Second solvent | | |
| | | Type | SP value (MPa$^{1/2}$) | Concentration of solid contents (% by mass) |
| Y-1 | B-1 | D-1 | 23.0 | 10.0 |
| Y-2 | B-2 | D-1 | 23.0 | 10.0 |
| Y-3 | B-3 | D-1 | 23.0 | 10.0 |
| Y-4 | B-4 | D-2 | 20.0 | 20.0 |
| Y-5 | B-5 | D-3 | 23.8 | 25.0 |
| Y-6 | B-6 | D-1 | 23.0 | 20.0 |
| Y-7 | B-7 | D-1/D-3 (90/10) | D-1: 23.0 D-3: 23.8 | 15.0 |
| Y-8 | B-8 | D-1 | 23.0 | 10.0 |
| Y-9 | B-9 | D-1/D-2 (70/30) | D-1: 23.0 D-2: 20.0 | 10.0 |
| Y-10 | B-10 | D-2 | 20.0 | 20.0 |
| Y-11 | B-11 | D-2 | 20.0 | 15.0 |
| Y-12 | B-12 | D-3 | 23.8 | 20.0 |
| Y-13 | B-13 | D-1 | 23.0 | 10.0 |
| Y-14 | B-14 | D-1 | 23.0 | 10.0 |
| Y-15 | B-15 | D-4 | 24.4 | 10.0 |
| Y-16 | B-16 | D-1 | 23.0 | 10.0 |
| Y-17 | B-17 | D-1 | 23.0 | 10.0 |
| Y-18 | B-18 | D-4 | 24.4 | 10.0 |
| Y-19 | B-19 | D-1 | 23.0 | 10.0 |
| Y-20 | B-20 | D-1 | 23.0 | 10.0 |
| YY-1 | B-1 | D-5 | 17.9 | 5.0 |
| YY-2 | B-1 | D-6 | 18.1 | 10.0 |
| Y-21 | B-21 | D-1 | 23.0 | 10.0 |
| Y-22 | B-22 | D-1 | 23.0 | 10.0 |
| Y-23 | B-23 | D-1 | 23.0 | 10.0 |
| Y-24 | B-24 | D-1 | 23.0 | 10.0 |

[Resin (A)]

As the resins (A) (A-1, A-3, A-5, A-8, A-9, and A-li) shown in Table 4 and Table 7, the resins A-1, A-3, A-5, A-8, A-9, and A-11 listed in the [Preparation of First Solution] column were used.

[Specific Photoacid Generator]

As the specific photoacid generators (B-2, B-3, B-5, B-10, B-12, and B-20) shown in Table 4 and Table 7, the photoacid generators B-2, B-3, B-5, B-10, B-12, and B-20 listed in the [Preparation of Second Solution] column were used.

[Acid Diffusion Control Agent]

The structures of acid diffusion control agents (N-1 to N-7) shown in Table 4 and Table 7 are shown below.

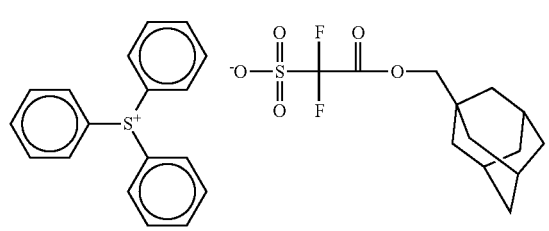

N-1

-continued
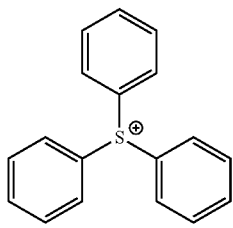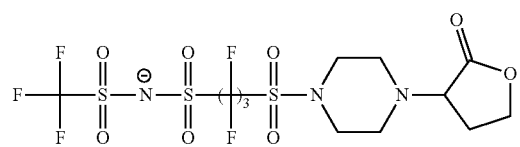
N-2
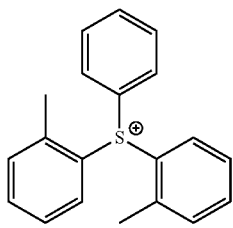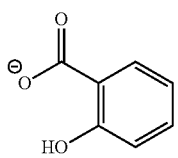
N-3
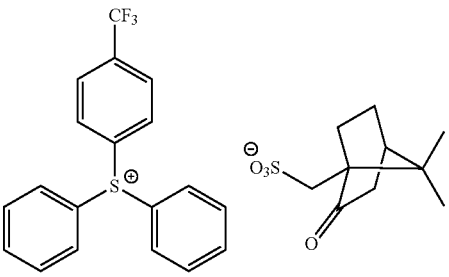
N-4
N-5
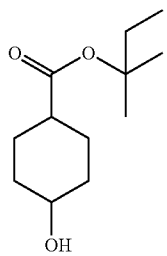
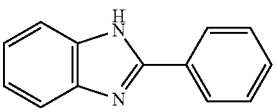
N-6
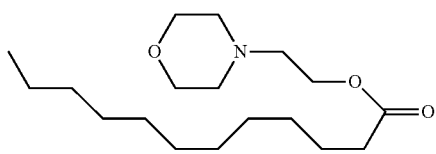
N-7
[Hydrophobic Resin]
The structures of hydrophobic resins E (compounds E-1 to E-6) shown in Table 4 are shown below. Furthermore, the numerical value of each repeating unit represents a molar ratio.
-continued
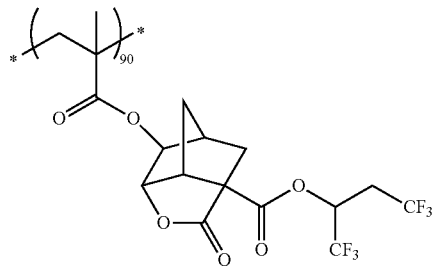
E-2
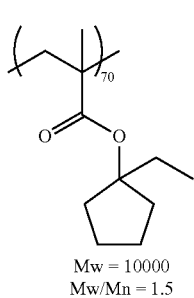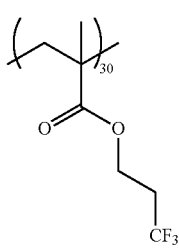
E-1
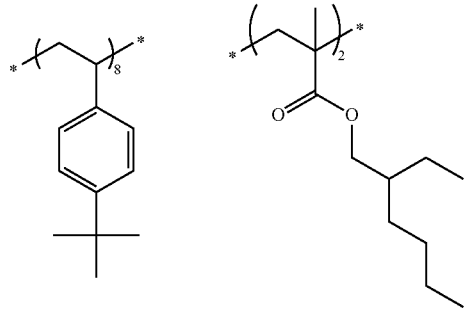

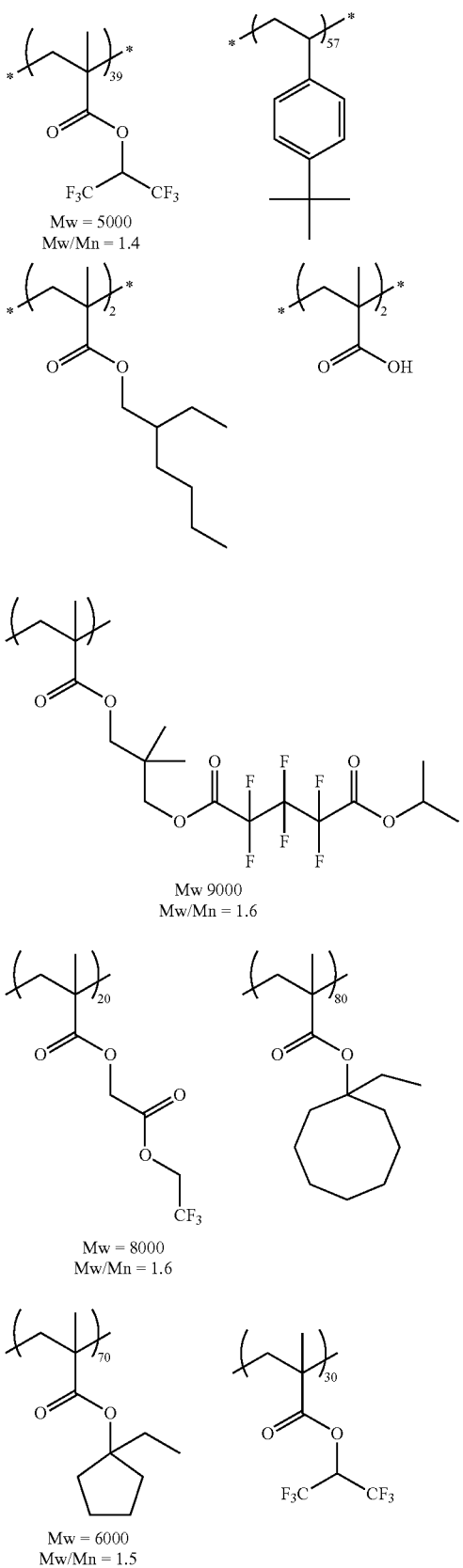

[Additionally Added Solvent]

As additionally added solvents (C-1 to C-3) shown in Table 4 and Table 7, the above-mentioned first solvents C-1 to C-3 listed in the [Preparation of First Solution] column were used.

In addition, as additionally added solvents (D-1 to D-6) shown in Table 4 and Table 7, the second solvents D-1 to D-6 listed in the [Preparation of second solution] column were used.

Surfactants (H-1 to H-3) shown in Table 7 are shown below.

"H-1": MEGAFACE F176 (manufactured by DIC Corporation, fluorine-based surfactant)

"H-2": MEGAFACE R08 (manufactured by DIC Corporation, fluorine- based and silicon-based surfactant)

"H-3": PF656 (manufactured by OMNOVA Solutions Inc., fluorine-based surfactant)

[Preparation of Resist Composition for ArF Exposure]

The respective components shown in Table 4 were mixed by a compounding method shown in the table so that the concentration of solid contents was 4% by mass. The obtained mixed liquid was filtered initially through a nylon-made filter having a pore diameter of 5 nm, then through a polyethylene-made filter having a pore diameter of 3 nm, and lastly through a polyethylene-made filter having a pore diameter of 1 nm in this order to prepare a resist composition for ArF exposure. Furthermore, the solid content as mentioned herein means all the components other than the solvent.

Compounding methods shown in Table 4 and Table 7 are shown below.

"Compounding method 1 (corresponding to "1" in the "Compounding method" column in Table 4 and Table 7)": The first solvent and other components to be blended shown in Table 4 and Table 7 are mixed with a solution obtained by mixing the first solution and the second solution, and compounded. Furthermore, for example, in a case of the resist composition Re-2, the first solvent to be additionally added is C-1 (see the "Additionally added solvent 1" column in Table 4), and corresponds to the first solvent (solvent C-1) included in the solution X-2 which is the first solution.

"Compounding method 2 (corresponding to "2" in the "Compounding method" column in Table 4 and Table 7)": Other components to be blended shown in Table 4 and Table 7 are mixed with a solution obtained by mixing the first solution and the second solution, and compounded. Furthermore, in the compounding method 2, the first solvent is not additionally added, and the concentration of solid contents of the first solution is adjusted to be low.

"Compounding method 3 (corresponding to "3" in the "Compounding method" column in Table 4 and Table 7)": The specific photoacid generator and other components to be blended shown in Table 4 and Table 7 are directly added to and mixed with the first solution, and compounded.

"Compounding method 4 (corresponding to "4" in the "Compounding method" column in Table 4 and Table 7)": The resin (A), the specific photoacid generator, and other components to be blended shown in Table 4 and Table 7 are directly mixed and compounded.

"Compounding method 5 (corresponding to "5" in the "Compounding method" column in Table 4)": The resin (A) and other components to be blended shown in Table 4 and Table 7 are directly added to and mixed with the second solution, and compounded.

Table 4 is shown below. In addition, for each of the resist compositions Re-1 to Re-24 and Re-42 to Re-61, a relationship among the resin (A), the specific photoacid generator, the first solution, the second solution, and the additionally added solvent is shown together is shown in Table 5.

In the "First solution-1" (and "First solution-2") column in Table 5, a case where the SP value of the first solvent included in the first solution-1 (and the first solution-2) is less than 18.5 MPa$^{1/2}$ is indicated by "A" and a case where the SP value is 18.5 MPa$^{1/2}$ or more is indicated by "B" in the "Whether SP value is less than 18.5 MPa$^{1/2}$" column. In addition, a case where the concentration of solid contents of the first solution-1 (and the first solution-2) satisfies 5.0% to 20.0% by mass is indicated by "A", and a case where the concentration of solid contents does not satisfy the range is indicated by "B" in the "Whether concentration of solid contents satisfies 5.0% to 20.0% by mass" column.

Furthermore, in the "Second solution-1" (and "Second solution-2") column in Table 5, a case where the SP value of the second solvent included in the second solution-1 (and the second solution-2) is 18.5 MPa$^{1/2}$ or more is indicated by "A" and a case where the SP value is less than 18.5 MPa$^{1/2}$ is indicated by "B" in the "Whether SP value is less than 18.5 MPa$^{1/2}$" column.

In addition, a magnitude relationship between an SP value of the first solvent included in the first solution and an SP value of the second solvent included in the second solution is shown in the "SP value of first solvent <SP value of second solvent" column in Table 5. Specifically, a case where the relationship of the SP value of the first solvent <the SP value of the second solvent is satisfied is indicated by "A", and a case where the relationship is not satisfied is indicated by "B".

In addition, a case where the additionally added solvent includes the first solvents C-1 to C-3 is indicated by "A", and a case where the additionally added solvent does not include the first solvents C-1 to C-3 is indicated by "B" in the "Whether additionally added solvent includes first solvent" column in Table 5.

TABLE 4

| | Resist composition | | | | | | | | | | |
|---|---|---|---|---|---|---|---|---|---|---|---|
| | Resin (A) | | First solution | | | | | | Second solution | | |
| | | | First solution-1 | | First solution-2 | | Specific photoacid generator | | Second solution-1 | | Second solution-2 | |
| | Type | Amount [g] | Type | Amount [g] | Type | Amount [g] | Type | Amount [g] | Type | Amount [g] | Type | Amount [g] |
| Re-1 | | | X-1 | 80.36 | | | | | Y-1 | 4.38 | | |
| Re-2 | | | X-2 | 35.57 | | | | | Y-2 | 4.38 | | |
| Re-3 | | | X-2 | 35.57 | | | B-2 | 0.44 | | | | |
| Re-4 | | | X-2 | 35.57 | | | | | YY-1 | 8.76 | | |
| Re-5 | | | X-3 | 14.23 | | | | | Y-3 | 3.66 | | |
| Re-6 | | | X-4 | 28.50 | | | | | Y-4 | 1.06 | Y-8 | 2.13 |
| Re-7 | | | X-2 | 18.66 | X-5 | 12.44 | | | Y-5 | 0.46 | Y-12 | 0.57 |
| Re-8 | | | X-6 | 38.00 | | | | | Y-18 | 4.26 | | |
| Re-9 | | | X-7 | 37.33 | | | | | Y-7 | 1.52 | | |
| Re-10 | | | X-8 | 32.33 | | | | | Y-14 | 1.83 | Y-19 | 1.83 |
| Re-11 | | | X-9 | 44.46 | | | | | Y-16 | 4.38 | | |
| Re-12 | | | X-1 | 80.36 | | | | | Y-6 | 2.19 | | |
| Re-13 | | | X-5 | 11.86 | X-9 | 22.23 | | | Y-10 | 1.83 | | |
| Re-14 | | | X-4 | 31.11 | | | B-5 | 0.26 | | | | |
| Re-15 | | | X-2 | 37.33 | | | | | YY-1 | 5.24 | | |
| Re-16 | | | X-3 | 13.68 | | | | | Y-13 | 4.26 | | |
| Re-17 | | | X-16 | 35.57 | | | | | Y-1 | 4.38 | | |
| Re-18 | | | X-2 | 35.57 | | | | | YY-2 | 4.38 | | |
| Re-19 | | | X-16 | 37.33 | | | | | Y-3 | 2.28 | | |
| Re-20 | | | X-6 | 41.48 | | | | | YY-2 | 2.28 | | |
| Re-21 | A-1 | 3.56 | | | | | B-2 | 0.44 | | | | |
| Re-22 | A-1 | 3.56 | | | | | | | Y-1 | 4.38 | | |
| Re-23 | A-3 | 3.56 | | | | | B-5 | 0.37 | | | | |
| Re-24 | A-5 | 3.73 | | | | | | | Y-5 | 1.07 | | |

| | Resist composition | | | | | | | | | | |
|---|---|---|---|---|---|---|---|---|---|---|---|
| | Acid diffusion control agent | | | | | Additionally added solvent | | | | | |
| | Acid diffusion control agent-1 | | Acid diffusion control agent-2 | | Hydrophobic resin | | Additionally added solvent 1 | | Additionally added solvent 2 | | Additionally added solvent 3 | | Compounding method |
| | Type | Amount [g] | Type | Amount [g] | Type | Amount [g] | Type | Amount [g] | Type | Amount [g] | Type | Amount [g] | |
| Re-1 | | | | | E-1 | 0.01 | | | D-1 | 15.26 | | | 2 |
| Re-2 | | | | | E-2 | 0.01 | C-1 | 44.79 | D-1 | 15.26 | | | 1 |
| Re-3 | | | | | E-2 | 0.01 | C-1 | 44.79 | D-1 | 19.20 | | | 3 |
| Re-4 | | | | | E-1 | 0.01 | C-1 | 36.47 | D-1 | 19.20 | | | 1 |
| Re-5 | N-1 | 0.07 | | | E-1 | 0.01 | C-1 | 66.13 | D-1 | 15.90 | | | 1 |
| Re-6 | N-3 | 0.07 | N-5 | 0.07 | E-1 | 0.01 | C-1 | 42.12 | D-1 | 17.28 | D-2 | 8.75 | 1 |
| Re-7 | N-2 | 0.03 | | | E-2 | 0.01 | C-1 | 60.00 | C-2 | 3.82 | D-3 | 4.00 | 1 |
| Re-8 | N-4 | 0.15 | | | | | C-1 | 23.02 | D-4 | 34.57 | | | 1 |
| Re-9 | N-6 | 0.03 | | | E-1 | 0.01 | C-1 | 43.20 | D-1 | 13.24 | D-3 | 4.67 | 1 |
| Re-10 | N-7 | 0.08 | | | | | C-1 | 57.62 | D-1 | 6.30 | | | 1 |
| Re-11 | | | | | | | C-1 | 26.30 | D-1 | 15.26 | D-2 | 9.61 | 1 |
| Re-12 | | | | | E-1 | 0.01 | | | D-1 | 17.45 | | | 2 |

TABLE 4-continued

| | | | | | | | | | | | |
|---|---|---|---|---|---|---|---|---|---|---|---|
| Re-13 | N-1 | 0.08 | | | | C-1 | 56.35 | C-2 | 4.32 | D-2 | 3.34 | 1 |
| Re-14 | | | E-2 | 0.01 | C-1 | 63.83 | D-3 | 4.80 | | | 3 |
| Re-15 | | | E-1 | 0.01 | C-1 | 47.83 | D-4 | 9.60 | | | 1 |
| Re-16 | N-7 | 0.15 | E-2 | 0.01 | C-1 | 66.54 | D-1 | 15.37 | | | 1 |
| Re-17 | | | E-1 | 0.01 | C-3 | 44.79 | D-1 | 15.26 | | | 1 |
| Re-18 | | | E-1 | 0.01 | C-1 | 54.39 | D-6 | 5.66 | | | 1 |
| Re-19 | N-1 | 0.03 | E-2 | 0.01 | C-3 | 52.80 | D-1 | 7.55 | | | 1 |
| Re-20 | N-3 | 0.04 | | | C-1 | 29.46 | D-6 | 26.75 | | | 1 |
| Re-21 | | | E-1 | 0.01 | C-1 | 76.80 | D-1 | 19.20 | | | 4 |
| Re-22 | | | E-1 | 0.01 | C-1 | 86.40 | D-1 | 5.66 | | | 5 |
| Re-23 | N-6 | 0.07 | E-2 | 0.01 | C-1 | 76.80 | D-1 | 19.20 | | | 4 |
| Re-24 | | | | | C-1 | 67.20 | D-3 | 28.00 | | | 5 |

TABLE 5

Table 4 Continued

| | Resist composition | | | | | | | | | | |
|---|---|---|---|---|---|---|---|---|---|---|---|
| | First solution | | | | | | Second solution | | | | |
| | Resin (A) | | First solution-1 | | First solution-2 | | Specific photoacid generator | | Second solution-1 | | Second solution-2 | |
| | Type | Amount [g] | Type | Amount [g] | Type | Amount [g] | Type | Amount [g] | Type | Amount [g] | Type | Amount [g] |
| Re-42 | | | X-18 | 29.64 | | | | | Y-21 | 3.66 | | |
| Re-43 | | | X-18 | 29.64 | | | | | Y-22 | 3.66 | | |
| Re-44 | | | X-18 | 29.64 | | | | | Y-23 | 3.66 | | |
| Re-45 | | | X-18 | 29.64 | | | | | Y-24 | 3.66 | | |
| Re-46 | | | X-19 | 23.71 | | | | | Y-21 | 3.66 | | |
| Re-47 | | | X-19 | 23.71 | | | | | Y-22 | 3.66 | | |
| Re-48 | | | X-19 | 23.71 | | | | | Y-23 | 3.66 | | |
| Re-49 | | | X-19 | 23.71 | | | | | Y-24 | 3.66 | | |
| Re-50 | | | X-20 | 35.57 | | | | | Y-21 | 3.66 | | |
| Re-51 | | | X-20 | 35.57 | | | | | Y-22 | 3.66 | | |
| Re-52 | | | X-20 | 35.57 | | | | | Y-23 | 3.66 | | |
| Re-53 | | | X-20 | 35.57 | | | | | Y-24 | 3.66 | | |
| Re-54 | | | X-21 | 27.36 | | | | | Y-21 | 3.66 | | |
| Re-55 | | | X-21 | 27.36 | | | | | Y-22 | 3.66 | | |
| Re-56 | | | X-21 | 27.36 | | | | | Y-23 | 3.66 | | |
| Re-57 | | | X-21 | 27.36 | | | | | Y-24 | 3.66 | | |
| Re-58 | | | X-22 | 39.52 | | | | | Y-21 | 3.66 | | |
| Re-59 | | | X-22 | 39.52 | | | | | Y-22 | 3.66 | | |
| Re-60 | | | X-22 | 39.52 | | | | | Y-23 | 3.66 | | |
| Re-61 | | | X-22 | 39.52 | | | | | Y-24 | 3.66 | | |

| | Resist composition | | | | | | | | | | | |
|---|---|---|---|---|---|---|---|---|---|---|---|---|
| | Acid diffusion control agent | | | | | | Additionally added solvent | | | | | |
| | Acid diffusion control agent-1 | | Acid diffusion control agent-2 | | Hydrophobic resin | | Additionally added solvent 1 | | Additionally added solvent 2 | | Additionally added solvent 3 | Compounding method |
| | Type | Amount [g] | Type | Amount [g] | Type | Amount [g] | Type | Amount [g] | Type | Amount [g] | Type | Amount [g] | |
| Re-42 | N-1 | 0.07 | | | E-1 | 0.01 | C-1 | 41.12 | D-1 | 25.50 | | | 1 |
| Re-43 | N-2 | 0.07 | | | E-2 | 0.01 | C-1 | 41.12 | D-2 | 1.92 | D-1 | 23.58 | 1 |
| Re-44 | N-3 | 0.07 | | | E-3 | 0.01 | C-1 | 41.12 | D-3 | 1.92 | D-1 | 23.58 | 1 |
| Re-45 | N-4 | 0.07 | | | E-4 | 0.01 | C-1 | 41.12 | D-4 | 1.92 | D-1 | 23.58 | 1 |
| Re-46 | N-5 | 0.07 | | | E-5 | 0.01 | C-1 | 47.05 | D-5 | 1.92 | D-1 | 23.58 | 1 |
| Re-47 | N-6 | 0.07 | | | E-6 | 0.01 | C-1 | 47.05 | D-6 | 1.92 | D-1 | 23.58 | 1 |
| Re-48 | N-7 | 0.07 | | | E-1 | 0.01 | C-1 | 47.05 | D-1 | 25.5 | | | 1 |
| Re-49 | N-1 | 0.07 | | | E-2 | 0.01 | C-1 | 47.05 | D-2 | 1.92 | D-1 | 23.58 | 1 |
| Re-50 | N-2 | 0.07 | | | E-3 | 0.01 | C-1 | 35.19 | D-3 | 1.92 | D-1 | 23.58 | 1 |
| Re-51 | N-3 | 0.07 | | | E-4 | 0.01 | C-1 | 35.19 | D-4 | 1.92 | D-1 | 23.58 | 1 |
| Re-52 | N-4 | 0.07 | | | E-5 | 0.01 | C-1 | 35.19 | D-5 | 1.92 | D-1 | 23.58 | 1 |
| Re-53 | N-5 | 0.07 | | | E-6 | 0.01 | C-1 | 35.19 | D-6 | 1.92 | D-1 | 23.58 | 1 |
| Re-54 | N-6 | 0.07 | | | E-1 | 0.01 | C-1 | 43.40 | D-1 | 25.5 | | | 1 |
| Re-55 | N-7 | 0.07 | | | E-2 | 0.01 | C-1 | 43.40 | D-2 | 1.92 | D-1 | 23.58 | 1 |
| Re-56 | N-1 | 0.07 | | | E-3 | 0.01 | C-1 | 43.40 | D-3 | 1.92 | D-1 | 23.58 | 1 |
| Re-57 | N-2 | 0.07 | | | E-4 | 0.01 | C-1 | 43.40 | D-4 | 1.92 | D-1 | 23.58 | 1 |
| Re-58 | N-3 | 0.07 | | | E-5 | 0.01 | C-1 | 31.24 | D-5 | 1.92 | D-1 | 23.58 | 1 |

TABLE 5-continued

Table 4 Continued

| | | | | | | | | | | | |
|---|---|---|---|---|---|---|---|---|---|---|---|
| Re-59 | N-4 | 0.07 | E-6 | 0.01 | C-1 | 31.24 | D-6 | 1.92 | D-1 | 23.58 | 1 |
| Re-60 | N-5 | 0.07 | E-1 | 0.01 | C-1 | 31.24 | D-1 | 25.5 | | | 1 |
| Re-61 | N-6 | 0.07 | E-2 | 0.01 | C-1 | 31.24 | D-2 | 1.92 | D-1 | 23.58 | 1 |

TABLE 6

Table 5

Relationship among resin (A), specific photoacid generator, first solution, second solution, and additionally added solvent

| | | First solution | | | | | | | | Specific |
|---|---|---|---|---|---|---|---|---|---|---|
| | | First solution-1 | | | | First solution-2 | | | | |
| | Resin (A) Type | Type | SP value | Whether SP value is less than 18.5 MPa$^{1/2}$ | Concentration of solid contents (% by mass) | Whether concentration of solid contents satisfies 5.0% to 20.0% by mass | Type | SP value | Whether SP value is less than 18.5 MPa$^{1/2}$ | Concentration of solid contents (% by mass) | Whether concentration of solid contents satisfies 5.0% to 20.0% by mass | photoacid generator Type |
| Re-1 | — | X-1 | 17.9 | A | 4.4 | B | — | — | — | — | — | — |
| Re-2 | — | X-2 | 17.9 | A | 10.0 | A | — | — | — | — | — | — |
| Re-3 | — | X-2 | 17.9 | A | 10.0 | A | — | — | — | — | — | B-2 |
| Re-4 | — | X-2 | 17.9 | A | 10.0 | A | — | — | — | — | — | — |
| Re-5 | — | X-3 | 17.9 | A | 25.0 | B | — | — | — | — | — | — |
| Re-6 | — | X-4 | 17.9 | A | 12.0 | A | — | — | — | — | — | — |
| Re-7 | — | X-2 | 17.9 | A | 10.0 | A | X-5 | 18.1 | A | 15.0 | A | — |
| Re-8 | — | X-6 | 17.9 | A | 9.0 | A | — | — | — | — | — | — |
| Re-9 | — | X-7 | 17.9 | A | 10.0 | A | — | — | — | — | — | — |
| Re-10 | — | X-8 | 17.9 | A | 11.0 | A | — | — | — | — | — | — |
| Re-11 | — | X-9 | 17.9 | A | 8.0 | A | — | — | — | — | — | — |
| Re-12 | — | X-1 | 17.9 | A | 4.4 | B | — | — | — | — | — | — |
| Re-13 | — | X-5 | 18.1 | A | 15.0 | A | X-9 | 17.9 | A | 8.0 | A | — |
| Re-14 | — | X-4 | 17.9 | A | 12.0 | A | — | — | — | — | — | B-5 |
| Re-15 | — | X-2 | 17.9 | A | 10.0 | A | — | — | — | — | — | — |
| Re-16 | — | X-3 | 17.9 | A | 25.0 | B | — | — | — | — | — | — |
| Re-17 | — | X-16 | 20.0 | B | 10.0 | A | — | — | — | — | — | — |
| Re-18 | — | X-2 | 17.9 | A | 10.0 | A | — | — | — | — | — | — |
| Re-19 | — | X-16 | 20.0 | B | 10.0 | A | — | — | — | — | — | — |
| Re-20 | — | X-6 | 17.9 | A | 9.0 | A | — | — | — | — | — | — |
| Re-21 | A-1 | — | — | — | — | — | — | — | — | — | — | B-2 |
| Re-22 | A-1 | — | — | — | — | — | — | — | — | — | — | — |
| Re-23 | A-3 | — | — | — | — | — | — | — | — | — | — | B-5 |
| Re-24 | A-5 | — | — | — | — | — | — | — | — | — | — | — |

Relationship among resin (A), specific photoacid generator, first solution, second solution, and additionally added solvent

| | Second solution | | | | | |
|---|---|---|---|---|---|---|
| | Second solution-1 | | Second solution-2 | | SP value of first solvent < SP value of | Whether additionally added solvent |
| Resin | Whether SP value is less than | Concentration of solid contents | Whether SP value is less than | Concentration of solid contents | | |

TABLE 6-continued

Table 5

| | (A) Type | SP value | 18.5 MPa$^{1/2}$ | (% by mass) | Type | SP value | 18.5 MPa$^{1/2}$ | (% by mass) | second solvent | includes first solvent | Compounding method |
|---|---|---|---|---|---|---|---|---|---|---|---|
| Re-1 | Y-1 | 23.0 | A | 10.0 | — | — | — | — | A | B | 2 |
| Re-2 | Y-2 | 23.0 | A | 10.0 | — | — | — | — | A | A | 1 |
| Re-3 | — | — | — | — | — | — | — | — | — | A | 3 |
| Re-4 | YY-1 | 17.9 | B | 5.0 | — | — | — | — | B | A | 1 |
| Re-5 | Y-3 | 23.0 | A | 10.0 | — | — | — | — | A | A | 1 |
| Re-6 | Y-4 | 20.0 | A | 20.0 | Y-8 | 23.0 | A | 10.0 | A | A | 1 |
| Re-7 | Y-5 | 23.8 | A | 25.0 | Y-12 | 23.8 | A | 20.0 | A | A | 1 |
| Re-8 | Y-18 | 24.4 | A | 10.0 | — | — | — | — | A | A | 1 |
| Re-9 | Y-7 | D-1: 23.0 D-3: 23.8 | A | 15.0 | — | — | — | — | A | A | 1 |
| Re-10 | Y-14 | 23.0 | A | 10.0 | Y-19 | 23.0 | A | 10.0 | A | A | 1 |
| Re-11 | Y-16 | 23.0 | A | 10.0 | — | — | — | — | A | A | 1 |
| Re-12 | Y-6 | 23.0 | A | 20.0 | — | — | — | — | A | B | 2 |
| Re-13 | Y-10 | 20.0 | A | 20.0 | — | — | — | — | A | A | 1 |
| Re-14 | — | — | — | — | — | — | — | — | — | A | 3 |
| Re-15 | YY-1 | 17.9 | B | 5.0 | — | — | — | — | B | A | 1 |
| Re-16 | Y-13 | 23.0 | A | 10.0 | — | — | — | — | A | A | 1 |
| Re-17 | Y-1 | 23.0 | A | 10.0 | — | — | — | — | A | A | 1 |
| Re-18 | YY-2 | 18.1 | B | 10.0 | — | — | — | — | A | A | 1 |
| Re-19 | Y-3 | 23.0 | A | 10.0 | — | — | — | — | A | A | 1 |
| Re-20 | YY-2 | 18.1 | B | 10.0 | — | — | — | — | A | A | 1 |
| Re-21 | — | — | — | — | — | — | — | — | — | — | 4 |
| Re-22 | Y-1 | 23.0 | A | 10.0 | — | — | — | — | — | — | 5 |
| Re-23 | — | — | — | — | — | — | — | — | — | — | 4 |
| Re-24 | Y-5 | 23.8 | A | 25.0 | — | — | — | — | — | — | 5 |

TABLE 7

Table 5 Continued

Relationship among resin (A), specific photoacid generator, first solution, second solution, and additionally added solvent

| | | First solution | | | | | | | | | |
|---|---|---|---|---|---|---|---|---|---|---|---|
| | | First solution-1 | | | | | First solution-2 | | | | |
| | Resin (A) Type | Type | SP value | Whether SP value is less than 18.5 MPa$^{1/2}$ | Con- centration of solid contents (% by mass) | Whether concentration of solid contents satisfies 5.0% to 20.0% by mass | Type | SP value | Whether SP value is less than 18.5 MPa$^{1/2}$ | Con- centration of solid contents (% by mass) | Whether concentration of solid contents satisfies 5.0% to 20.0% by mass | Specific photoacid generator Type |
| Re-42 | — | X-18 | 17.9 | A | 12.0 | A | — | — | — | — | — | — |
| Re-43 | — | X-18 | 17.9 | A | 12.0 | A | — | — | — | — | — | — |
| Re-44 | — | X-18 | 17.9 | A | 12.0 | A | — | — | — | — | — | — |
| Re-45 | — | X-18 | 17.9 | A | 12.0 | A | — | — | — | — | — | — |
| Re-46 | — | X-19 | 17.9 | A | 15.0 | A | — | — | — | — | — | — |
| Re-47 | — | X-19 | 17.9 | A | 15.0 | A | — | — | — | — | — | — |
| Re-48 | — | X-19 | 17.9 | A | 15.0 | A | — | — | — | — | — | — |
| Re-49 | — | X-19 | 17.9 | A | 15.0 | A | — | — | — | — | — | — |
| Re-50 | — | X-20 | 17.9 | A | 10.0 | A | — | — | — | — | — | — |
| Re-51 | — | X-20 | 17.9 | A | 10.0 | A | — | — | — | — | — | — |

TABLE 7-continued

Table 5 Continued

| | | | | | | | | | | | | |
|---|---|---|---|---|---|---|---|---|---|---|---|---|
| Re-52 | — | X-20 | 17.9 | A | 10.0 | A | — | — | — | — | — | — |
| Re-53 | — | X-20 | 17.9 | A | 10.0 | A | — | — | — | — | — | — |
| Re-54 | — | X-21 | 17.9 | A | 13.0 | A | — | — | — | — | — | — |
| Re-55 | — | X-21 | 17.9 | A | 13.0 | A | — | — | — | — | — | — |
| Re-56 | — | X-21 | 17.9 | A | 13.0 | A | — | — | — | — | — | — |
| Re-57 | — | X-21 | 17.9 | A | 13.0 | A | — | — | — | — | — | — |
| Re-58 | — | X-22 | 17.9 | A | 9.0 | A | — | — | — | — | — | — |
| Re-59 | — | X-22 | 17.9 | A | 9.0 | A | — | — | — | — | — | — |
| Re-60 | — | X-22 | 17.9 | A | 9.0 | A | — | — | — | — | — | — |
| Re-61 | — | X-22 | 17.9 | A | 9.0 | A | — | — | — | — | — | — |

Relationship among resin (A), specific photoacid generator, first solution, second solution, and additionally added solvent

| | | | Second solution | | | | | | | |
|---|---|---|---|---|---|---|---|---|---|---|
| | | Second solution-1 | | | Second solution-2 | | | SP value | | |
| | Resin (A) Type | SP value | Whether SP value is less than 18.5 MPa$^{1/2}$ | Con- centration of solid contents (% by mass) | Type | SP value | Whether SP value is less than 18.5 MPa$^{1/2}$ | Concentration of solid contents (% by mass) | of first solvent < SP value of second solvent | Whether additionally added solvent includes first solvent | Compounding method |
| Re-42 | Y-21 | 23.0 | A | 10.0 | — | — | — | — | A | A | 1 |
| Re-43 | Y-22 | 23.0 | A | 10.0 | — | — | — | — | A | A | 1 |
| Re-44 | Y-23 | 23.0 | A | 10.0 | — | — | — | — | A | A | 1 |
| Re-45 | Y-24 | 23.0 | A | 10.0 | — | — | — | — | A | A | 1 |
| Re-46 | Y-21 | 23.0 | A | 10.0 | — | — | — | — | A | A | 1 |
| Re-47 | Y-22 | 23.0 | A | 10.0 | — | — | — | — | A | A | 1 |
| Re-48 | Y-23 | 23.0 | A | 10.0 | — | — | — | — | A | A | 1 |
| Re-49 | Y-24 | 23.0 | A | 10.0 | — | — | — | — | A | A | 1 |
| Re-50 | Y-21 | 23.0 | A | 10.0 | — | — | — | — | A | A | 1 |
| Re-51 | Y-22 | 23.0 | A | 10.0 | — | — | — | — | A | A | 1 |
| Re-52 | Y-23 | 23.0 | A | 10.0 | — | — | — | — | A | A | 1 |
| Re-53 | Y-24 | 23.0 | A | 10.0 | — | — | — | — | A | A | 1 |
| Re-54 | Y-21 | 23.0 | A | 10.0 | — | — | — | — | A | A | 1 |
| Re-55 | Y-22 | 23.0 | A | 10.0 | — | — | — | — | A | A | 1 |
| Re-56 | Y-23 | 23.0 | A | 10.0 | — | — | — | — | A | A | 1 |
| Re-57 | Y-24 | 23.0 | A | 10.0 | — | — | — | — | A | A | 1 |
| Re-58 | Y-21 | 23.0 | A | 10.0 | — | — | — | — | A | A | 1 |
| Re-59 | Y-22 | 23.0 | A | 10.0 | — | — | — | — | A | A | 1 |
| Re-60 | Y-23 | 23.0 | A | 10.0 | — | — | — | — | A | A | 1 |
| Re-61 | Y-24 | 23.0 | A | 10.0 | — | — | — | — | A | A | 1 |

[Preparation of Topcoat Composition]

The following resin PT-1 (10 g), the following additive DT-1 (1.3 g), and the following additive DT-2 (0.06 g) were mixed with 4-methyl-2-pentanol (MIBC)/n-decane=70/30 (% by mass) as a solvent so that the concentration of solid contents was 3% by mass. Then, the obtained mixed liquid was filtered initially through a polyethylene-made filter having a pore diameter of 50 nm, then through a nylon-made filter having a pore diameter of 10 nm, and lastly through a polyethylene-made filter having a pore diameter of 5 nm in this order to prepare a topcoat composition. Furthermore, the solid content as mentioned herein means all the components other than the solvent. The obtained topcoat composition TC-1 was used in Examples. Furthermore, in the following resin PT-1, the numerical value of each repeating unit represents a molar ratio.

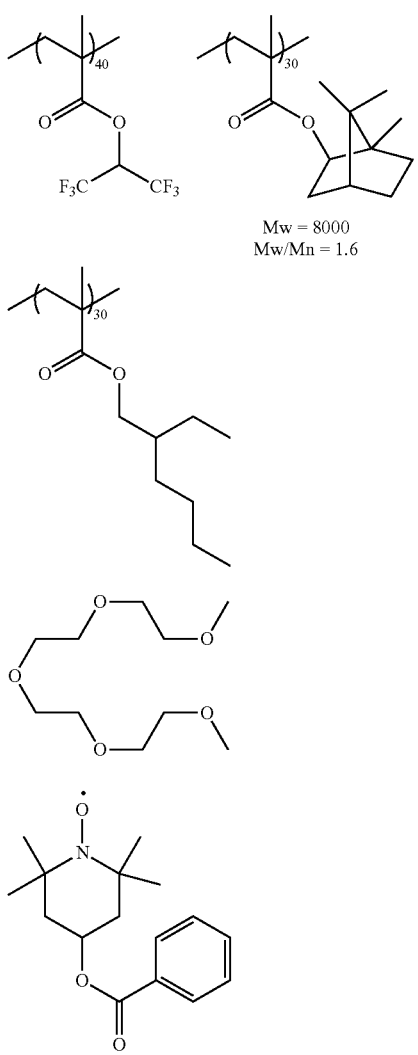

[Pattern Formation and Defect Evaluation: ArF Liquid Immersion Exposure]
[Pattern Formation and Defect Evaluation (1): ArF Liquid Immersion Exposure and Aqueous Alkali Solution Development]

A composition for forming an organic antireflection film, SOC9110D, and a composition for forming an Si-containing antireflection film, HM9825, were applied onto a silicon wafer to form an antireflection film. A resist composition for ArF exposure was applied onto the obtained antireflection film and prebaked (PB) at 100° C. for 60 seconds to form a resist film having a film thickness of 100 nm. Furthermore, in Examples 5, 8, 10, 11, 13, 17, 20, 34, 36, 38, 40, 42, 52, 54, 56, 58, and 60, and Comparative Example 4, the topcoat composition TC-1 was formed on the resist film so that the film thickness was 100 nm.

The obtained wafer was exposed through a 6% halftone mask having a 1:1 line-and-space pattern with a line width of 100 nm by using an ArF excimer laser liquid immersion scanner (manufactured by ASML; XT1700i, NA 0.85, Annular, outer sigma 0.9, inner sigma 0.6). Ultrapure water was used as the immersion liquid. Thereafter, the wafer was post-exposure baked (PEB) at 90° C. for 60 seconds. Thereafter, the wafer was puddle-developed with an aqueous tetramethylammonium hydroxide solution (2.38% by mass) as a developer for 30 seconds and rinsed with pure water to obtain a 1:1 line-and-space pattern having a line width of 100 nm.

Figure 2:
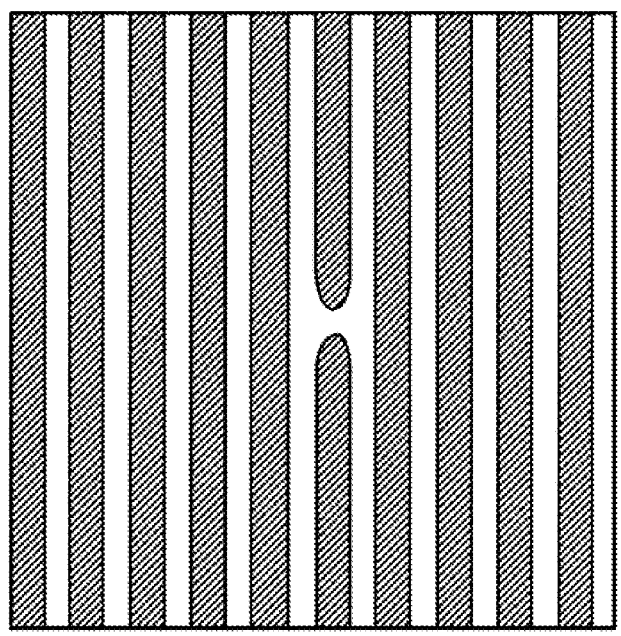
FIG. 2 is a schematic view for illustrating an evaluation method for defect evaluation after pattern formation, and is another example of a defect observed.

The obtained pattern wafer was examined with a defect evaluation device UVision 5 manufactured by Applied Materials, Inc., and a defect MAP was created. Thereafter, an image of a defect was acquired using SEMVision G4 (manufactured by Applied Materials, Inc.), and the number of actual defects per sheet of the silicon wafer was calculated. Furthermore, the actual defects generated in the pattern wafer are observed as an image as shown in FIG. 1 and FIG. 2, for example.

The number of the obtained actual defects was evaluated according to the following evaluation standard. A smaller number of defects indicate better results. The evaluation results are shown in Table 6 below.

"S": The number of defects is 50 or less

"A": The number of defects is more than 50 and 200 or less

"B": The number of defects is more than 200 and 300 or less

"C": The number of defects is more than 300 and 400 or less

"D": The number of defects is more than 400 and 500 or less

"E": The number of defects is more than 500

[Pattern Formation and Defect Evaluation (2): ArF Liquid Immersion Exposure and Organic Solvent Development]

Pattern formation and evaluation of the number of defects were carried out by the same method as in [Pattern Formation and Defect Evaluation (1): ArF Liquid Immersion Exposure and Aqueous Alkali Solution Development], except that a 1:1 line-and-space pattern with a line width of 100 nm was formed by performing puddle-development with butyl acetate as a developer for 30 seconds and performing rinsing with methyl isobutyl carbinol (MIBC). The evaluation results are shown in Table 6 below.

Table 6 is shown below.

In the "Pattern forming method" column in Table 6, (1) represents aqueous alkali solution development, and (2) represents organic solvent development.

TABLE 8

Table 6

| | Resist composition | Topcoat composition | Pattern forming method | Defects |
|---|---|---|---|---|
| Example 1 | Re-1 | — | (1) | A |
| Example 2 | Re-2 | — | (1) | S |
| Example 3 | Re-3 | — | (1) | D |
| Example 4 | Re-4 | — | (1) | D |
| Example 5 | Re-5 | TC-1 | (1) | A |
| Example 6 | Re-6 | — | (1) | S |
| Example 7 | Re-7 | — | (1) | S |
| Example 8 | Re-8 | TC-1 | (1) | S |
| Example 9 | Re-9 | — | (1) | S |
| Example 10 | Re-10 | TC-1 | (1) | S |
| Example 11 | Re-11 | TC-1 | (1) | S |
| Example 12 | Re-12 | — | (2) | A |
| Example 13 | Re-13 | TC-1 | (2) | S |
| Example 14 | Re-14 | — | (2) | D |
| Example 15 | Re-15 | — | (2) | D |
| Example 16 | Re-16 | — | (2) | A |
| Example 17 | Re-17 | TC-1 | (1) | B |
| Example 18 | Re-18 | — | (1) | C |
| Example 19 | Re-19 | — | (2) | B |
| Example 20 | Re-20 | TC-1 | (2) | C |
| Comparative Example 1 | Re-21 | — | (1) | E |
| Comparative Example 2 | Re-22 | — | (1) | E |
| Comparative Example 3 | Re-23 | — | (2) | E |
| Comparative Example 4 | Re-24 | TC-1 | (2) | E |
| Example 34 | Re-42 | TC-1 | (1) | S |
| Example 35 | Re-43 | — | (1) | S |
| Example 36 | Re-44 | TC-1 | (1) | S |
| Example 37 | Re-45 | — | (1) | S |
| Example 38 | Re-46 | TC-1 | (1) | S |
| Example 39 | Re-47 | — | (1) | S |
| Example 40 | Re-48 | TC-1 | (1) | S |
| Example 41 | Re-49 | — | (1) | S |
| Example 42 | Re-50 | TC-1 | (1) | S |
| Example 43 | Re-51 | — | (1) | S |
| Example 44 | Re-52 | TC-1 | (1) | S |
| Example 45 | Re-53 | — | (1) | S |
| Example 46 | Re-54 | TC-1 | (1) | S |
| Example 47 | Re-55 | — | (1) | S |
| Example 48 | Re-56 | TC-1 | (1) | S |
| Example 49 | Re-57 | — | (1) | S |
| Example 50 | Re-58 | TC-1 | (1) | S |
| Example 51 | Re-59 | — | (1) | S |
| Example 52 | Re-60 | TC-1 | (1) | S |
| Example 53 | Re-61 | — | (1) | S |

From the results of Table 6, it is clear that defects are suppressed by the production methods of Examples. On the other hand, it is clear that the performance of suppressing defects does not satisfy the desired requirement with the production methods of Comparative Examples.

From the results of Table 6, it is clear that in a case where the production method of the embodiment of the present invention satisfies the following condition T1 (preferably the following condition T2, and more preferably the following condition T3), defects are further suppressed.

Condition Ti: The production method of the embodiment of the present invention includes a step A, a step B2', a step B3, and the following step C2.

Step A: A step of preparing a first solution including an acid-decomposable resin and a first solvent Step B2': A step of preparing a second solution including a specific photoacid generator and a second solvent having a higher SP value than the first solvent Step B3: A step of mixing the first solution with the second solution Step C2: A step of further mixing other components to be blended in the resist composition with a solution obtained through the step B3 (a third solution).

Condition T2: The production method of the embodiment of the present invention includes a step A', a step B2", a step B3, and the following step C2.

Step A': A step of preparing a first solution including an acid-decomposable resin and a first solvent having an SP value of less than 18.5 MPa$^{1/2}$ Step B2": A step of preparing a second solution including a specific photoacid generator and a second solvent having an SP value of 18.5 MPa$^{1/2}$ or more Step B3: A step of mixing the first solution with the second solution Step C2: A step of further mixing other components to be blended in the resist composition with a solution obtained through the step B3 (a third solution).

Condition T3: The production method of the embodiment of the present invention includes a step A''', a step B2", a step B3, and the following step C3'.

Step A''': A step of preparing a first solution including an acid-decomposable resin and a first solvent having an SP value of less than 18.5 MPa$^{1/2}$, and having a concentration of solid contents of 5.0% to 20.0% by mass Step B2": A step of preparing a second solution including a specific photoacid generator and a second solvent having an SP value of 18.5 MPa$^{1/2}$ or more Step B3: A step of mixing the first solution with the second solution Step C3': A step of further mixing the first solvent and other components to be blended in the resist composition with a solution obtained through the step B3 (third solution).

Moreover, in a case where the resist compositions Re-1-1 to Re-24-1 were prepared by the same method as each of the compounding methods for the resist compositions Re-1 to Re-24, except that the above-mentioned acid diffusion control agent N-1, which is a monovalent salt, was used instead of the photoacid generator B, which is a polyvalent salt, a difference in the performance of suppressing defects of a pattern formed was obtained between the cases of the compounding methods 1 to 3 and the cases of the compounding methods 4 and 5 was not substantially observed. Also, in a case where the above-mentioned acid diffusion control agent N-2, N-3, or N-4 was used instead of the acid diffusion control agent N-1, a difference in the performance of suppressing defects of a pattern formed was obtained between the cases of the compounding methods 1 to 3 and the cases of the compounding methods 4 and 5 was not substantially observed.

[Preparation of Resist Composition for EUV Exposure]

The respective components shown in Table 7 were mixed so that the concentration of solid contents was 1.3% by mass. The obtained mixed liquid was filtered initially through a nylon-made filter having a pore diameter of 5 nm, then through a polyethylene-made filter having a pore diameter of 3 nm, and lastly through a polyethylene-made filter having a pore diameter of 1 nm in this order to prepare a resist composition for EUV exposure. The solid content as mentioned herein means all the components other than the solvent.

The compounding methods shown in Table 7 are as described above.

Table 7 is shown below. In addition, for each of the resist compositions Re-25 to Re-41, a relationship among the resin (A), the specific photoacid generator, the first solution, the second solution, and the additionally added solvent is shown together in Table 8.

In the "First solution-1" (and "First solution-2") column in Table 8, a case where the SP value of the first solvent included in the first solution-1 (and the first solution-2) is less than 18.5 MPa$^{1/2}$ is indicated by "A" and a case where the SP value is 18.5 MPa$^{1/2}$ or more is indicated by "B" in the "Whether SP value is less than 18.5 MPa$^{1/2}$" column. In addition, a case where the concentration of solid contents of the first solution-1 (and the first solution-2) satisfies 5.0% to 20.0% by mass is indicated by "A", and a case where the concentration of solid contents does not satisfy the range is indicated by "B" in the "Whether concentration of solid contents satisfies 5.0% to 20.0% by mass" column.

Furthermore, in the "Second solution-1" (and "Second solution-2") column in Table 8, a case where the SP value of the second solvent included in the second solution-1 (and the second solution-2) is 18.5 MPa$^{1/2}$ or more is indicated by "A" and a case where the SP value is less than 18.5 MPa$^{1/2}$ is indicated by "B" in the "Whether SP value is less than 18.5 MPa$^{1/2}$" column.

In addition, a magnitude relationship between an SP value of the first solvent included in the first solution and an SP value of the second solvent included in the second solution is shown in the "SP value of first solvent <SP value of second solvent" column in Table 8. Specifically, a case where the relationship of the SP value of the first solvent <the SP value of the second solvent is satisfied is indicated by "A", and a case where the relationship is not satisfied is indicated by "B".

In addition, a case where the additionally added solvent includes the first solvents C-1 to C-3 is indicated by "A", and a case where the additionally added solvent does not include the first solvents C-1 to C-3 is indicated by "B" in the "Whether additionally added solvent includes first solvent" column in Table 8.

TABLE 9

Table 7

| | Resist composition | | | | | | | | | | |
|---|---|---|---|---|---|---|---|---|---|---|---|
| | First solution | | | | | | Second solution | | | | |
| | Resin (A) | | First solution-1 | | First solution-2 | | Specific photoacid generator | | Second solution-1 | | Second solution-2 | |
| | Type | Amount [g] | Type | Amount [g] | Type | Amount [g] | Type | Amount [g] | Type | Amount [g] | Type | Amount [g] |
| Re-25 | | | X-10 | 70.25 | | | | | Y-11 | 0.96 | | |
| Re-26 | | | X-11 | 10.51 | | | | | Y-17 | 1.44 | | |
| Re-27 | | | X-11 | 10.51 | | | B-3 | 0.14 | | | | |
| Re-28 | | | X-11 | 10.51 | | | | | YY-1 | 2.85 | | |
| Re-29 | | | X-12 | 5.03 | | | | | Y-9 | 1.19 | | |
| Re-30 | | | X-13 | 11.11 | | | | | Y-15 | 1.38 | | |
| Re-31 | | | X-11 | 5.51 | X-14 | 8.67 | | | Y-20 | 0.74 | | |
| Re-32 | | | X-15 | 14.45 | | | | | Y-2 | 0.71 | Y-13 | 0.72 |
| Re-33 | | | X-13 | 11.56 | | | B-12 | 0.14 | | | | |
| Re-34 | | | X-11 | 10.51 | | | | | YY-2 | 1.44 | | |
| Re-35 | | | X-17 | 11.03 | | | | | Y-2 | 0.74 | | |
| Re-36 | | | X-15 | 13.89 | | | | | YY-2 | 1.38 | | |
| Re-37 | | | X-17 | 10.10 | | | | | Y-12 | 0.94 | | |
| Re-38 | A-8 | 1.16 | | | | | B-10 | 0.14 | | | | |
| Re-39 | A-9 | 1.21 | | | | | | | Y-10 | 0.43 | | |
| Re-40 | A-11 | 1.16 | | | | | B-20 | 0.14 | | | | |
| Re-41 | A-11 | 1.11 | | | | | | | Y-13 | 1.89 | | |

| | Resist composition | | | | | | | | | | | |
|---|---|---|---|---|---|---|---|---|---|---|---|---|
| | Acid diffusion control agent | | | | | | Additionally added solvent | | | | | | |
| | Acid diffusion control agent-1 | | Acid diffusion control agent-2 | | Hydrophobic resin | | Additionally added solvent 1 | | Additionally added solvent 2 | | Additionally added solvent 3 | | Compounding method |
| | Resin A Type | Amount [g] | Type | Amount [g] | Type | Amount [g] | Type | Amount [g] | Type | Amount [g] | Type | Amount [g] | |
| Re-25 | | | | | | | | | D-2 | 28.79 | | | 2 |
| Re-26 | | | | | | | C-1 | 69.61 | D-1 | 18.44 | | | 1 |
| Re-27 | | | | | | | C-1 | 79.48 | D-3 | 9.87 | | | 3 |
| Re-28 | | | | | H-1 | 0.002 | C-1 | 66.90 | D-1 | 14.81 | D-2 | 4.94 | 1 |
| Re-29 | N-1 | 0.03 | | | | | C-1 | 75.09 | D-1 | 14.06 | D-2 | 4.61 | 1 |
| Re-30 | N-1 | 0.02 | N-2 | 0.02 | H-2 | 0.002 | C-1 | 59.09 | D-4 | 28.37 | | | 1 |
| Re-31 | N-7 | 0.01 | | | H-3 | 0.002 | C-1 | 64.18 | C-2 | 11.68 | D-1 | 9.20 | 1 |
| Re-32 | | | | | | | C-1 | 75.54 | D-1 | 8.58 | | | 1 |
| Re-33 | | | | | | | C-1 | 83.36 | D-3 | 4.94 | | | 3 |
| Re-34 | | | | | | | C-1 | 49.87 | D-6 | 38.18 | | | 1 |
| Re-35 | N-5 | 0.01 | | | | | C-3 | 69.14 | D-1 | 19.07 | | | 1 |
| Re-36 | N-3 | 0.05 | | | H-1 | 0.002 | C-1 | 76.05 | D-6 | 8.63 | | | 1 |
| Re-37 | | | | | | | C-3 | 84.77 | D-3 | 4.18 | | | 1 |

TABLE 9-continued

Table 7

| | | | | | | | | |
|---|---|---|---|---|---|---|---|---|
| Re-38 | | | | | C-1 | 88.83 | D-1 | 9.87 | 4 |
| Re-39 | | | | | C-1 | 93.77 | D-3 | 4.59 | 5 |
| Re-40 | | | H-1 | 0.002 | C-1 | 88.83 | D-1 | 9.87 | 4 |
| Re-41 | | | | | C-1 | 88.83 | D-1 | 8.17 | 5 |

TABLE 10

Table 8

Relationship among resin (A), specific photoacid generator, first solution second solution, and additionally added solvent

| | | First solution | | | | | | | | | |
|---|---|---|---|---|---|---|---|---|---|---|---|
| | | First solution-1 | | | | | First solution-2 | | | | |
| | Resin (A) Type | Type | SP value | Whether SP value is less than 18.5 $MPa^{1/2}$ | Con-centration of solid contents (% by mass) | Whether concentration of solid contents satisfies 5.0% to 20.0% by mass | Type | SP value | Whether SP value is less than 18.5 $MPa^{1/2}$ | Con-centration of solid contents (% by mass) | Whether concentration of solid contents satisfies 5.0% to 20.0% by mass | Specific photoacid generator Type |
| Re-25 | — | X-10 | 17.9 | A | 1.6 | B | — | — | — | — | — | — |
| Re-26 | — | X-11 | 17.9 | A | 11.0 | A | — | — | — | — | — | — |
| Re-27 | — | X-11 | 17.9 | A | 11.0 | A | — | — | — | — | — | B-3 |
| Re-28 | — | X-11 | 17.9 | A | 11.0 | A | — | — | — | — | — | — |
| Re-29 | — | X-12 | 17.9 | A | 23.0 | B | — | — | — | — | — | — |
| Re-30 | — | X-13 | 17.9 | A | 10.0 | A | — | — | — | — | — | — |
| Re-31 | — | X-11 | 17.9 | A | 11.0 | A | X-14 | 18.1 | A | 7.0 | A | — |
| Re-32 | — | X-15 | 17.9 | A | 8.0 | A | — | — | — | — | — | — |
| Re-33 | — | X-13 | 17.9 | A | 10.0 | A | — | — | — | — | — | B-12 |
| Re-34 | — | X-11 | 17.9 | A | 11.0 | A | — | — | — | — | — | — |
| Re-35 | — | X-17 | 20.0 | B | 11.0 | A | — | — | — | — | — | — |
| Re-36 | — | X-15 | 17.9 | A | 8.0 | A | — | — | — | — | — | — |
| Re-37 | — | X-17 | 20.0 | B | 11.0 | A | — | — | — | — | — | — |
| Re-38 | A-8 | — | — | — | — | — | — | — | — | — | — | B-10 |
| Re-39 | A-9 | — | — | — | — | — | — | — | — | — | — | — |
| Re-40 | A-11 | — | — | — | — | — | — | — | — | — | — | B-20 |
| Re-41 | A-11 | — | — | — | — | — | — | — | — | — | — | — |

Relationship among resin (A), specific photoacid generator, first solution second solution, and additionally added solvent

| | Second solution | | | | | | | SP value | | |
|---|---|---|---|---|---|---|---|---|---|---|
| | Second solution-1 | | | | Second solution-2 | | | | | |
| Resin (A) Type | Type | SP value | Whether SP value is less than 18.5 $MPa^{1/2}$ | Con-centration of solid contents (% by mass) | Type | SP value | Whether SP value is less than 18.5 $MPa^{1/2}$ | Concentration of solid contents (% by mass) | SP value of first solvent < SP value of second solvent | Whether additionally added solvent includes first solvent | Compounding method |
| Re-25 | Y-11 | 20.0 | A | 15.0 | — | — | — | — | A | B | 2 |
| Re-26 | Y-17 | 23.0 | A | 10.0 | — | — | — | — | A | A | 1 |
| Re-27 | — | — | — | — | — | — | — | — | — | A | 3 |
| Re-28 | YY-1 | 17.9 | B | 5.0 | — | — | — | — | B | A | 1 |
| Re-29 | Y-9 | D-1: 23.0 D-2: 20.0 | A | 10.0 | — | — | — | — | A | A | 1 |
| Re-30 | Y-15 | 24.4 | A | 10.0 | — | — | — | — | A | A | 1 |
| Re-31 | Y-20 | 23.0 | A | 10.0 | — | — | — | — | A | A | 1 |
| Re-32 | Y-2 | 23.0 | A | 10.0 | Y-13 | 23.0 | A | 10.0 | A | A | 1 |
| Re-33 | — | — | — | — | — | — | — | — | — | A | 3 |
| Re-34 | YY-2 | 18.1 | B | 10.0 | — | — | — | — | A | A | 1 |
| Re-35 | Y-2 | 23.0 | A | 10.0 | — | — | — | — | A | A | 1 |
| Re-36 | YY-2 | 18.1 | B | 10.0 | — | — | — | — | A | A | 1 |
| Re-37 | Y-12 | 23.8 | A | 20.0 | — | — | — | — | A | A | 1 |

TABLE 10-continued

Table 8

| | | | | | | | | | | | |
|---|---|---|---|---|---|---|---|---|---|---|---|
| Re-38 | — | — | — | — | — | — | — | — | — | — | 4 |
| Re-39 | Y-10 | 20.0 | A | 20.0 | — | — | — | — | — | — | 5 |
| Re-40 | — | — | — | — | — | — | — | — | — | — | 4 |
| Re-41 | Y-13 | 23.0 | A | 10.0 | — | — | — | — | — | — | 5 |

[Pattern Formation and Defect Evaluation: EUV Exposure]
[Pattern Formation and Defect Evaluation (3): EUV Exposure and Aqueous Alkali Solution Development]

AL412 (manufactured by Brewer Science, inc.) was applied onto a silicon wafer and baked at 205° C. for 60 seconds to form an underlayer film having a film thickness of 30 nm. A resist composition for EUV shown in Table 7 was applied thereon and baked at 120° C. for 60 seconds to form a photosensitive film having a film thickness of 30 nm.

For the photosensitive film, the silicon wafer having the obtained resist film was subjected to patternwise irradiation using an EUV exposure device (manufactured by Exitech Ltd., Micro Exposure Tool, NA 0.3, Quadrupol, outer sigma 0.68, inner sigma 0.36). Furthermore, as the reticle, a mask having a line size=40 nm and a line:space=1:1 was used.

After the photosensitive film after exposure was baked at 120° C. for 60 seconds (Post Exposure Bake; PEB), it is developed with an aqueous tetramethylammonium hydroxide solution (TMAH, 2.38% by mass) for 30 seconds, and then rinsed with pure water for 30 seconds. The line-and-space pattern having a pitch of 80 nm and a line width of 40 nm (space width: 40 nm) was obtained by rotating the silicon wafer at a rotation speed of 4,000 rpm for 30 seconds and baking at 90° C. for 60 seconds.

The obtained pattern wafer was examined with a defect evaluation device UVision 5 manufactured by Applied Materials, Inc., and a defect MAP was created. Thereafter, an image of a defect was acquired using SEMVision G4 (manufactured by Applied Materials, Inc.), and the number of actual defects per sheet of the silicon wafer was calculated. Furthermore, the actual defects generated in the pattern wafer are observed as an image as shown in FIG. 1 and FIG. 2, for example.

The number of the obtained actual defects was evaluated according to the following evaluation standard. A smaller number of defects indicate better results. The evaluation results are shown in Table 9 below.

"S": The number of defects is 50 or less
"A": The number of defects is more than 50 and 200 or less
"B": The number of defects is more than 200 and 300 or less
"C": The number of defects is more than 300 and 400 or less
"D": The number of defects is more than 400 and 500 or less
"E": The number of defects is more than 500

[Pattern Formation and Defect Evaluation (4): EUV Exposure and Organic Solvent Development]

Pattern formation and evaluation of the number of defects were carried out by the same method as in [Pattern Formation and Defect Evaluation (3): EUV Exposure and AqueousAlkali Solution Development], except that a line-and-space pattern with a pitch of 80 nm and a line width of 40 nm (space width of 40 nm) was formed by performing puddle-development with butyl acetate as a developer for 30 seconds. The evaluation results are shown in Table 9 below.

Table 9 is shown below.

In the "Pattern forming method" column in Table 9, (3) represents aqueous alkali solution development, and (4) represents organic solvent development.

TABLE 11

Table 9

| | Resist composition | Pattern forming method | Defects |
|---|---|---|---|
| Example 21 | Re-25 | (3) | A |
| Example 22 | Re-26 | (3) | S |
| Example 23 | Re-27 | (3) | D |
| Example 24 | Re-28 | (3) | D |
| Example 25 | Re-29 | (3) | A |
| Example 26 | Re-30 | (3) | S |
| Example 27 | Re-31 | (3) | S |
| Example 28 | Re-32 | (4) | S |
| Example 29 | Re-33 | (4) | D |
| Example 30 | Re-34 | (3) | C |
| Example 31 | Re-35 | (3) | B |
| Example 32 | Re-36 | (4) | C |
| Example 33 | Re-37 | (4) | B |
| Comparative Example 5 | Re-38 | (3) | E |
| Comparative Example 6 | Re-39 | (3) | E |
| Comparative Example 7 | Re-40 | (4) | E |
| Comparative Example 8 | Re-41 | (4) | E |

From the results of Table 9, it is clear that defects are suppressed by the production methods of Examples. On the other hand, it is clear that the performance of suppressing defects does not satisfy the desired requirement with the production methods of Comparative Examples.

From the results of Table 9, it is clear that in a case where the production method of the embodiment of the present invention satisfies the following condition Ti (preferably the following condition T2, and more preferably the following condition T3), defects are further suppressed.

Condition T1: The production method of the embodiment of the present invention includes a step A, a step B2', a step B3, and the following step C2.

Step A: A step of preparing a first solution including an acid-decomposable resin and a first solvent Step B2': A step of preparing a second solution including a specific photoacid generator and a second solvent having a higher SP value than the first solvent Step B3: A step of mixing the first solution with the second solution Step C2: A step of further mixing other components to be blended in the resist composition with a solution obtained through the step B3 (a third solution).

Condition T2: The production method of the embodiment of the present invention includes a step A', a step B2", a step B3, and the following step C2.

Step A': A step of preparing a first solution including an acid-decomposable resin and a first solvent having an SP value of less than 18.5 $MPa^{1/2}$ Step B2": A step of preparing a second solution including a specific photoacid generator and a second solvent having an SP value of 18.5 $MPa^{1/2}$ or more Step B3: A step of mixing the first solution with the second solution Step C2: A step of further mixing other components to be blended in the resist composition with a solution obtained through the step B3 (a third solution).

Condition T3: The production method of the embodiment of the present invention includes a step A''', a step B2'', a step B3, and the following step C3'.

Step A''': A step of preparing a first solution including an acid-decomposable resin and a first solvent having an SP value of less than 18.5 MPa$^{1/2}$, and having a concentration of solid contents of 5.0% to 20.0% by mass Step B2'': A step of preparing a second solution including a specific photoacid generator and a second solvent having an SP value of 18.5 MPa$^{1/2}$ or more Step B3: A step of mixing the first solution with the second solution Step C3': A step of further mixing the first solvent and other components to be blended in the resist composition with a solution obtained through the step B3 (third solution).

Moreover, in a case where the resist compositions Re-25-1 to Re-41-1 were prepared by the same method as each of the compounding methods for the resist compositions Re-25 to Re-41, except that the above-mentioned acid diffusion control agent N-1, which is a monovalent salt, was used instead of the photoacid generator B, which is a polyvalent salt, a difference in the performance of suppressing defects of a pattern formed was obtained between the cases of the compounding methods 1 to 3 and the cases of the compounding methods 4 and 5 was not substantially observed. Also, in a case where the above-mentioned acid diffusion control agent N-2, N-3, or N-4 was used instead of the acid diffusion control agent N-1, a difference in the performance of suppressing defects of a pattern formed was obtained between the cases of the compounding methods 1 to 3 and the cases of the compounding methods 4 and 5 was not substantially observed.

What is claimed is:

1. A method for producing an actinic ray-sensitive or radiation-sensitive resin composition including at least:
   a resin having a polarity that increases due to decomposition by an action of an acid;
   a compound that generates an acid upon irradiation with actinic rays or radiation; and
   a solvent,
   in which the compound that generates an acid upon irradiation with actinic rays or radiation includes one or more compounds selected from the group consisting of the following compound (I) to the following compound (III),
   the method comprising mixing a first solution including the resin having a polarity that increases by the action of an acid and a first solvent with the one or more compounds selected from the group consisting of the compound (I) to the compound (III) to produce the actinic ray-sensitive or radiation-sensitive resin composition:
   compound (I): a compound having each one of the following structural moiety X and the following structural moiety Y, the compound generating an acid including the following first acidic moiety derived from the following structural moiety X and the following second acidic moiety derived from the following structural moiety Y upon irradiation with actinic rays or radiation,
   structural moiety X: a structural moiety which consists of an anionic moiety $A_1^-$ and a cationic moiety $M_1^+$, and forms a first acidic moiety represented by $HA_1$ upon irradiation with actinic rays or radiation,
   structural moiety Y: a structural moiety which consists of an anionic moiety $A_2^-$ and a cationic moiety $M_2^+$, and forms a second acidic moiety represented by $HA_2$, having a structure different from that of the first acidic moiety formed by the structural moiety X, upon irradiation with actinic rays or radiation,
   provided that the compound (I) satisfies the following condition I:
   condition I: a compound PI formed by substituting the cationic moiety $M_1^+$ in the structural moiety X and the cationic moiety $M_2^+$ in the structural moiety Y with $H^+$ in the compound (I) has an acid dissociation constant a1 derived from an acidic moiety represented by $HA_1$, formed by substituting the cationic moiety $M_1^+$ in the structural moiety X with $H^+$, and an acid dissociation constant a2 derived from an acidic moiety represented by $HA_2$, formed by substituting the cationic moiety $M2^+$ in the structural moiety Y with $H^+$, and the acid dissociation constant a2 is larger than the acid dissociation constant a1,
   compound (II): a compound having the two or more structural moieties X and the structural moiety Y, the compound generating an acid including the two or more first acidic moieties derived from the structural moieties X and the second acidic moiety derived from the structural moiety Y upon irradiation with actinic rays or radiation,
   provided that the compound (II) satisfies the following condition II:
   condition II: a compound PII formed by substituting the cationic moiety $M_1V$ in the structural moiety X and the cationic moiety $M2^+$in the structural moiety Y with $H^+$ in the compound (II) has an acid dissociation constant a1 derived from an acidic moiety represented by $HA_1$, formed by substituting the cationic moiety $M_1^+$ in the structural moiety X with $H^+$, and an acid dissociation constant a2 derived from an acidic moiety represented by $HA_2$, formed by substituting the cationic moiety $M2^+$in the structural moiety Y with $H^+$, and the acid dissociation constant a2 is larger than the acid dissociation constant a1, and
   compound (III): a compound having the two or more structural moieties X and the following structural moiety Z, the compound generating an acid including the two or more first acidic moieties derived from the structural moieties X and the structural moiety Z upon irradiation with actinic rays or radiation,
   structural moiety Z: a nonionic moiety capable of neutralizing an acid,
   wherein the actinic ray-sensitive or radiation-sensitive resin composition is produced by mixing the first solution and a second solution including a second solvent having a higher SP value than the first solvent and the one or more compounds selected from the group consisting of the compound (I) to the compound (III).

2. The method for producing an actinic ray-sensitive or radiation-sensitive resin composition according to claim 1, wherein an SP value of the first solvent is less than 18.5 MPa$^{1/2}$.

3. The method for producing an actinic ray-sensitive radiation-sensitive or resin composition according to claim 1, wherein the SP value of the second solvent is 18.5 MPa$^{1/2}$ or more.

4. The method for producing an actinic ray-sensitive radiation-sensitive or resin composition according to claim 2,
wherein the SP value of the second solvent is 18.5 MPa$^{1/2}$ or more.

5. The method for producing an actinic ray-sensitive or radiation-sensitive resin composition according to claim 1,
wherein a concentration of solid contents of the first solution is 5.0% to 20.0% by mass, and
the actinic ray-sensitive or radiation-sensitive resin composition is produced by further mixing a third solution obtained by mixing the first solution and the second solution with the first solvent.

6. The method for producing an actinic ray-sensitive or radiation-sensitive resin composition according to claim 2,
wherein a concentration of solid contents of the first solution is 5.0% to 20.0% by mass, and
the actinic ray-sensitive or radiation-sensitive resin composition is produced by further mixing a third solution obtained by mixing the first solution and the second solution with the first solvent.

7. The method for producing an actinic ray-sensitive or radiation-sensitive resin composition according to claim 3,
wherein a concentration of solid contents of the first solution is 5.0% to 20.0% by mass, and
the actinic ray-sensitive or radiation-sensitive resin composition is produced by further mixing a third solution obtained by mixing the first solution and the second solution with the first solvent.

8. The method for producing an actinic ray-sensitive or radiation-sensitive resin composition according to claim 4,
wherein a concentration of solid contents of the first solution is 5.0% to 20.0% by mass, and
the actinic ray-sensitive or radiation-sensitive resin composition is produced by further mixing a third solution obtained by mixing the first solution and the second solution with the first solvent.

9. A pattern forming method comprising:
forming a resist film on a support, using an actinic ray-sensitive or radiation-sensitive resin composition obtained by the method for producing an actinic ray-sensitive or radiation-sensitive resin composition according to of claim 1;
exposing the resist film; and
developing the exposed resist film, using a developer.

10. A method for manufacturing an electronic device, comprising the pattern forming method according to claim 9.

* * * * *